US007996156B2

(12) United States Patent
Beger et al.

(10) Patent No.: US 7,996,156 B2
(45) Date of Patent: Aug. 9, 2011

(54) METHODS FOR PREDICTING PROPERTIES OF MOLECULES

(75) Inventors: Richard D. Beger, White Hall, AR (US); Jon G. Wilkes, Little Rock, AR (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 567 days.

(21) Appl. No.: 10/383,602

(22) Filed: Mar. 7, 2003

(65) Prior Publication Data
US 2003/0229456 A1 Dec. 11, 2003

Related U.S. Application Data

(60) Provisional application No. 60/362,691, filed on Mar. 7, 2002.

(51) Int. Cl.
*G01N 33/48* (2006.01)
*G06F 7/60* (2006.01)
*G06G 7/58* (2006.01)

(52) U.S. Cl. ................... 702/19; 702/20; 703/2; 703/11

(58) Field of Classification Search ................... None
See application file for complete search history.

(56) References Cited

U.S. PATENT DOCUMENTS

| 4,772,560 | A | | 9/1988 | Attar |
| 4,789,832 | A | * | 12/1988 | Nagayama ............... 324/312 |
| 4,840,919 | A | | 6/1989 | Attar |
| 5,025,388 | A | | 6/1991 | Cramer, III et al. |
| 5,218,529 | A | | 6/1993 | Meyer et al. |
| 5,751,605 | A | | 5/1998 | Hurst et al. |
| 5,830,133 | A | | 11/1998 | Osten et al. |
| 5,891,643 | A | | 4/1999 | Fesik et al. |
| 6,333,149 | B1 | | 12/2001 | Sem |
| 6,898,533 | B1 | * | 5/2005 | Miller et al. ............... 702/27 |
| 2004/0220749 | A1 | | 11/2004 | Miller et al. |

FOREIGN PATENT DOCUMENTS

| JP | 10048157 | 2/1998 |
| WO | WO 01/57495 | 8/2001 |

OTHER PUBLICATIONS

Horst Joachim Schirra (1996), Structure Determination of Proteins with NMR Spectroscopy, retrieved and printed from the Internet at at a website with a URL of <http://www.cryst.bbk.ac.uk/PPS2/projects/schirra/html/home.htm> on Apr. 29, 2007.*
Horst Joachim Schirra (1996), Two Dimensional NMR Spectroscopy, retrieved and printed from the Internet at at a website with a URL of <http://www.cryst.bbk.ac.uk/PPS2/projects/schirra/html/2dnmr.htm> on Apr. 29, 2007.*
Horst Joachim Schirra,1996, Structure Determination of Proteins with NMR Spectroscopy- Three Dimensional NMR Spectroscopy, retrieved and printed from http://www.cryst.bbk.ac.uk/PPS2/projects/schirra/html/3dnmr.htm on Apr. 25, 2008.*
Castro et al., Computers and Chemistry, vol. 24, pp. 571-576, 2000.*
Beger et al., Journal of Biomolecular NMR, vol. 10, pp. 129-142, 1997.*
Katritzky et al., J. Chem. Inf. Comput. Sci. 1993, vol. 33, pp. 835-857.*
Ivanciuc et al., J. Chem. Inf. Comput. Sci. 2001, Vo. 41, pp. 536-549.*
Langmead et al., Extracting Structural Information Using Time-frequency Analysis of Protein NMR Data, Carnegie Mellon University Research Showcase, Oct. 1, 2000.*
Collantes et al., "Use of Moment of Inertia in Comparative Molecular Field Analysis to Model Chromatographic Retention of Nonpolar Solutes," *Anal. Chem.*, vol. 68, pp. 2038-2043 (1996).
Tong et al., "A Comparative Molecular Field Analysis Study of N-Benzylpiperidines as Acetylcholinesterase Inhibitors," *J. Med. Chem.*, vol. 39, pp. 380-387 (1996).
Tong et al., "Quantitative Structure—Activity Relationships (QSARs) for Estrogen Binding to the Estrogen Receptor: Predictions Across Species," *Environmental Health Perspectives*, vol. 105, pp. 1116-1124 (1997).
Hansch et al., "Exploring QSAR—Fundamentals and Applications in Chemistry and Biology," *ACS Professional Reference Book*, pp. 78-81, 85, and 95 (1995).
Wise et al., "A Relationship Between Reversed-Phase C18 Liquid Chromatographic Retention and the Shape of Polycyclic Aromatic Hydrocarbons," *Journal of Chromatographic Science*, vol. 19, pp. 457-465 (1981).
Agin et al., "The Action of Anesthetics on Excitable Membranes: A Quantum-Chemical Analysis," *Proc. N.A.S.*, vol. 53, pp. 952-958 (1965).
Pauling et al., "The Serological Properties of Simple Substances, IX. Hapten Inhibition of Precipitation of Antisera Homologous to the *o*-, *m*-, and *p*-Azophenylarsonic Acid Groups," *Serological Properties of Simple Substances*, vol. 67, pp. 1003-1012 (1945).
Nishikawa et al., "3-Substituent Effect and 3-Methylene Substituent Effect on the Structure-Reactivity Relationship of 7β-(Acylamino)-3-cephem-4-carboxylic Acid Derivatives Studied by Carbon-13 and IR Spectroscopies," *J. Med. Chem.*, vol. 27, pp. 1657-1663 (1984).
Ijzerman et al., "Quantitative Evaluation of the $\beta_2$-Adrenoceptor Intrinsic Activity of N-tert-Butylphenylethanolamines," *J. Med. Chem.*, vol. 29, pp. 549-554 (1986).

(Continued)

*Primary Examiner* — Shubo Zhou
(74) *Attorney, Agent, or Firm* — Klarquist Sparkman, LLP

(57) ABSTRACT

Structure-activity methods based on molecular descriptors that are a combination of structural information about the through-space and through-bond relationships between components of a molecule's structure and spectral data attributable to those components are disclosed. In some embodiments, a molecule is described by multiple sets of such descriptors to account for flexibility in the structure of the molecule. In a particularly disclosed embodiment, predicted $^{13}C$—$^{13}C$ COSY data and $^{13}C$—$^{13}C$ distance data are used as descriptors. Models of molecular properties may be established using the disclosed spectral data-activity methods and used to predict the properties of molecules.

35 Claims, 21 Drawing Sheets

OTHER PUBLICATIONS

Bursi et al., "Comparative Spectra Analysis (CoSA): Spectra as Three-Dimensional Molecular Descriptors for the Prediction of Biological Activities," *J. Chem. Inf. Comput. Sci.*, vol. 39, pp. 861-867 (1999).

Andersson et al., "Ultraviolet Absorption Spectra of all 209 Polychlorinated Biphenyls Evaluated by Principal Component Analysis," *Fresenius J. Anal Chem.*, vol. 357, pp. 1088-1092 (1997).

Andersson et al., "Ultraviolet Absorption Characteristics and Calculated Semi-Empirical Parameters as Chemical Descriptors in Multivariate Modeling of Polychlorinated Biphenyls," *Journal of Chemometrics*, vol. 10, pp. 171-185 (1996).

Andersson et al., "Multivariate Modeling of Polychlorinated Biphenyl-Induced Cypia Activity in Hepatocytes from Three Different Species: Ranking Scales and Species Differences," *Environmental Toxicology and Chemistry*, vol. 19, pp. 1454-1463 (2000).

Beger et al., "Comparative structural connectivity spectra analysis (CoSCoSA) models of steroids binding to the aromatase enzyme," *Journal of Molecular Recognition*, vol. 15, pp. 154-162 (2002).

Shade et al., "The Use of Carbon Thirteen Nuclear Magnetic Resonance Spectra to Predict Dioxin and Furan Binding Affinities to the Aryl Hydrocarbon Receptor," *Environmental Toxicology and Chemistry*, vol. 22, No. 3, pp. 501-509 (2003).

Beger et al., "Developing $^{13}$C NMR quantitative spectrometric data-activity relationship (QSDAR) models of steroid binding to the corticosteroid binding globulin," *Journal of Computer-Aided Molecular Design*, vol. 15, pp. 659-669 (2001).

Beger et al., "Combining NMR spectral and structural data to form models of polychlorinated dibenzodioxins, dibenzofurans, and biphenyls binding to the AhR," *Journal of Computer Aided Molecular Design*, vol. 16, pp. 727-740 (2002).

Beger et al., "$^{13}$C NMR and Electron Ionization Mass Spectrometric Data-Activity Relationship Model of Estrogen Receptor Binding," *Toxicology and Applied Pharmacology*, vol. 169, pp. 17-25 (2000).

Beger et al., "Comparative Structural Connectivity Spectra Analysis (CoSCoSA) Models of Steroid Binding to the Corticosteroid Binding Globulin," *J. Chem. Inf. Comput. Sci.*, vol. 42, pp. 1123-1131 (2002).

Beger et al., "$^{13}$C NMR Quantitative Spectrometric Data-Activity Relationship (QSDAR) Models of Steroids Binding the Aromatase Enzyme," *J. Chem. Inf. Comput.Sci.*, vol. 41, pp. 1360-1366 (2001).

Beger et al., "Models of Polychlorinated Dibenzodioxins, Dibenzofurans, and Biphenyls Binding Affinity to the Aryl Hydrocarbon Receptor Developed Using $^{13}$C NMR Data," *J. Chem. Inf. Comput. Sci.*, vol. 41, pp. 1322-1329 (2001).

Beger et al., "Producing 13C NMR, Infrared Absorption, and Electron Ionization Mass Spectrometric Data Models of the Monodechlorination of Chlorobenzenes, Chlorophenois, and Chloroanilines," *J. Chem. Inf. Comput. Sci.*, vol. 40, pp. 1449-1455 (2000).

Beger et al., "Use of $^{13}$C NMR Spectrometric Data to Produce a Predictive Model of Estrogen Receptor Binding Activity," *J. Chem. Inf. Comput. Sci.*, vol. 41, pp. 219-224 (2001).

Abstract, "Combining a Molecule's Structural and NMR Spectral Information to Form Models of Biological Activity," Brochure, Cambridge Healthtech Institute's Ninth Annual Effective Drug Discovery, May 6-8, 2002, Philadelphia, PA, published on the Internet in Feb. 2002.

Beger et al., Poster Section, "Development of $^{13}$C NMR and Mass Spectra-Based Structure-Activity Relationships for Estrogenicity," part of a large presentation entitled "NCTR's Center for Computational Toxicology: A Resource to Foster Toxicological and Regulatory Research," Abstract I-5, 1998 FDA Science Forum, Washington, D.C., Dec. 8-9, 1998.

de Gregorio et al., "QSAR modeling with the electrotopological state indices: Corticosteroids," *Journal of Computer-Aided Molecular Design*, vol. 12, pp. 557-561 (1998).

Kellogg et al., "E-state fields: Applications to 3D QSAR," *Journal of Computer Aided Molecular Design*, vol. 10, pp. 513-520 (1996).

Beger et al., "Using Simulated 2D $^{13}$C NMR Nearest Neighbor Connectivity Spectral Data Patterns to Model a Diverse Set of Estrogens," *Internet Electronic Journal of Molecular Design*, vol. 2, No. 7, pp. 435-453 (Jul. 2003).

Beger, "Computational Modeling of Biologically Active Molecules Using NMR Spectra," *Drug Discovery Today*, 11(9/10):429-435 (2006).

\* cited by examiner

METHODS FOR PREDICTING PROPERTIES OF MOLECULES

RELATED APPLICATION DATA

This Application claims the benefit of U.S. Provisional Patent Application No. 60/362,691 filed Mar. 7, 2002.

FIELD

Methods for predicting the biological, chemical and physical properties of molecules from spectral data patterns are disclosed. More particularly, methods that employ a combination of spectral data and interatomic distance data as descriptors of molecules in structure activity relationships are disclosed.

BACKGROUND

The number of known chemical compounds is vast and increasing constantly because methods for isolating and synthesizing molecules continue to improve. For instance, chemists are now able to employ the techniques of combinatorial chemistry to synthesize thousands of different chemical compounds, at once, using a mixture of only a few interchangeable chemical building blocks. Furthermore, chemists are now able to use combinatorial computer models to generate large numbers of chemical structures in silico.

Methods for predicting the properties of chemical compounds are generally based upon the related observations that the structure of a compound is related to its biological, chemical, and physical properties, and that compounds of similar structure exhibit similar properties. These observations are used to search for new compounds exhibiting a particular property. For example, dimethystilbesterol and estradiol have a phenol ring and both bind strongly to the estrogen receptor. From this observation, a reasonable deduction is that the presence of a phenol ring in a molecule increases the likelihood that the molecule will bind to the estrogen receptor. The deduction, which is a simple structure-activity relationship (SAR), narrows the scope of the search, but identification of estrogen receptor binders amongst phenolic compounds remains a matter of trial and error. Furthermore, compounds that bind to the estrogen receptor but do not contain a phenol ring are missed.

Quantitative structure-property relationships and quantitative structure-activity relationships (collectively QSAR) are attempts to quantify the observed relationships between the structure of chemical compounds and the magnitude of their properties. The property for which a model is sought is termed the "endpoint." In general, the endpoint may be any measurable biological, chemical or physical property. QSAR models are established by correlating the endpoint values of a group of compounds with some measure(s) of structure available for each of the compounds. The measure(s) used to describe or reflect structures are termed descriptors. Descriptors may reflect structure directly. For example, useful direct QSAR descriptors include fragments of structure (i.e. particular groups of atoms) which appear amongst the compounds of interest. Descriptors also may indirectly reflect structure. Indirect descriptors are useful because they may be measured for compounds of unknown structure. Indirect descriptors include physical properties that vary with molecular structure, for example, partition coefficients. Structure descriptors are obtained for a group of molecules exhibiting a range of endpoint values (called the training set) and a correlation is made between the descriptors and the endpoint. In some instances only a few of the descriptors shared amongst the training set of molecules will be important for determining a particular property. In others, a large number of descriptors may be required to adequately describe the dependence of a property on molecular structure. If one or more descriptors are sufficiently correlated with the endpoint, a mathematical or graphical QSAR representation of the dependence of the endpoint on the descriptor values can be obtained. Descriptor values for a compound of unknown endpoint may then be used along with the QSAR representation to predict an endpoint for the compound.

Qualitative spectral data-activity relationships (SDAR) and quantitative spectral data-activity relationships (QSDAR) are derived using spectral data as molecular descriptors. Spectrometric data-activity relationships directly correlate patterns of spectral data with molecular properties, rather than correlating structural features with molecular properties. Spectral data reflects the quantum mechanical states of the atoms and/or groups of atoms in a molecule and can be highly sensitive to changes in structure. For this reason, SDAR and QSDAR models reliably describe a wide variety of molecular properties (see, for example, Beger and Wilkes, "Developing $^{13}$C NMR Quantitative Spectrometric Data-Activity Relationship (QSDAR) Models of Steroid Binding to the Corticosteroid Binding Globulin," *J. Comput.-Aided Mol. Design* (2001, in press), Beger and Wilkes, "Models of Polychlorinated Dibenzodioxins, Dibenzofurans, and Biphenyls Binding Affinity to the Aryl Hydrocarbon Receptor Developed using $^{13}$C NMR data," *J. Chem. Inf. Comput. Sci.* (2001, in press), Beger et al., "$^{13}$C NMR and EI Mass Spectrometric Data-Activity Relationship (SDAR) Model of Estrogen Receptor Binding," *Toxicol. Appl. Pharmacol.,* 169: 17-25 (2000), Beger et al., "The Use of $^{13}$C NMR Spectrometric Data to produce a Predictive Model of Estrogen Receptor Binding Activity," *J. Chem. Inf. Comput. Sci.,* 41: 219-224, (2001), Beger et al., "Producing $^{13}$C NMR, Infrared Absorption and EI Mass spectrometric Data Monodechlorination Models of Chlorobenzenes, Chlorophenols, and Chloroanilines," *J. Chem. Inf. Comput. Sci.,* 40: 1449-1455 (2000), and U.S. patent application Ser. No. 09/629,557, each of which is incorporated by reference herein.). SDAR and QSDAR methods are based in part upon a correlation between a molecular property and the presence, absence, and/or strength of spectral signals at particular energies. Therefore, since a number of diverse structures can give rise to similar spectral features, SDAR and QSDAR methods permit modeling of molecular properties amongst groups of structurally dissimilar molecules. Furthermore, SDAR and QSDAR methods do not require prior knowledge of molecular structure, since spectra may be just as conveniently recorded for unknown compounds as they can be for known compounds. On the other hand, SDAR and QSDAR methods based on experimental spectra may be limited where the spectral features correlated with the endpoint are not readily distinguishable from noise.

A successful and widely used approach to modeling structure-activity relationships in silico is to correlate molecular properties with calculated descriptions of the three-dimensional (3D) arrangements of atoms. Three-dimensional descriptions are especially important for modeling intermolecular binding properties such as drug-receptor interactions, where contact between drug and target molecule may take place in a specific pattern over a significant portion of the three-dimensional molecular surface of the drug. An exemplary 3D-QSAR technique is the Comparative Molecular Field Analysis (CoMFA) method of Cramer and Wold (U.S. Pat. No. 5,025,388). The CoMFA method is based upon quantum mechanical calculations of the steric and electrostatic properties of molecules from their known structures. The calculations, in effect, map the electron density distribution around a molecule to create a 3-D picture of its steric and electrostatic fields (collectively, the molecular field). The 3-D molecular field maps are used as descriptors in a structure-activity relationship. Successful CoMFA models may be used to visualize and identify molecular features (for example, steric features due to bulky groups of atoms and electrostatic features such as the direction and magnitude of the molecular dipole) that are important for a particular drug-target interaction. Since a particular molecular field pattern may be the result of a number of underlying molecular structures, molecular field descriptors are more general than the actual structures and permit identification of structurally dissimilar molecules that exhibit similar properties by virtue of their similar 3-D molecular fields. On the other hand, CoMFA methods and other known 3D-QSAR techniques generally require making assumptions about how molecules orient themselves relative to each other upon binding. Selecting the correct common alignment of a training set containing diverse structures may be problematic, leading, for example, to incorrect predictions of binding ability. Furthermore, quantum mechanical molecular field calculations are computationally intensive.

A spectral data-activity method that attempts to combine the quantum mechanical information inherent in spectral data with a description of molecular structure is the comparative structurally assigned spectral analysis (CoSASA) method. In the CoSASA method, only the spectral features exhibited by the atoms of a structural moiety that is shared amongst a group of molecules (e.g. a particular ring system) are used as descriptors. For example, Beger and Wilkes used the assigned $^{13}C$ NMR chemical shifts of the steroid ring atoms to model steroid binding affinities to the aromatase enzyme and the corticosteroid binding globulin (see, Beger and Wilkes, "$^{13}C$ NMR Quantitative Spectrometric Data-activity Relationship (QSDAR) Models of Steroid Binding to the Aromatase Enzyme," *J. Chem. Inf. Comput. Sci.*, 41: 1360-1366 (2001) and Beger and Wilkes, "Developing $^{13}C$ NMR Quantitative Spectrometric Data-activity Relationship (QSDAR) Models of Steroid Binding to the Corticosteroid Binding Globulin," *J. Comput. Aided Molec. Design*, 15: 659-669, (2001). Addition of structural information through use of assigned spectral features was expected to improve the reliability of SDAR models. Surprisingly, however, CoSASA models of estrogen receptor binding using structurally assigned spectral data are no better than SDAR models that use unassigned spectral data as descriptors. Furthermore, CoSASA and related methods that rely on spectral data assigned to a common structural feature cannot be used to model properties of structurally dissimilar molecules.

SUMMARY

Spectral data-activity methods useful for modeling a wide variety of molecular properties amongst molecules of dissimilar structure are disclosed. According to one aspect of the methods, a molecule is described by a set of descriptors that are a combination of structural information about the through-space and through-bond relationships between components of a molecule's structure and the spectral data attributable to those components. In some embodiments, a molecule is described by multiple sets of such descriptors to account for flexibility in the structure of the molecule. The methods of the disclosure are computationally efficient and do not require making assumptions regarding intermolecular alignment, yet they provide surprisingly reliable models of intermolecular interactions, including interactions between enzymes and substrates and between hormones and their receptors.

DETAILED DESCRIPTION OF SEVERAL DISCLOSED EMBODIMENTS

Figure 1:
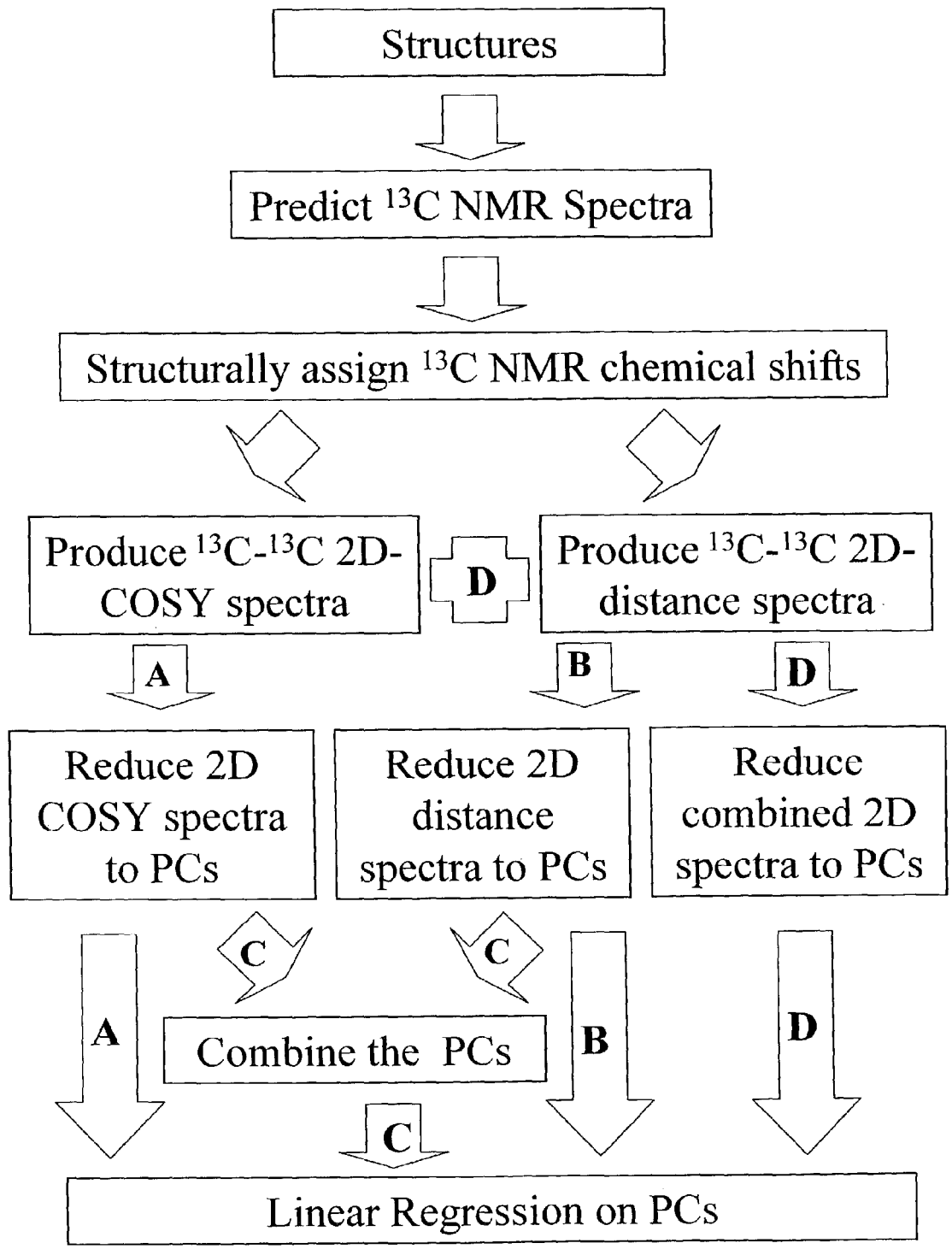
FIG. 1 is a procedural flow chart for particular embodiments of CoSCoSA modeling.

The following list of abbreviations and definitions is provided as an aid to understanding the disclosure:

Definitions and Abbreviations

The singular forms "a," "an," and "the" refer to one or more, unless the context clearly indicates otherwise.

"Comprises" means including. Hence "comprising A or B" means including A or B, or including A and B, unless the context clearly indicates otherwise.

LOO—leave-one-out cross validation
RBA—relative binding affinity
NMR—nuclear magnetic resonance
IR—infrared (spectroscopy)
MS—mass spectrometry
EI MS—electron impact mass spectrometry
UV-Vis—ultraviolet-visible (spectroscopy)
SDAR—spectral data-activity relationship
3D(Q)SDAR—three-dimensional (quantitative) spectral data activity relationship.
4D(Q)SDAR—four dimensional (quantitative) spectral data activity relationship.
Property—a property is a biological, chemical, or physical characteristic of a molecule or mixture of molecules.
Endpoint—a particular biological, chemical, or physical property or a set of such properties for a compound that is either qualitatively or quantitatively measurable.
Descriptors—any direct or indirect measure of the structure of a compound that may be obtained by theoretical or experimental means.
Training Set—endpoint data and descriptors for a group of compounds that is used to establish a relationship between the endpoint property and the structures of the compounds. Advantageously, a training set of molecules will exhibit a range of endpoint values.
Validation Set—endpoint data and descriptors for a group of compounds used to test the reliability of a relationship between an endpoint property and the structures of the compounds.
Segmented Spectral Data—spectral data that is divided into discrete sub-spectral units (bins), each of which spans a particular spectral range. The spectral range spanned by a particular bin corresponds to a range of frequencies or a range of wavelengths for spectroscopic data and may be equal to the digital resolution of the spectral data or greater. For mass spectrometric techniques, the spectral range within each bin corresponds to a particular mass or range of masses and may be equal to the digital resolution of the spectral data or greater. The bins need not all be of equal width in any one dimension.

Spectral data that is divided into bins may either encompass all the spectral data of a particular type that is available or cover only a portion of the spectral data of a particular type that is available. Each bin contains information derived from the spectral signals (or lack thereof) that appear within the spectral range defined by a particular bin. The structural component(s) of the compounds that give rise to the spectral data falling within any particular bin need not be known, but in some embodiments assignment of spectral data in particular bins to particular structural components is desirable. When the spectral data is multidimensional, spectral ranges in each of the dimensions define a bin. For multidimensional spectral data incorporating structural information, such as structural connectivity spectral data, bins may be defined by a combination of spectral ranges and ranges of values for a geometric measure of the relationship between components of molecular structure responsible for particular signals in the spectral data. For example, three-dimensional bins may be defined in terms of spectral ranges in two dimensions and ranges of distance between structural components (e.g. atoms, groups of atoms, and bonds) responsible for particular spectral signals in the spectral data of a molecule. The ranges of values used to define a bin for multidimensional data may be different with respect to each of the dimensions, the same in some dimensions and different in others, or identical in all dimensions. Furthermore, if the distance dimension is a range of distances, the bins in each range of distances may be the same or different.

Structural connectivity spectral data—spectral data that also reflects a structural relationship between components (e.g. atoms, groups of atoms, and bonds) of structure responsible for particular spectral signals. Such structural relationships may be inherent to the particular type of spectral data or a geometric relationship derived from the structure of the molecule. Examples of geometric relationships include distances, connectivity patterns, topological data, angles, and vectors between structural components. Structural connectivity spectral data may, for example, include information about the distance between structural components responsible for different spectral signals or may include information about the through bond connections between structural components responsible for different spectral signals. Additional aspects and examples of structural connectivity spectral data may be found in Example 4 below.

Spectral Data-Activity Relationship (SDAR)—a correlation between the endpoint data and the descriptors of a group of compounds, where the descriptors for each compound include one or more types of spectral data.

Nuclear Magnetic Resonance (NMR)—a phenomenon exhibited by a large number of atomic nuclei in which nuclei in a magnetic field absorb energy from a radio-frequency field at certain characteristic frequencies. Particular examples of nuclei that exhibit this phenomenon include $^{13}$C, $^{1}$H, $^{19}$F, $^{15}$N, $^{17}$O, $^{35}$S and $^{31}$P.

Mass Spectrometry (MS)—a method of chemical analysis in which the substance to be analyzed is placed in a vacuum and reduced to low pressure. The resulting vapor is exposed, for example, to a beam of electrons which causes ionization to occur, either of the molecules or their fragments. The ions thus produced are accelerated and then passed through a mass analyzer that separates the ions according to their mass.

Electron Impact Mass Spectrometry (EI MS)—a mass spectrometric technique in which the ionization of molecules and their fragments is accomplished by a beam of electrons that impacts the molecules and their fragments. Typically, as the energy of the electron beam is increased, the number of fragments produced from a molecule increases.

Infrared Spectroscopy (IR)—an analytical technique which measures a range of wavelengths (or frequencies) in the infrared region or near-infrared region of the electromagnetic spectrum that are absorbed by a specimen, which characterize its molecular constitution. Infrared absorption bands identify molecular structure components, such as aromatic, olefin, aliphatic, aldehyde, ketone, carboxylic acid, alcohol, amine, and amide groups. The frequency at which absorption occurs also reflects the frequency at which the bonds in these components stretch and and/or bend.

Ultraviolet-Visible Spectroscopy (UV-Vis)—an analytical technique which measures a range of wavelengths (or frequencies) in the ultraviolet and visible regions of the electromagnetic spectrum that are absorbed by a specimen, which characterize the electronic energy levels of its molecular constituents. UV-Vis absorption bands may be characteristic of certain molecular components, such as aromatic groups or carboxyl (CO) groups.

Fluorescence Spectroscopy—an analytical technique which measures a range of wavelengths (or frequencies) of light a molecule emits in passing from a higher to lower energy electronic state during about the first millisecond after absorbing a photon of light. Fluorescence wavelengths and emission intensity reflect the redistribution of energy in the molecule after light absorption. Fluorescence excitation spectroscopy reflects the efficiency with which a molecule converts absorbed energy into fluorescent emission as a function of the wavelength of the absorbed photons.

Phosphorescence Spectroscopy—an analytical technique which measures a range of wavelengths (or frequencies) of light a molecule emits in passing from a higher to lower energy electronic state on a time scale beyond the first millisecond after absorbing a photon of light. Phosphorescence wavelengths and emission intensity also reflect the redistribution of energy in the molecule after light absorption. Phosphorescence excitation spectra reflect the efficiency with which a molecule converts absorbed energy into phosphorescent emission as a function of the wavelength of the absorbed photons.

Principal Component Analysis (PCA)—this pattern recognition technique and the related technique of partial least squares analysis reduce the structure descriptors used to describe a training set of molecules to a smaller number of linear combinations of the original set of descriptors which are called principal components (PCs). The optimum number of principal components will yield the smallest standard error of prediction while capturing as much of the variance shown by the structural data as possible. (See generally, Kramer, R., *Chemometric Techniques for Quantitative Analysis*, Marcel Dekker, Inc., 1998).

Principal Component Linear Regression (PCLR)—a type of PCA useful for establishing a quantitative relationship between an endpoint and structure descriptors, for example, segmented spectral data and structural connectivity spectral data.

Comprehensive Descriptors for Structural and Statistical Analysis (CODESSA)—a set of various structural descriptors typically utilized in three dimensional quantitative structure-activity studies that includes constitutional descriptors, topological descriptors, geometrical descriptors, electrostatic descriptors, and quantum mechanical descriptors, all of which require knowledge of structure beforehand. (See, Tong et al., *J. Med. Chem.*, 39: 380-387, 1995 and Collantes et al., *J. Anal. Chem.*, 68: 2038-2043, 1996, both of which are incorporated herein by reference)

Auto-scaling—a method whereby the quantitative spectral information contained within each particular bin is compared for all compounds in the training set to yield an average value and a standard deviation. Then, for each bin comprising the structure descriptors of a given compound, the quantitative spectral information therein is expressed as a number of standard deviations above or below the average for each bin. Autoscaling equalizes the importance of inherently weak spectral signals falling within certain bins with the importance of inherently strong spectral signals falling within certain other bins in describing a set of spectrally derived structure descriptors. It may also equalize the importance of different types of spectral data in a composite of spectral data.

Fisher-weighting—a method whereby the quantitative spectral information in bins that are important for classifying the training set compounds into different endpoint groups, such as strong and medium binders to the estrogen receptor, are enhanced. For each bin, the variance of the quantitative spectral information between the endpoint groups is divided by the variance of the quantitative spectral information within the endpoint groups. The resulting dividend becomes a weighting factor that has a magnitude larger than one when a particular bin has an important role in distinguishing the endpoint groups. Each bin is multiplied by its weighting factor to yield structure descriptors that are more sensitive to subtle but significant spectral variations.

Leave-one-out (LOO) Cross-Validation—a method whereby each compound in the training set is systematically excluded from the data set, after which its endpoint value is predicted by the spectral data-activity relationship derived from the remaining compounds (See, Cramer et al., *Quant. Struct-Act. Relat.* 7: 18-25, 1998, incorporated herein by reference). Cross-validation is useful for judging the reliability of a spectral data-activity relationship, especially where a validation set of compounds is not available.

CoSCoSA (Comparative Structural Connectivity Spectral Analysis)—a spectral data-activity method based at least in part on detecting patterns in structural connectivity spectral data correlated with an endpoint property.

CoSA (Comparative Spectral Analysis)—a spectral data-activity method based at least in part on detecting patterns in unassigned spectral data correlated with an endpoint property.

CoSASA (Comparative Structurally Assigned Spectral Analysis)—a spectral data-activity method based at least in part on detecting patterns of spectral signal energies assigned to particular structural components of a structural moiety shared amongst a training set of molecules.

EXAMPLES

The following examples further illustrate the disclosed multidimensional (Q)SDAR methods. The methods utilize descriptors comprising spectral data that either contains information regarding the structural connections between components of structure responsible for particular spectral signals or is a combination of spectral data and a geometric measure of the relationship between the structural components responsible for particular spectral signals. These spectral structure descriptors may be used to model biological, chemical, and/or physical endpoints.

The disclosed spectral data-activity methods utilize a molecule's experimental and/or predicted spectral data, along with geometric information that is derived from the molecule's known or predicted structure(s) or is part of the spectral data, to provide molecular descriptors that uniquely reflect molecular shape and electrostatics. Spectral data, more particularly the energies of spectral signals, often depend on the local environment of the structural component (e.g. a particular atom, groups of atoms or bond within the structure) that is responsible for the signal. Thus, the energy of a spectral signal attributable to a particular structural component reflects the shape and/or electrostatic properties of the molecule in the vicinity of the component. A combination of spectral data and the geometric relationship between components of structure to which spectral signals of particular energies are attributable provides a useful three-dimensional description of a molecule. Combined spectral/geometric data may reflect through-bond and/or through-space relationships between structural components. Because multiple structures may give rise to similar three-dimensional relationships between components of structure exhibiting particular electrostatic properties, the methods are amenable to modeling structurally dissimilar molecules. Spectral data that also reflects a geometric relationship between the spectral signals is referred to hereinafter as "structural connectivity spectral data."

In some embodiments, individual signals in the spectral data (experimental or theoretical) of a molecule are assigned to components of molecular structure that give rise (or at least contribute) to the particular signal. Assigned spectral signals of a molecule are combined with geometric information derived from the structure of the molecule to provide structural connectivity spectral data descriptors for the molecule. These descriptors reflect the spatial relationship between structural components responsible for particular spectral signals. In other embodiments, the spectral data contains information regarding the spatial relationships between spectral signals and it is not necessary to assign individual signals in the spectral data to particular components of molecular structure.

In some embodiments, structural connectivity spectral data is measured directly by experiment. In other embodiments, the 1-D spectra of molecules are measured and used along with structural data to predict structural connectivity spectral data. In still other embodiments, the spectra of molecules are calculated (predicted) from their structures and used along with structural data to predict structural connectivity spectral data. Advantageously, predicted structural connectivity spectral data includes many types of spectral data that are difficult or impossible to measure experimentally. For example, experimental $^{13}C$—$^{13}C$ COSY spectra and $^{13}C$—$^{13}C$ distance spectra are rarely measured because they require samples of molecules that have been exhaustively labeled with $^{13}C$. Furthermore, it is currently impossible to experimentally measure NMR distance spectra, including $^{13}C$—$^{13}C$ distance spectra, where the separation between atoms exceeds about 5 Angstroms. On the other hand, $^{13}C$—$^{13}C$ COSY spectra and $^{13}C$—$^{13}C$ distance spectra are easily constructed from experimental and/or predicted $^{13}C$ NMR data and information regarding the 3-D structure of a molecule obtained, for example, from X-ray crystallographic data, NMR data or molecular calculations. Structural connectivity spectral data can offer accurate descriptions of the electronic and steric characteristics of molecules without requiring computationally intensive quantum mechanical calculations. In some embodiments, time-dependent structural data is used to produce time-dependent structural connectivity spectral data that may be used to model the inherent flexibility of molecular structures. In more particular embodiments, time-dependent structural data is obtained from molecular dynamics calculations.

In another aspect, the disclosure provides methods for predicting properties of molecule. In one embodiment, a training set of molecules exhibiting a range of endpoint values is selected and structural connectivity spectral data is obtained for the molecules of the training set. A pattern of structural connectivity spectral data that is correlated with the endpoint values exhibited by the training set is detected. The endpoint value of a test compound is predicted by comparing the pattern derived from the training set to the structural connectivity spectral data for a test compound. In particular embodiments, the endpoint is a biological property. In other particular embodiments, the endpoint is a qualitative endpoint, a quantitative endpoint, or a combination of two or more endpoints, either qualitative or quantitative. Where the endpoint is a quantitative endpoint, the pattern derived from the training set is correlated with the magnitude of the endpoint.

In yet another aspect, the disclosure includes computer readable media having stored thereon, the instructions for carrying out the various embodiments of the methods.

Example 1

Comparative Structural Connectivity Spectra Analysis (CoSCoSA) Models of Steroid Binding to the Corticosteroid Binding Globulin Many different types of models have been developed to predict the binding activity for the compound-receptor system of the corticosterone binding globulin (Mickelson et al., "Steroid-protein Interactions: Human corticosteroid binding globulin, some physiochemical properties and binding specificity," *Biochemistry* 20: 6211-6218 (1981)). These corticosteroid binding globulin models include the standard quantitative structure-activity relationship (QSAR) (Good et al., "Structure-activity Relationships from Molecular Similarity Matrices," *J. Med. Chem.*, 36: 433-438 (1993)), the hybrid electrotopological state (E-state) model (Kellogg et al., "E-state Fields: Applications to 3D QSAR, *J. Comput.-Aided Mol. Design*, 10: 513-520 (1996)), the self-organizing map (SOM) (Polanski, "The Receptor-like Neural Network for Modeling Corticosteroid and Testosterone Binding Globulins," *J. Chem. Inf. Comput. Sci.*, 37: 553-561 (1997)), and the combination QSAR E-state models (De Gregorio et al. "QSAR Modeling with Electrotopological State Indices: Corticosteroids," *J. Comput.-Aided Mol. Design.*, 12, 557-561 (1988)). Simulated $^{13}C$ NMR spectrometric data have also been used as descriptors to produce reliable quantitative spectrometric data-activity relationship (QSDAR) models of the corticosterone binding globulin (Beger and Wilkes, "Developing $^{13}C$ NMR Quantitative Spectrometric Data-Activity Relationship (QSDAR) Models of Steroid Binding to the Corticosteroid Binding Globulin," *J. Comput.-Aided Mol. Design.*, 15: 659-669, (2001). The model using simulated $^{13}C$ NMR data yielded higher cross-validated correlations than were seen with comparative molecular field analysis (CoMFA) methods. The presently disclosed methods, however, provide unexpectedly superior results over prior SDAR methods.

Table 1 shows the core steroid structure, substitution pattern, and experimental corticosteroid binding affinity data for a training set of compounds. Each compound in Table 1 had its $^{13}C$ NMR spectra simulated using the ACD Labs CNMR predictor software, version 4.0 (ACD Labs, Toronto, Canada). For CoSCoSA modeling, predicted $^{13}C$ NMR spectra were used. Predicted chemical shifts are not necessary to build the QSDAR models, but it saves time and money. Furthermore, predicted $^{13}C$ NMR data is independent of the solvent used, thereby reducing errors associated with experimental data. The CoSCoSA modeling, LOO cross-validation, and prediction processes were completely computerized in this example.

TABLE 1

Structures of corticosteroids used in QSDAR models of corticosteroid binding globulin data.

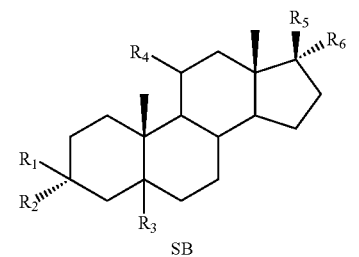
SB

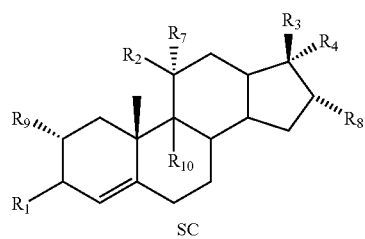
SC

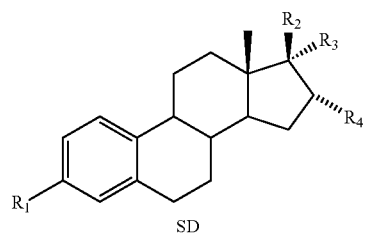
SD

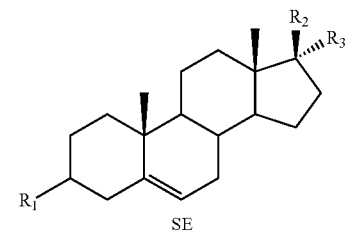
SE

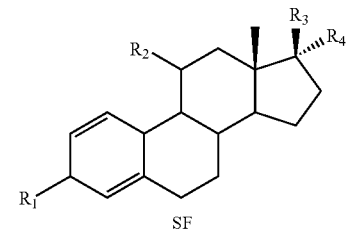
SF

| # | Structure | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|---|
| 1 | SB | OH | H | H | H | OH | H | | | | |
| 2 | SE | OH | OH | H | | | | | | | |
| 3 | SC | =O | H | =O | | | | H | H | H | H |
| 4 | SB | H | OH | H | H | =O | | | | | |
| 5 | SC | =O | OH | COCH$_2$OH | H | | | H | H | H | H |
| 6 | SC | =O | OH | COCH$_2$OH | OH | | | H | H | H | H |
| 7 | SC | =O | =O | COCH$_2$OH | OH | | | H | H | H | H |
| 8 | SE | OH | =O | | | | | | | | |
| 9 | SC | =O | H | COCH$_2$OH | H | | | H | H | H | H |
| 10 | SC | =O | H | COCH$_2$OH | OH | | | H | H | H | H |
| 11 | SB | =O | | H | H | OH | H | | | | |
| 12 | SD | OH | OH | H | H | | | | | | |
| 13 | SD | OH | OH | H | OH | | | | | | |
| 14 | SD | OH | =O | | H | | | | | | |
| 15 | SB | H | OH | H | H | =O | | | | | |

TABLE 1-continued

Structures of corticosteroids used in QSDAR models of corticosteroid binding globulin data.

| 16 | SE | OH | COMe | H | | | | | |
|---|---|---|---|---|---|---|---|---|---|
| 17 | SE | OH | COMe | OH | | | | | |
| 18 | SC | =O | H | COMe | H | H | H | H | H |
| 19 | SC | =O | H | COMe | OH | H | H | H | H |
| 20 | SC | =O | H | OH | H | H | H | H | H |
| 21 | SF | =O | OH | COCH$_2$OH | OH | | | | |
| 22 | SC | =O | OH | COCH$_2$OCOMe | | H | H | H | H |
| 23 | SC | =O | =O | COMe | H | | H | H | H |
| 24 | SC | =O | H | COCH$_2$OH | H | OH | H | H | H |
| 25[b] | SC | =O | H | OH | H | H | H | H | H |
| 26 | SC | =O | H | COMe | OH | H | OH | H | H |
| 27 | SC | =O | H | COMe | H | H | Me | H | H |
| 28[a] | SC | =O | H | COMe | H | H | H | H | H |
| 29 | SC | =O | OH | COCH$_2$OH | OH | H | H | Me | H |
| 30 | SC | =O | OH | COCH$_2$OH | OH | H | H | Me | F |

[a] H (hydrogen) instead of Me at C$_{10}$ on steroid skeleton.

FIG. 1 shows a diagram outlining four different embodiments of the CoSCoSA procedures used to produce predictive models of corticosteroid globulin binding affinity based on the training set structures and endpoint data. The structures of the molecules listed in Table 1 were used to predict ID $^{13}$C NMR spectra for each of the molecules. The predicted NMR spectra were calculated by a substructure similarity technique called HOSE (Bremser, "HOSE—a Novel Substructure Code," *Anal. Chim. Acta.*, 103: 355-365(1978)), which determines the chemical shift of a carbon based on empirically determined chemical shifts exhibited by carbons that are part of similar sub-structural components in other molecules. Therefore, the errors produced in the simulated NMR spectra were propagated through the similar structures found in the training set of the QSDAR models. This conveniently reduced the effective error when using the training set to predict unknown sample affinities for compound spectra predicted using the same HOSE routine.

Figure 2:
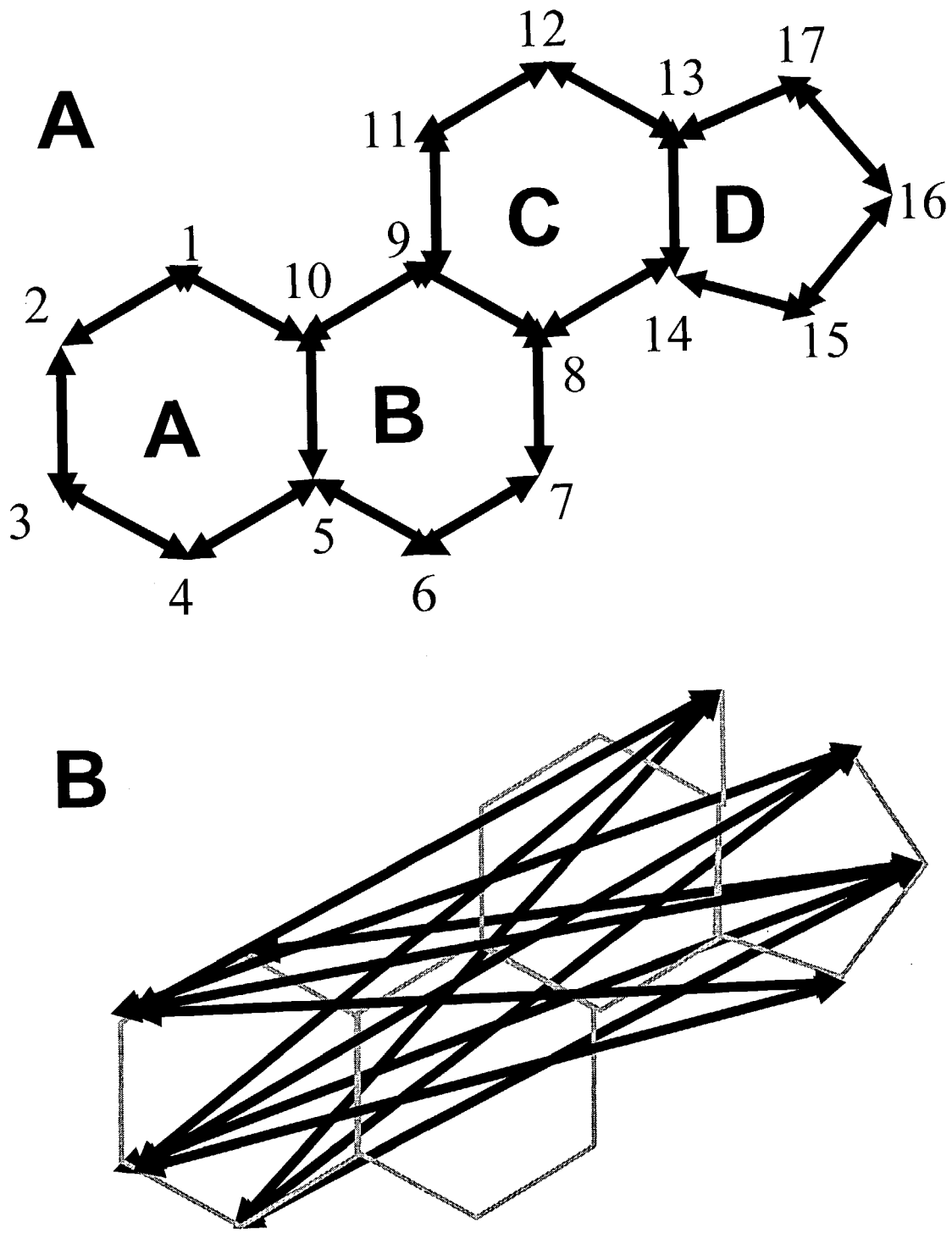
FIG. 2A is a diagram showing a number of carbon-to-carbon through-bond connections used to predict 2D $^{13}C$—$^{13}C$ COSY spectra for estrogen receptor modeling.
FIG. 2B is a diagram showing a number of carbon-to-carbon through-space connections used to predict 2D $^{13}C$—$^{13}C$ distance spectra for estrogen receptor modeling.

Structurally assigned $^{13}$C NMR spectra were then used to produce predicted 2D $^{13}$C—$^{13}$C COSY and theoretical 2D $^{13}$C—$^{13}$C distance spectra. The arrows in FIG. 2A show the through-bond neighboring carbon-to-carbon connectivities of a steroid backbone molecule without any side chains. These through bond carbon to carbon connectivities were used to simulate a 2D $^{13}$C—$^{13}$C COSY spectrum of the steroid compounds. The arrows in FIG. 2B show the through-space carbon to carbon connectivities in a steroid ring system having interatomic distances greater than 6.9 Angstroms. These through-space carbon-to-carbon connections within the steroid ring system and any other through-space carbon-to-carbon distance connectivities (e.g. between ring system carbons and side chain carbons and between side chain carbons) that were greater than 6.9 Angstroms were used to produce a theoretical 2D $^{13}$C—$^{13}$C distance connectivity spectra that exhibited cross-peaks when two carbons were greater than 6.9 Angstroms apart. The 2D $^{13}$C—$^{13}$C COSY and 2D $^{13}$C—$^{13}$C distance connectivity spectra are symmetrical across the diagonal, and for modeling purposes only half of each individual spectrum was used. One-dimensional $^{13}$C NMR spectra were not used in the CoSCoSA models because the ID chemical shifts are highly correlated to all the cross-peaks that appear in the COSY and distance spectra and thus do not present any new information.

The resolution of the 2D spectra was adjusted to around 2.0 ppm in both dimensions to ensure more of the spectral data bins are populated by signals prior to statistical analysis, thereby reducing the effects of uncertainties in the simulated spectra. The 2D $^{13}$C—$^{13}$C NMR spectra were saved as two-dimensional bins under the peaks within a certain spectral range and normalized to an integer. For example, a single carbon-to-carbon connectivity was assigned an area of 100, two carbon to carbon connectivities in a bin were given an area of 200, and so forth. This was done so that all the carbon-to-carbon connectivities would have similar signal-to-noise ratios.

Referring again to FIG. 1, four alternative methods of using the predicted structural connectivity spectral data to produce a CoSCoSA model are presented. Steps labeled "A" represent the process of first reducing the 2D $^{13}$C—$^{13}$C COSY spectral data (i.e. the through-bond connectivities) to PCs and then using the PCs for multiple linear regression to produce a CoSCoSA model from the 2D $^{13}$C—$^{13}$C COSY data. Steps labeled "B" represent a process of reducing the 2D $^{13}$C—$^{13}$C distance connectivity data (i.e. the through-space connectivities) to PCs and then using these PCs for multiple linear regression to produce a CoSCoSA model from the 2D $^{13}$C—$^{13}$C distance connectivity data. Steps labeled "C" represent a procedure where the PCs from the 2D $^{13}$C—$^{13}$C COSY and the 2D $^{13}$C—$^{13}$C distance connectivity data are combined and then used to produce a combined through-bond and through-space CoSCoSA model. Steps labeled "D" represent a procedure where the 2D $^{13}$C—$^{13}$C COSY data and the 2D $^{13}$C—$^{13}$C distance connectivity data are first combined and then the combined data set is reduced to PCs before multiple linear regression is performed on the PCs to produce a different combined through-bond and through-space CoSCoSA model of binding affinity.

All statistical analysis, including calculation of PCs and linear regression analysis was performed by Statistica software versions 5.5 and 6.0 (Statistica, StatSoft, Tulsa, Okla.). The CoSCoSA QSDAR models were produced by evaluating the connectivity bins with partial least squares (PLS) forward multiple regression analysis using only the most correlated PCs from both the 2D $^{13}$C—$^{13}$C COSY and 2D $^{13}$C—$^{13}$C distance connectivity spectra. The F-test for many of the models continued to rise until the number of components in the model equaled the number of compounds in the training set. For this reason, the number of PC's used in the CoSCoSA models was limited to either 3 or 8.

The analysis of each $^{13}$C NMR QSDAR model was done by the leave-one-out (LOO) cross-validation procedure where each compound is systematically excluded from the training set and its binding activity is predicted by the model (see, for example, Cramer et al., "Cross-validation, Bootstrapping, and Partial Least Squares Compared with Multiple Regression in Conventional QSAR studies," *Quant. Struct.-Act.*

*Relat.*, 7: 18-25 (1988)). The cross-validated $r^2$ (termed $q^2$) can be derived from $q^2=1-(PRESS)/SD$. Where PRESS is the sum of the differences between the actual and predicted activity data for each molecule during LOO cross-validation, and SD is the sum of the squared deviations between the measured and mean activities of each molecule in the training set. It is believed that $q^2$ is a more valid measure than $r^2$ for assessing the reliability of a mathematical model intended for predictive applications.

Table 2 contains a comparison of the model performance parameters n, $r^2$, $q^2$, and number of components for the QSAR, HE-state/E-state, E-state, SOM, combination QSAR/E-state, CoSASA, and CoSA models and the four CoSCoSA models outlined in FIG. 1. All four CoSCoSA models with 8 PCs have a strong correlation ($r^2$) and cross-validated variance ($q^2$), and are favorable when compared to the previous published models of binding to the corticosteroid binding globulin. The statistical results were further tested and validated by randomizing the binding activity data and the best statistical correlation occurred using actual binding data.

TABLE 2

Model performance parameters n, $r^2$, $q^2$, and number of components.

| model | n | $r^2$ | $q^2$ | Components |
|---|---|---|---|---|
| QSAR (2) | 31 | .72 | .68[a] | 3 (PCs) |
| HE state/E-state (3) | 31 | .98[a]/.96[b] | .80[a]/.76[b] | 3[a](PCs)/5[b] (PCs) |
| E-state (3) | 31 | .96[a]/.96[b] | .79[a]/.67[b] | 3[a](PCs)/4[b] (PCs) |
| SOM (4) | 31 | .85 | — | 3 (PCs) |
| QSAR/E-state (5) | 30 | .82 | .78 | 3 (atoms) |
| CoSASA (6) | 30 | .80 | .73 | 3 (atoms) |
| CoSA (6) | 30 | .80 | .78 | 3 (bins) |
| CoSCoSA (COSY) | 30 | .84/.93 | .74/.88 | 3 (PCs)/8 (PCs) |
| CoSCoSA (distance) | 30 | .55/.89 | .30/.72 | 3 (PCs)/8 (PCs) |
| CoSCoSA (COSY + distance) | 30 | .84/.96 | .74/.92 | 3 (PCs)/8 (PCs) |
| CoSCoSA (3D[c]) | 30 | .78/.92 | .68/.81 | 3 (PCs)/8 (PCs) |

[a]1.0 Angstrom models,
[b]2.0 Angstrom models,
[c]3D is combined COSY and distance data before PC extraction.

Figure 3:
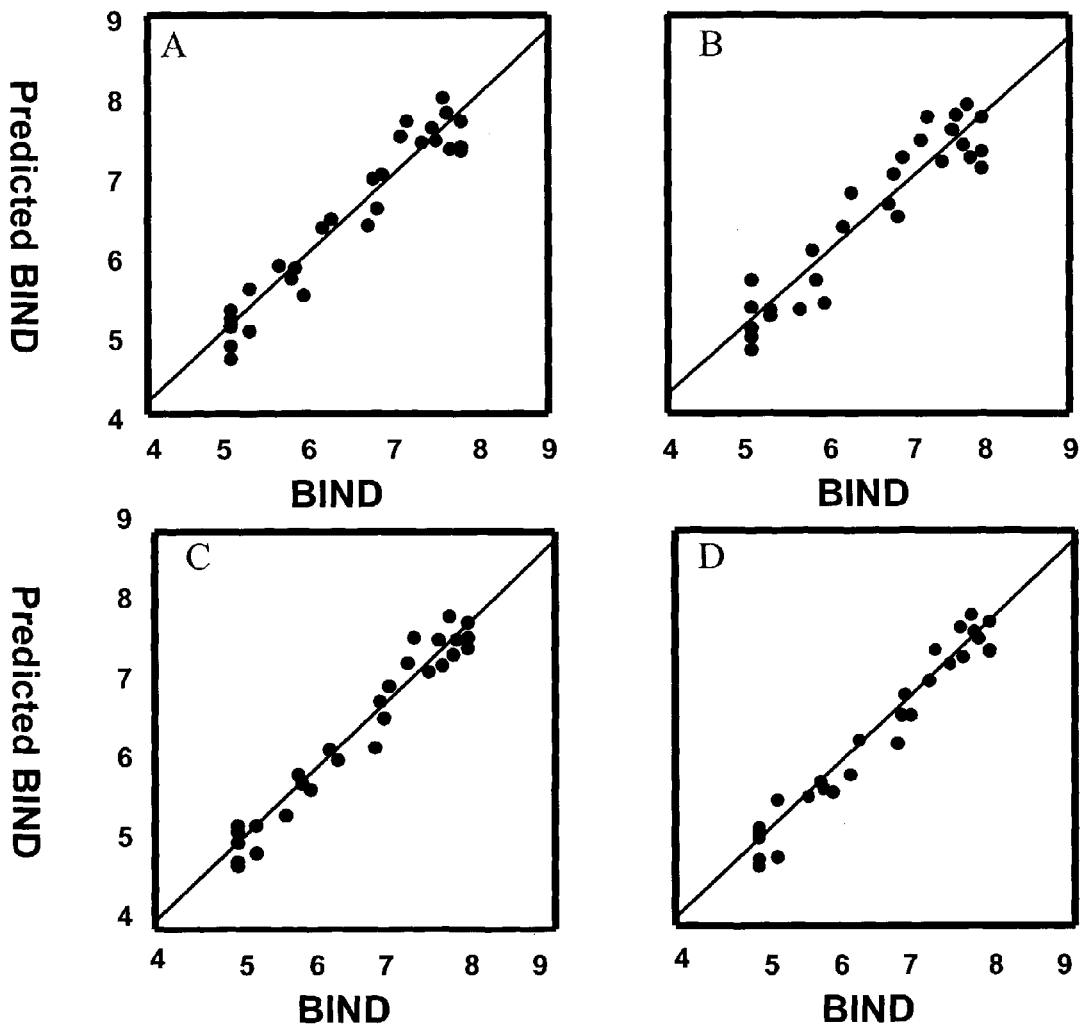
FIG. 3A is a graph of the predicted estrogen receptor binding affinity versus experimental binding affinity for a model of estrogen receptor binding derived from theoretical $^{13}C$—$^{13}C$ COSY spectral data.
FIG. 3B is a graph of the predicted estrogen receptor binding affinity versus experimental binding affinity for a model of estrogen receptor binding derived from theoretical $^{13}C$—$^{13}C$ distance spectral data for carbon to carbon separations of greater than 6.9 Angstroms.
FIG. 3C is a graph of the predicted estrogen receptor binding affinity versus experimental binding affinity for a model of estrogen receptor binding derived from a combination of PCs extracted from $^{13}C$—$^{13}C$ COSY and $^{13}C$—$^{13}C$ distance spectral data (>6.9 Angstroms).
FIG. 3D is a graph of the predicted estrogen receptor binding affinity versus experimental binding affinity for a model of estrogen receptor binding derived from a combination of $^{13}C$—$^{13}C$ COSY and $^{13}C$—$^{13}C$ distance spectral data before PCs are extracted from the combined data.

FIG. 3A is a plot of the predicted binding versus experimental binding for the CoSCoSA model based on $^{13}C-^{13}C$ COSY data using 2.0 ppm square bins. A model based on 8 PC's had an explained correlation ($r^2$) of 0.93 and a cross-validated variance ($q^2$) of 0.88, indicating self-consistency and excellent predictive capability. FIG. 3B is a plot of the predicted binding versus experimental binding for the CoSCoSA 2.0 ppm resolution model based on $^{13}C-^{13}C$ distance spectral data for carbons separated by greater than 6.9 Angstroms. Using 8 PCs the explained correlation ($r^2$) of this model is 0.89 and the cross-validated variance ($q^2$) is 0.72, which again indicates self-consistency and excellent predictive capability. FIG. 3C is a plot of the predicted binding versus experimental binding for the CoSCoSA 2.0 ppm resolution model based on the combined $^{13}C-^{13}C$ COSY and $^{13}C-^{13}C$ distance connectivity PCs. The explained correlation ($r^2$) of this model is 0.96 and the cross-validated variance ($q^2$) of this model is 0.92, indicating excellent self-consistency and predictive capability. FIG. 3D is a plot of the predicted binding versus experimental binding for a CoSCoSA 2.0 ppm resolution model based on the combined $^{13}C-^{13}C$ COSY and $^{13}C-^{13}C$ distance connectivity spectral data before principal component extraction. The explained correlation ($r^2$) of this model is 0.92 and the cross-validated variance ($q^2$) of this model is 0.81, again indicating self-consistency and high predictive capability.

All four CoSCoSA models based on 8 PCs have a $q^2$ greater than the 0.68 seen for the QSAR model. Three of the four CoSCoSA models based on 3 PCs have a $q^2$ greater than the 0.68 seen for the QSAR model. The only CoSCoSA model that did not have a $q^2$ greater than 0.68 was the $^{13}C-^{13}C$ distance connectivity model based on only 3 PCs. The HE-state and E-state models have a greater $r^2$ than all the QSDAR models but these models are very computational-intensive with many distance formulas used for every point in the grid. Still, all the 2.0 ppm resolution CoSCoSA models based on 8 PCs have explained variance ($r^2$) greater than 0.89 and a cross-validated variance ($q^2$) greater than of 0.72. All of the CoSCoSA models with 8 PCs have a predictability that is much better or comparable to the predictability for QSAR, CoSA, CoSASA, HE-state/E-state, and E-state models. The reason why CoSCoSA models based on 8 PCs are compared to other models based only on 3 or 4 principal components is that the CoSCoSA models are "digital" in nature and the other QSAR, HE-states, and E-states models are in "analog" format. Digital information needs more components to present the same information (10 binary components to represent a number less than 999) as analog electronics (3 variable components to represent a number less than 999), but the resulting information is presented with a higher signal to noise value. Although the CoSCoSA models reflect essentially the same electrostatic information as reflected in QSAR or E-states models, the CoSCoSA models have a better signal to noise ratio (predictability) than other models when more principal components are used.

An explanation for the observation that the cross-validated variances of the CoSCoSA QSDAR models were as good as the other models is that even simulated NMR spectral data are more accurate than the errors introduced by solvent effects, partial charges, dielectrics, and structural conformations used during the calculation of electrostatic potentials. All of these assumptions and approximations are likely to produce significant errors. Predicted $^{13}C$ NMR spectral data takes into account all structural conformations, and complete solvent effects, to produce a chemical shift (quantum mechanical energy) that represents the average structural environment for every carbon atom in the molecule.

The CoSA QSDAR models based on $^{13}C$ NMR data began with only 256 spectral bins, a number then reduced to 94 spectral bins when all the columns with only zeroes or with only one non-zero entry were removed. The 2.0 ppm CoSCoSA models began with 6441 two-dimensional bins (each 2.0 ppm by 2.0 ppm), a number then reduced to 271 for the $^{13}C-^{13}C$ COSY data and 322 for the $^{13}C-^{13}C$ distance connectivity data when all the columns with only zeroes were removed. Such results indicate that less than 5% of the available 2D connectivity space is used with this training set and the 2 ppm resolution bin size. Since less than 5% of the available 2D chemical shift "space" is used, it is believed that this procedure may be used to effectively build reliable models of very large sets of non-congeneric compounds for a specific endpoint.

The effect of combining all bins with only one "hit" in the bin (i.e. a spectral signal falling within a bin's defined range(s)) to the nearest bin with a "hit" was investigated. Bins with one "hit" were combined with the closest bin with a "hit." When multiple bins with "hits" were equally close to a bin with one "hit", the bin with one "hit" was consistently moved the to the bin with least number of "hits". When all the bins with one "hit" were combined with their nearest neighboring bin with at least a "hit", the 2 ppm $^{13}C-^{13}C$ COSY had 93 of the 271 bins removed. When all the bins with one "hit" were combined with the nearest neighboring bin with at least a "hit", the 2 ppm $^{13}C$—$^{13}C$ distance connectivity data had 128 of the 322 bins removed. Using the $^{13}C$—$^{13}C$ COSY data with no bins having only one "hit" the $r^2$ of the CoSCoSA model increased from 0.93 to 0.94 and $q^2$ increased from 0.88 to 0.89. For the $^{13}C$—$^{13}C$ distance connectivity data with no bins having only one "hit", the $r^2$ of the model increased from 0.89 to 0.91 and $q^2$ increased from 0.79 to 0.81. Using a combination of PCs extracted individually from both the edited $^{13}C$—$^{13}C$ COSY and the edited $^{13}C$—$^{13}C$ distance connectivity data to produce a model where $r^2$ decreased from 0.96 to 0.95 and $q^2$ remained at 0.90. Combining the edited $^{13}C$—$^{13}C$ COSY and $^{13}C$—$^{13}C$ distance data before the extraction of PCs, increased $r^2$ from 0.92 to 0.93 and increased $q^2$ from 0.81 to 0.84.

The effect of altering the bin size was investigated by increasing the bin size to 3.0 ppm square. The 3.0 ppm CoSCoSA models started with 2926 two-dimensional bins, a number then reduced to 199 for the $^{13}C$—$^{13}C$ COSY data and 253 for the $^{13}C$—$^{13}C$ distance connectivity data when all the columns with only zeroes were removed. For the model based on $^{13}C$—$^{13}C$ COSY data, the $r^2$ decreased from 0.93 to 0.87 and $q^2$ decreased from 0.88 to 0.79 in going from 2.0 ppm bins to 3.0 ppm bins. For the model based on $^{13}C$—$^{13}C$ distance connectivity data, the $r^2$ increased from 0.89 to 0.90 and $q^2$ increased from 0.72 to 0.74. For the model based on the combined $^{13}C$—$^{13}C$ COSY and $^{13}C$—$^{13}C$ distance connectivity PCs, the $r^2$ decreased from 0.96 to 0.90 and $q^2$ decreased from 0.96 to 0.74. For the model based on the combined $^{13}C$—$^{13}C$ COSY and $^{13}C$—$^{13}C$ distance connectivity data before extraction of principal components, the $r^2$ was unchanged at 0.92 and $q^2$ increased from 0.81 to 0.84.

The effect of using different distance ranges for the $^{13}C$—$^{13}C$ distance connectivity spectral CoSCoSA models was also investigated. Instead of using all distance connectivities greater than 6.9 Angstroms the same set of atom to atom distances was used for all the compounds. This meant using the distance connectivity set from the smallest compounds (no chains off of the steroids) for all the compounds. The smallest compounds had 26 distance connectivity interactions greater than 6.9 Angstroms, 13 on each side of the 2D $^{13}C$—$^{13}C$ distance connectivity spectral matrix. When using all distance connectivity interactions greater than 6.9 Angstroms, the number of interactions varied for each compound. When only the $^{13}C$—$^{13}C$ distance data with the 13 defined interactions for each compound was used to build a CoSCoSA model, the $r^2$ of 0.89 did not change and the $q^2$ decreased from 0.79 to 0.77. When the new $^{13}C$—$^{13}C$ distance connectivity PCs based on the same 13 distance connectivities for each steroid compound were used with the original $^{13}C$—$^{13}C$ COSY PCs to build a CoSCoSA model, $r^2$ decreased from 0.96 to 0.95 and the $q^2$ decreased from 0.90 to 0.89. Using the original $^{13}C$—$^{13}C$ COSY data and the 13 component $^{13}C$—$^{13}C$ distance data combined before extraction of PCs the $r^2$ increased from 0.92 to 0.95 and $q^2$ increased from 0.81 to 0.93.

The CoSCoSA models in this example take into account the average uncertainty in the predicted $^{13}C$ NMR data. The models therefore reduce the information content of the spectrum by reducing the number of spectral bins and losing the shape of the chemical shift peak. Still, the CoSCoSA models retained enough information by increasing the number of chemical shifts in many of the spectral bins to produce reliable statistical models of binding to the corticosteroid binding globulin. The NMR chemical shift peak has information about atom adjacency, solvent effects, and average structural conformation but the shape of the peak is greatly affected by shimming and temperature dependent dynamics. Inclusion of average uncertainty into the simulated $^{13}C$ NMR data does not appear to affect the ability of simulated $^{13}C$ NMR data to be used to model the binding affinity of structurally similar compounds to a receptor.

The 2D $^{13}C$—$^{13}C$ COSY nearest neighbor connectivity spectral data should be important for almost any molecular property or binding affinity. Between the CoSCoSA models, those based on the 2D $^{13}C$—$^{13}C$ COSY data had a higher $r^2$ and $q^2$ than those based on the $^{13}C$—$^{13}C$ distance connectivity data. The $^{13}C$—$^{13}C$ distance connectivity data will become more important when one or more a distance separated structural features are required for a certain molecular property, for example, for large molecule binding to a receptor. This is the case for steroids binding to the corticosteroid binding globulin where regions around position 3 and 17 of the steroid, separated by approximately 8.5 Angstroms, are important for binding.

The CoSCoSA models that combined the $^{13}C$—$^{13}C$ COSY and $^{13}C$—$^{13}C$ distance connectivity PCs together produced the models with the highest $r^2$ and $q^2$. The combined $^{13}C$—$^{13}C$ COSY and $^{13}C$—$^{13}C$ distance connectivity PCs models were better than the models where the $^{13}C$—$^{13}C$ COSY and $^{13}C$—$^{13}C$ distance data were combined and then used to extract PCs, because there were twice as many PCs available from which to build a model with the separated connectivity data.

In CoSCoSA modeling the choice of the number and size of bins is a factor affecting the reliability of the model derived. Too large a bin size inappropriately lumps distinct spectral information into the same category and too small a bin size suffers from false distinctions based on reduced average bin occupancy values that adversely affect the statistics needed to identify and confirm the pattern. If one uses a huge number of bins, the results will be a model with excellent $r^2$ and poor $q^2$. For modeling of corticosteroid globulin binding data, bins of between about 2 ppm and 3 ppm bins seem to work best. However, in other instances, bins having widths of from about 0.1 ppm to about 10 ppm, such as from 0.5 ppm to 5.0 ppm or from 1.0 ppm to 3.0 ppm. As stated before, each dimension need not be separated into bins of identical width, nor does any particular dimension have to have bins of equal width across its range.

It appears that in the case of corticosteroid globulin binding affinity, 2 ppm resolution bins work better for the COSY data, and 3 ppm resolution bins seemed to work slightly better for the distance connectivity data. This makes sense because there are more COSY nearest neighbor connections than there are distance connections greater than 6.9 Angstroms per molecule. A smaller bin size could be used for the COSY data and still produce reliable statistical models because more bins are populated. The investigation into moving all the bins with one "hit" in them to the nearest bin with a "hit" had an $r^2$ and a $q^2$ that was only slightly improved over the original 2 ppm resolution CoSCoSA models. Changing the cutoff distance from any distance over 6.9 Angstroms to only the same 13 distance connections from the smallest molecules produced only very small changes in $r^2$ and $q^2$.

Overall, the demonstrated accuracy of the $^{13}C$ NMR QSDAR model predictions shows that the CoSCoSA models effectively combine quantum mechanical information from the chemical shifts with nearest neighbor and internal distance connectivity information and provide reliable models of steroids binding to corticosteroid binding globulin. Incorporation of through-bond and through-space molecular structure connectivity to produce 2D $^{13}C$—$^{13}C$ spectral data was shown to produce CoSCoSA models that are much more accurate and reliable than QSAR or E-state models based on separate calculations for electrostatics and steric interactions. The cross-validated variance of CoSCoSA models based on simulated $^{13}$C NMR data should improve as the errors introduced by the simulation of the $^{13}$C NMR data are further reduced by improved spectral simulation programs. Optimizing the bin size, the distance cutoffs, and the number of distance connectivity spectra used may provide even better CoSCoSA models of corticosteroid globulin binding activity. For example, including NMR data for types of atoms other than carbon (e.g. hydrogen and oxygen) should improve the models.

Example 2

Comparative Structural Connectivity Spectra Analysis (CoSCoSA) Modeling of AhR Binding Affinity of Polychlorinated Dibenzodioxins, Dibenzofurans, and Biphenyls Polychlorinated dibenzo-p-dioxins (PCDDs), dibenzofurans (PCDFs), and biphenyls (PCBs) are industrial compounds or byproducts that are widely distributed in the environment. They are known toxicants having a common receptor-mediated mechanism of action (see, for example, Safe, "Polychlorinated Biphenyls (PCBs), Dibenzo-p-dioxins (PCDDs), Dibenzofurans (PCDFs), and Related Compounds: Environmental and Mechanistic Considerations which Support the Development of Toxic Equivalency Factors (TEFs)," *Crit. Rev. Toxicol.* 21: 50-88, 1990). Some polychlorinated aromatic compounds cause toxic effects after binding to an intracellular cytosolic receptor called the aryl hydrocarbon receptor (AhR) (see, for example, Bhandiera et al., "Polychlorinated Dibenzofurans (PCDFs): Effects of Structure on Binding to the 2,3,7,8-TDDD cytosolic receptor protein, AHH Induction and Toxicity," *Toxicology*, 32:131-144, 1984). Thymic atrophy, weight loss, immunotoxicity, acute lethality, and induction of cytochrome P4501A1 have all been correlated with the binding affinity of PCDDs, PCDFs, and PCBs to the aryl hydrocarbon receptor, AhR (see, for example, Mason et al., "Polychlorinated Dibenzo-p-dioxins: Correlation Between in Vitro and in Vivo Structure-activity Relationships," *Toxicology*, 37:1-12, 1985). This receptor controls the induction of the hepatic cytochrome P4501A1 and associated aryl hydrocarbon hydroxylase and 7-ethoxyresosufin O-deethylase activities (see, for example, Safe, "Polychlorinated Biphenyls (PCBs), Dibenzo-p-dioxins (PCDDs), Dibenzofurans (PCDFs), and Related Compounds: Environmental and Mechanistic Considerations which Support the Development of Toxic Equivalency Factors (TEFs)," *Crit. Rev. Toxicol.* 21: 50-88, 1990). Therefore, an important step in predicting the toxicity of PCDDs, PCDFs, and PCBs is being able to estimate each of their binding affinities to the AhR.

Most QSAR and QSDAR attempts to produce a single, predictive model across multiple chemical classes have met with limited success. In the case of PCDDs, PCDFs, and PCBs, this challenge seems to be further aggravated by the great dependency of each molecule's AhR binding activity on its chlorination sites and on the way in which its molecular backbone conformation affects the spatial locations of the chlorine atoms. Estimation of molecular conformation for QSAR models typically uses energy minimized structures rather than weighted average structural conformations. The latter arguably reflect more accurately the actual molecular characteristics. These factors explain why conventional QSAR models based on a mixture of PCDD, PCDF, and PCB congers have not succeeded well (see, for example, Mekemyan et al., "A QSAR Evaluation of Ah Receptor Binding of Halogenated Aromatic Xenobiotics, *Environ. Health Perspect*, 104:1302-1310, 1996). A QSDAR CoSA model for PCDD, PCDF, and PCB congeners was significantly robust with an $r^2$ of 0.85 and a $q^2$ of 0.71 (Beger and Wilkes, "Models of Polychlorinated Dibenzodioxins, Dibenzofurans, and Biphenyls Binding Affinity to the Aryl Hydrocarbon Receptor Developed Using $^{13}$C NMR Data. *J. Chem. Int. Comput. Sci.*, 15: 659-669, 2001), but it was believed that better results could be obtained if structural information was added to the CoSA models. CoSASA modeling of PCDD, PCDF, and PCB binding to the AhR, in fact, was not successful (Beger and Wilkes, undisclosed results).

In this example, the combined structural/spectral information present in 2D $^{13}$C—$^{13}$C COSY spectra and 2D $^{13}$C—$^{13}$C distance spectra are used as descriptors in a CoSCoSA model of the AhR binding affinities of PCDD, PCDF, and PCB compounds. This example demonstrates that structural connectivity information combined with $^{13}$C NMR spectra in the form of through-bond and through-space distance information can be used to produce a reliable, quantitative spectrometric data-activity relationship (QSDAR) model of PCDFs, PCDDs, and PCBs binding to the AhR. The models are sufficiently reliable to enable comparison of the detected pattern of 2D spectral data associated with the biological activity to similar spectral data for a test compound to determine whether the test compound is predicted to exhibit the biological activity.

The 2D $^{13}$C—$^{13}$C COSY spectra that contain through-bond connectivity patterns were produced by using the structurally assigned predicted spectra and adding the nearest neighbor information as cross peaks. In principal, 2D $^{13}$C—$^{13}$C COSY are not explicitly run because small molecules are rarely fully $^{13}$C labeled. Even if the molecules were fully labeled, the $^{13}$C through-bond connectivities usually are obtained directly from other 3D or 4D NMR experiments like HCCH or indirectly by combining the information from $^1$H—$^2$H COSY with $^{13}$C—$^1$H HMQC and HMBC NMR experiments (see, for example, Bax and Summers, "1H and 13C Assignments from sensitivity-enhanced detection of heteronuclear multiple-bond connectivity by 2D multiple quantum NMR," *J. Am. Chem. Soc.*, 108:2093-2094, 1986). The 2D $^{13}$C—$^{13}$C distance spectra contain through-space connectivity spectral patterns that were produced by using the structurally assigned predicted spectra and selecting a distance range for nucleus to nucleus distance (r).

Advantageously, the through-space and through-bond connectivities used to produce descriptors may be tailored to specific pharmacophores within the structure of a molecule. For example, 2,3,7,8-tetrachlorodioxin is a strong binder in AhR and the distance between carbons at positions 2 and 8 is 7.0 Angstroms, 2,3,7,8-tetrachlorofuran is also a strong binder to AhR and the distance between carbons at positions 2 and 8 is 6.76 Angstroms. Thus, in this example, an inter-carbon distance range of 5.0 to 7.2 Angstroms was selected for the $^{13}$C—$^{13}$C distance data. Presently, there are no NMR experiments that directly record structural distance information for interactions occurring between structural components that are greater than 5 Angstroms apart.

TABLE 3

| # | Compound | Experimental Log $EC_{50}$ | Predicted Log $EC_{50}$ |
|---|----------|---------------------------|-------------------------|
| 1 | 1-Cl-dibenzofuran | −5.53 | −6.14 |
| 2 | 2,8-diCl-dibenzofuran | −6.05 | −5.75 |

TABLE 3-continued

| # | Compound | Experimental Log EC$_{50}$ | Predicted Log EC$_{50}$ |
|---|---|---|---|
| 3 | 2,3,7-triCl-dibenzofuran | −8.10 | −7.93 |
| 4 | 2,3,8-triCl-dibenzofuran | −7.00 | −7.36 |
| 5 | 2,6,7-triCl-dibenzofuran | −7.35 | −7.63 |
| 6 | 1,2,3,6-tetraCl-dibenzofuran | −7.46 | −7.48 |
| 7 | 1,2,3,7-tetraCl-dibenzofuran | −7.96 | −7.39 |
| 8 | 1,2,4,8-tetraCl-dibenzofuran | −6.00 | −6.19 |
| 9 | 2,3,4,6-tetraCl-dibenzofuran | −7.46 | −7.45 |
| 10 | 2,3,6,8-tetraCldibenzofuran | −7.66 | −7.85 |
| 11 | 2,3,7,8-tetraCl-dibenzofuran | −8.60 | −8.43 |
| 12 | 1,2,3,7,8-pentaCl-dibenzofuran | −8.12 | −8.29 |
| 13 | 1,2,3,7,9-pentaCl-dibenzofuran | −7.40 | −7.29 |
| 14 | 1,2,4,7,9-pentaCl-dibenzofuran | −5.70 | −5.81 |
| 15 | 1,3,4,7,8-pentaCl-dibenzofuran | −7.70 | −7.50 |
| 16 | 2,3,4,7,8-pentaCl-dibenzofuran | −8.82 | −8.42 |
| 17 | 1,2,4,6,7,8-hexaCl-dibenzofuran | −6.08 | −6.09 |
| 18 | 2,3,4,6,7,8-hexaCl-dibenzofuran | −8.33 | −8.74 |
| 19 | 1,2,3,4,7,8-hexaCl-dibenzofuran | −7.64 | −7.46 |
| 20 | 1,2,3,6,7,8-hexaCl-dibenzofuran | −7.57 | −7.56 |
| 21 | 2,3,4,7,9-pentaCl-dibenzofuran | −7.70 | −6.46 |
| 22 | 2,3,4-triCl-dibenzofuran | −5.72 | −5.88 |
| 23 | 2,3-diCl-dibenzofuran | −6.33 | −6.24 |
| 24 | 2,6-diCl-dibenzofuran | −4.61 | −4.53 |
| 25 | 2-Cl-dibenzofuran | −4.55 | −4.75 |
| 26 | 4-Cl-dibenzofuran | −4.50 | −4.72 |
| 27 | 1-Cl-dibenzodioxin | −5.00 | −5.27 |
| 28 | 2,8-diCl-dibenzodioxin | −6.49 | −6.21 |
| 29 | 2,3,7-triCl-dibenzodioxin | −8.15 | −8.98 |
| 30 | 1,3,7,8-tetraCl-dibenzodioxin | −7.10 | −6.67 |
| 31 | 2,3,7,8-tetraCl-dibenzodioxin | −9.00 | −8.37 |
| 32 | 1,2,3,4,7-pentaCl-dibenzodioxin | −6.19 | −6.32 |
| 33 | 1,2,3,4,7,8-hexaCl-dibenzodioxin | −7.55 | −7.19 |
| 34 | 1,2,3,7,8-pentaCl-dibenzodioxin | −8.10 | −8.66 |
| 35 | octaCl-dibenzodioxin | −6.00 | −6.13 |
| 36 | 1,2,3,4-tetraCldibenzodioxin | −6.88 | −7.07 |
| 37 | 1,2,4,7,8-pentaCl-dibenzodioxin | −6.96 | −7.70 |
| 38 | 1,2,4-triCl-dibenzodioxin | −5.88 | −5.99 |
| 39 | 2,3,6,7-tetraCl-dibenzodioxin | −7.79 | −7.49 |
| 40 | 2,3,6-triCl-dibenzodioxin | −7.66 | −7.46 |
| 41 | 2,2',4,4',5,5'-hexaCl-biphenyl | −5.10 | −4.94 |
| 42 | 2,2',4,4'-teraCl-biphenyl | −4.89 | −4.79 |
| 43 | 2,3,3',4,4',5-hexaCl-biphenyl | −6.30 | −5.62 |
| 44 | 2,3,3',4,4'-pentaCl-biphenyl | −6.15 | −6.06 |
| 45 | 2,3',4,4',5,5'-hexaCl-biphenyl | −5.80 | −5.78 |
| 46 | 2,3',4,4',5-pentaCl-biphenyl | −6.04 | −6.02 |
| 47 | 2,3,4,4',5-pentaCl-biphenyl | −6.38 | −6.16 |
| 48 | 2',3'4,4',5-pentaCl-biphenyl | −5.85 | −5.48 |
| 49 | 2,3,4,4'-tetraCl-biphenyl | −5.55 | −5.95 |
| 50 | 2,3,4,5-tetraCl-biphenyl | −4.85 | −5.00 |
| 51 | 3,3',4,4',5-pentaCl-biphenyl | −7.92 | −7.87 |
| 52 | 3,3',4,4'-tetraCl-biphenyl | −7.37 | −7.05 |

Data for the 26 PCDFs, 14 PCDDs, and 12 PCBs used in CoSCoSA models of binding to the AhR enzyme.

Table 3, column 3 contains previously reported log EC$_{50}$ binding data used for training the CoSCoSA models (Safe, *Crit. Rev. Toxicol,* 21:50-88, 1990; Beger and Wilkles, "Models of Polychlorinated Dibenzodioxins, Dibenzofurans, and Biphenyls Binding Affinity to the Aryl Hydrocarbon Receptor Develop using $^{13}$C NMR Data," *J. Chem. Inf. Comput. Sci,* 41: 1360-1366, 2001). Each compound in Table 3 had its $^{13}$C NMR spectra simulated using the ACD Labs CNMR predictor software, version 4.0 (ACD/Labs CNMR software version 4.0, Toronto, Canada). For QSDAR CoSCoSA modeling predicted $^{13}$C NMR spectral data was used. There were no chemical shift peaks outside 107 to 159 ppm. The use of predicted chemical shifts is not necessary to build the QSDAR models, but it saves time, money and in this case prevents possible toxic exposures. Furthermore, predicted $^{13}$C NMR data points allow for the spectra to be independent of the solvent used. The CoSCoSA modeling, LOO cross-validation, and prediction processes were completely computerized. The competitive in vitro binding affinities EC$_{50}$ of PCDF, PCDD, and PCB compounds have been determined previously using [3H]-2,3,7,8-tetrachlorodioxin as the radio-ligand and rodent hepatic cytosol as a source of the AhR (Bhandiera et al., *Toxicology,* 32:131-144, 1984; Bandiera et al, *Chem.-Biol. Interact,* 39:259-277, 1982; Poland and Knutson, *Ann. Rev. Pharmacol, Toxicol,* 22:571-554, 1982; Poland et al., *J. Biol. Chem.,* 251:493-494, 1976; Safe, *Crit. Rev. Toxicol,* 13:319-95, 1984; Safe, *Annu. Rev. Pharmacol. Toxicol.,* 26:371-399, 1986).

In this example, structures were used to predict 1D $^{13}$C NMR spectra for the training set compounds and simulated 2D $^{13}$C—$^{13}$C COSY and $^{13}$C—$^{13}$C distance spectra were calculated. The resolution of the 2D spectra was reduced to either 1.0 or 2.0 ppm in both dimensions to increase the population of "hits" within each bin for statistical analysis, and to reduce the effects of uncertainties in the simulated spectra. The spectral widths were chosen because of convenience and because the 1.0 ppm spectral bin width was used successfully in prior QSDAR and SDAR models based on experimental spectral data. The 2D $^{13}$C—$^{13}$C NMR spectra were saved as two-dimensional bins under the peak within a certain spectral range and normalized to an integer. A single carbon to carbon connectivity was assigned an area of 100; two carbon to carbon connectivities in a bin had an area of 200, and so forth. This was done so that all the carbon to carbon connectivities would have a similar signal-to-noise ratio.

The predicted NMR spectra were calculated by a substructure similarity technique called HOSE (Bremser, *Anal. Chim. Acta,* 103:355-365, 1978), which correlates similar structures with similar NMR chemical shifts. Therefore, the errors produced in the simulated NMR spectra were propagated through the similar structures found in the training set of the QSDAR models. This conveniently reduced the effective error when using the training set to predict unknown sample affinities for compound spectra predicted using the same HOSE routine.

Figure 4:
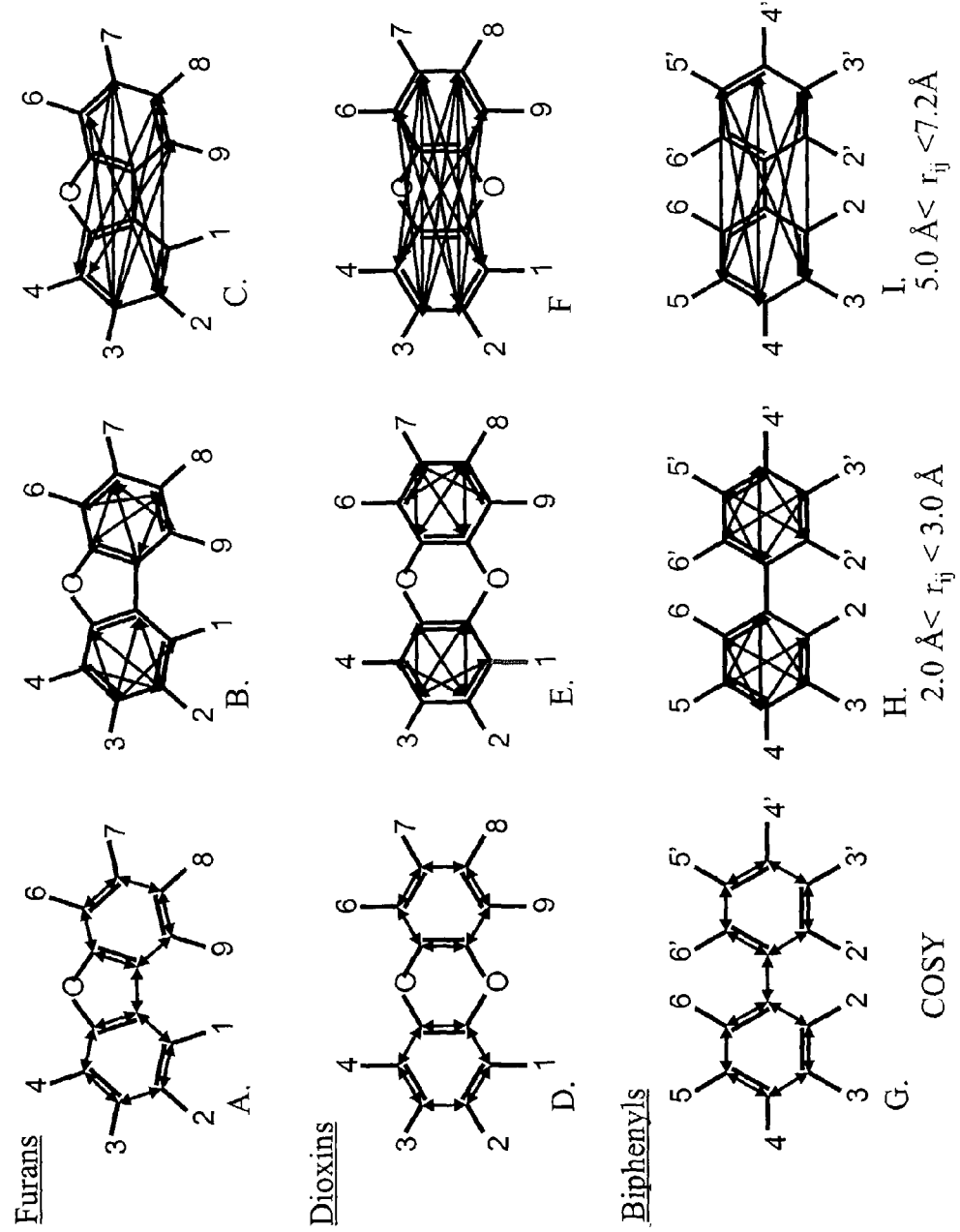
FIG. 4 is a diagram showing the carbon-to-carbon through-bond connections (COSY), the carbon-to-carbon through-space connections in the range 2.0 Å<$r_{ij}$<3.0 Å and the carbon-to-carbon through-space connections in the range 5.0 Å<$r_{ij}$<7.2 Å, where $r_{ij}$ is the intercarbon distance, used to predict $^{13}C$—$^{13}C$ COSY and $^{13}C$—$^{13}C$ distance spectra for dibenzofurans, dibenzo-p-dioxins, and biphenyls.

Structurally assigned $^{13}$C NMR spectra were used to produce predicted 2D $^{13}$C—$^{13}$C COSY and 2D $^{13}$C—$^{13}$C distance spectra based on the molecular structures. The arrows in FIG. 4A show the through-bond neighboring carbon-to-carbon connectivities of a dibenzo-p-dioxin molecule. These through bond carbon-to-carbon connectivities were used to simulate a 2D $^{13}$C—$^{13}$C COSY spectrum of PCDD compounds. Similar procedures were used to produce the predicted $^{13}$C—$^{13}$C 2D-COSY spectra of PCDF and PCB compounds. The arrows in FIG. 4B show the through-space carbon-to-carbon connectivities that are 5.0 to 7.2 Angstroms apart in a dibenzo-p-dioxin molecule. These carbon-to-carbon connectivities were used to produce a theoretical 2D $^{13}$C—$^{13}$C distance spectrum that had cross-peaks when two carbon were 5.0 to 7.2 Angstroms apart for PCDD compounds. Similar procedures were used to produce the theoretical 2D $^{13}$C—$^{13}$C distance spectra of PCDF and PCB compounds. The 2D $^{13}$C—$^{13}$C COSY and 2D $^{13}$C—$^{13}$C distance spectra are symmetrical across the diagonal, and for modeling purposes, only half of each individual spectrum was used. No 1D $^{13}$C NMR spectra were used directly in these CoSCoSA models. All the 2D $^{13}$C—$^{13}$C COSY spectra for the compounds in the CoSCoSA model were reduced to PCs. All the 2D $^{13}$C—$^{13}$C distance spectra for the compounds in the CoSCoSA model were reduced to PCs. The PCs from the 2D $^{13}$C—$^{13}$C COSY spectra and the PCs from the 2D $^{13}$C—$^{13}$C distance spectra were combined. Forward multiple regression was performed on the combined set of PCs to produce a CoSCoSA model.

All statistical analysis was performed by Statistica software (Statistica, StatSoft software, Tulsa, Okla.). CoSCoSA QSDAR models were produced in which the connectivity bins were evaluated with partial least squares (PLS) forward multiple regression analysis using only the most correlated PCs from both the 2D $^{13}$C—$^{13}$C COSY and 2D $^{13}$C—$^{13}$C distance connectivity spectra. Increasing the number of PCs to obtain a $r^2$ greater than 0.9, while ensuring that the overall F-test and $q^2$ were still rising, optimized the number of PCs used in the CoSCoSA models. The F-test for many of the models continued to rise until the number of components in the model equaled the number of compounds in the training set. The number of PC used in the models was limited to less than or equal to half the number of compounds in the training set to retain good predictive capacity for compounds not in the training set.

Evaluations of the QSDAR models were done by the LOO cross-validation procedure in which each compound is systematically excluded from the training set and its inhibitor binding activity is predicted by a model missing any contribution from that compound (Cramer et al., *Quant. Struct.-Act. Relat.*, 7:18-25(1988)). The cross-validated $r^2$ (termed $q^2$) can be derived from $q^2=1-\text{PRESS/SD}$. Here PRESS is the sum of the differences between the actual and predicted activity data for each molecule during LOO cross-validation, and SD is the sum of the squared deviations between the measured and mean activities of each molecule in the training set. The parameter $q^2$ is believed to be a more valid measure than $r^2$ for assessing the reliability of a mathematical model intended for predictive applications.

Figure 5:
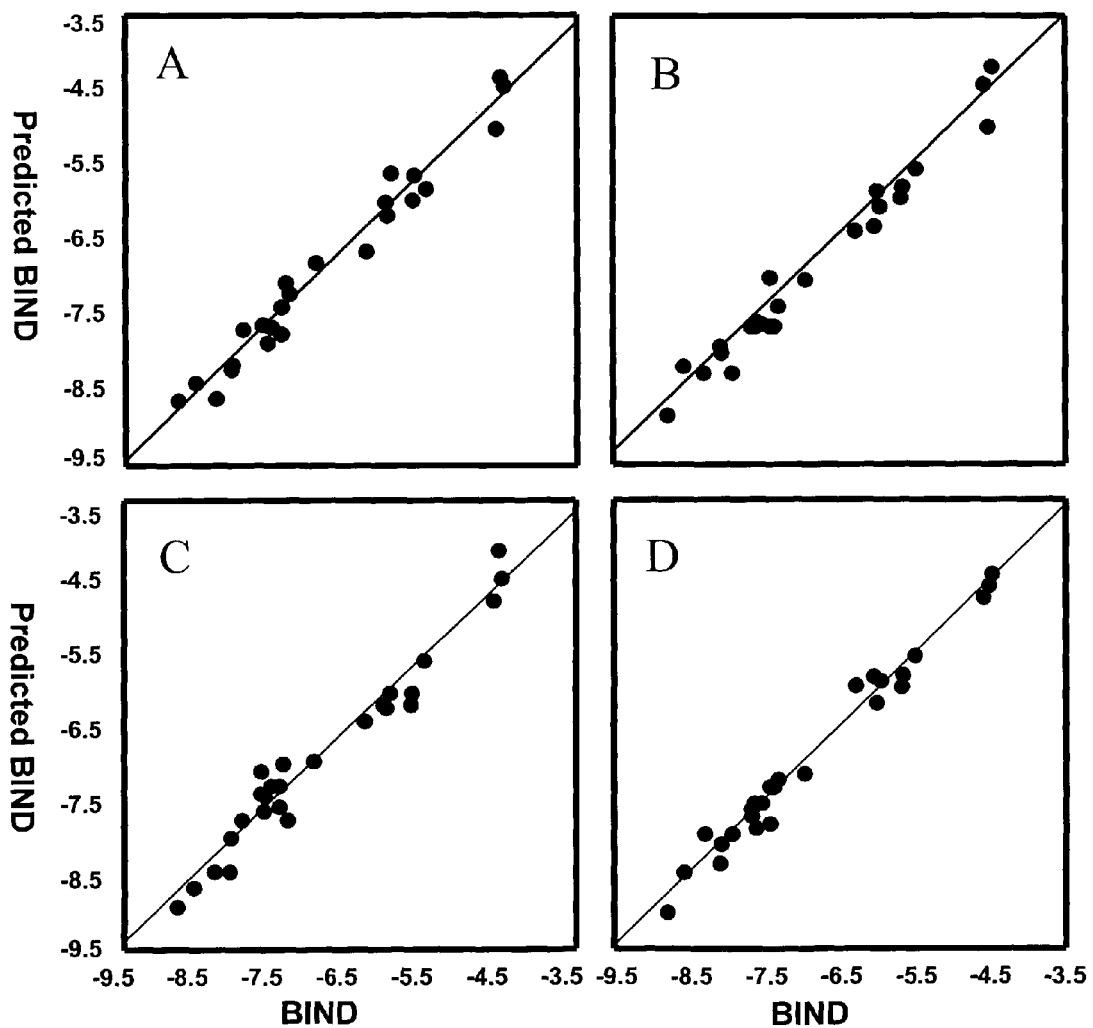
FIG. 5A is a graph of the predicted aryl hydrocarbon receptor binding affinity versus experimental binding affinity for a CoSCoSA model of 26 polychlorinated dibenzofuran (PCDF) compounds based on $^{13}C$—$^{13}C$ COSY and long range (5.0 Å<$r_{ij}$<7.2 Å) $^{13}C$—$^{13}C$ distance spectra using 1.0 ppm spectral ranges to define bins.
FIG. 5B is a graph of the predicted aryl hydrocarbon receptor binding affinity versus experimental binding affinity for a CoSCoSA model of 26 polychlorinated dibenzofuran (PCDF) compounds based on $^{13}C$—$^{13}C$ COSY and $^{13}C$—$^{13}C$ long range (5.0 Å<$r_{ij}$<7.2 Å) distance spectra using 2.0 ppm spectral ranges to define bins.
FIG. 5C is a graph of the predicted aryl hydrocarbon receptor binding affinity versus experimental binding affinity for a CoSCoSA model of 26 polychlorinated dibenzofuran (PCDF) compounds based on $^{13}C$—$^{13}C$ COSY and short range (2.0 Å<$r_{ij}$<3.0 Å) and long range (5.0 Å<$r_{ij}$<7.2 Å) $^{13}C$—$^{13}C$ distance spectra using 1.0 ppm spectral ranges to define bins.
FIG. 5D is a graph of the predicted aryl hydrocarbon receptor binding affinity versus experimental binding affinity for a CoSCoSA model of 26 polychlorinated dibenzofuran (PCDF) compounds based on $^{13}C$—$^{13}C$ COSY and short range (2.0 Å<$r_{ij}$<3.0 Å) and long range (5.0 Å<$r_{ij}$<7.2 Å) $^{13}C$—$^{13}C$ distance spectra using 2.0 ppm spectral ranges to define bins.

FIG. 5 shows plots of predicted binding versus experimental binding for 26 PCDF compound CoSCoSA models based on only ten PCs from PCLR (principal component linear regression analysis). FIGS. 5A and 5B are for models based on combined $^{13}$C—$^{13}$C COSY and long range (5.0 Å<$r_{ij}$<7.2 Å) $^{13}$C—$^{13}$C distance spectra using, respectively, 1 and 2 ppm bins. FIGS. 5C and 5D are based on the PCLR of combined $^{13}$C—$^{13}$C COSY, short-range (2.0 Å<$r_{ij}$<3.0 Å) $^{13}$C—$^{13}$C distance and long-range (5.0 Å<$r_{ij}$<7.2 Å) $^{13}$C—$^{13}$C distance spectra using, respectively, 1 and 2 ppm bins. In FIG. 5A the explained correlation ($r^2$) is 0.97 and a LOO cross-validated variance ($q^2$) is 0.90. The model in FIG. 5B had an $r^2$ of 0.97 and a $q^2$ of 0.92. In FIG. 5C the model had an $r^2$ of 0.95 and a $q^2$ of 0.94. The model in FIG. 5D had an $r^2$ of 0.97 and a $q^2$ of 0.95. These are excellent results and are comparable to or better than a previous 1.0 ppm resolution CoSA model which had an $r^2$ of 0.93 and a $q^2$ of 0.90 and a 2.0 ppm resolution CoSA model that had an $r^2$ of 0.82 and a $q^2$ of 0.72.

Figure 6:
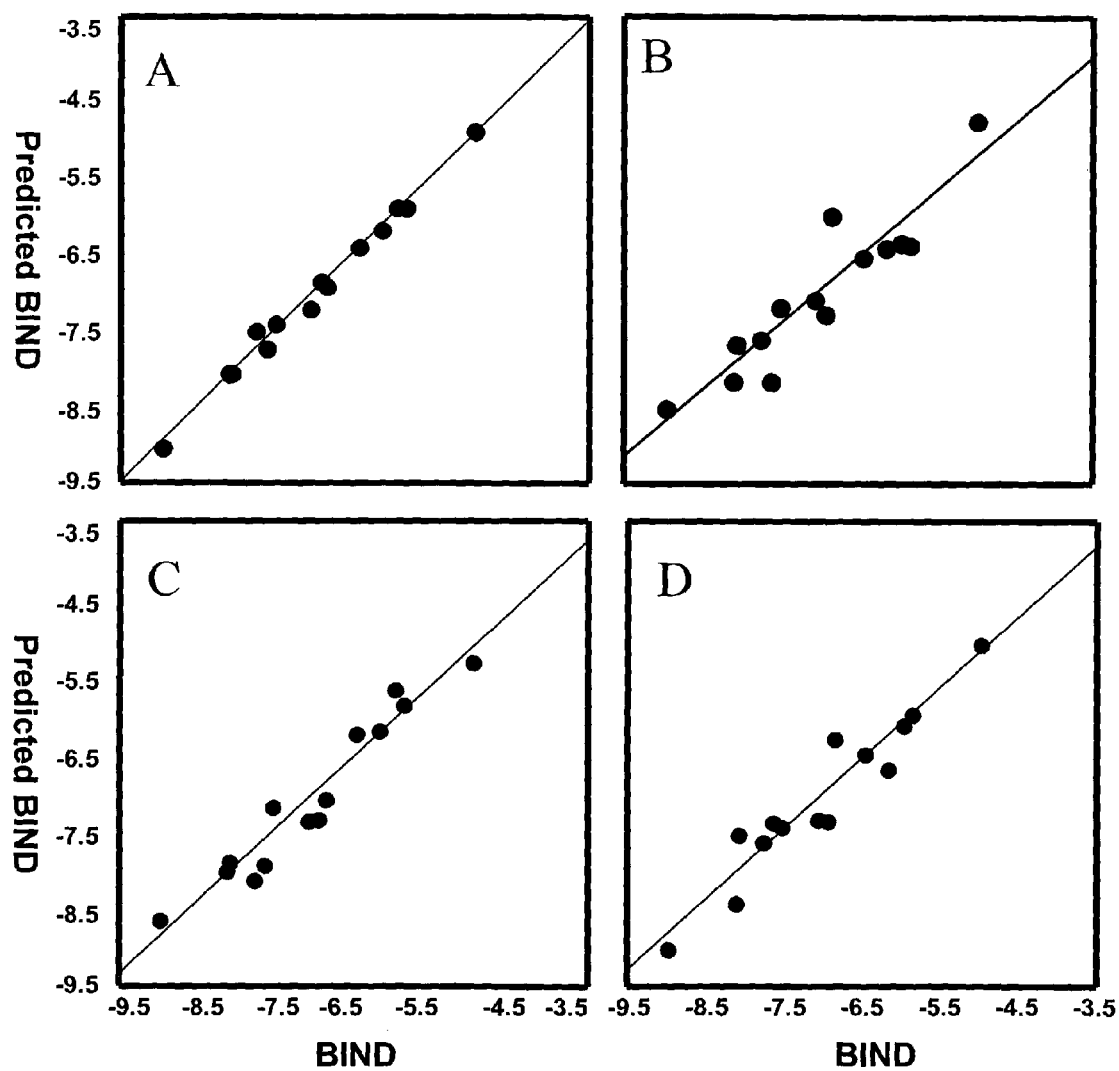
FIG. 6A is a graph of the predicted aryl hydrocarbon receptor binding affinity versus experimental binding affinity for a CoSCoSA model of 14 polychlorinated dibenzo-p-dioxin (PCDD) compounds based on $^{13}C$—$^{13}C$ COSY and long range (5.0 Å<$r_{ij}$<7.2 Å) $^{13}C$—$^{13}C$ distance spectra using 1.0 ppm spectral ranges to define bins.
FIG. 6B is a graph of the predicted aryl hydrocarbon receptor binding affinity versus experimental binding affinity for a CoSCoSA model of 14 polychlorinated dibenzo-p-dioxin (PCDD) compounds based on $^{13}C$—$^{13}C$ COSY and long range (5.0 Å<$r_{ij}$<7.2 Å) $^{13}C$—$^{13}C$ distance spectra using 2.0 ppm spectral ranges to define bins.
FIG. 6C is a graph of the predicted aryl hydrocarbon receptor binding affinity versus experimental binding affinity for a CoSCoSA model of 14 polychlorinated dibenzo-p-dioxin (PCDD) compounds based on $^{13}C$—$^{13}C$ COSY and short range (2.0 Å<$r_{ij}$<3.0 Å) and long range (5.0 Å<$r_{ij}$<7.2 Å) $^{13}C$—$^{13}C$ distance spectra using 1.0 ppm spectral ranges to define bins.
FIG. 6D is a graph of the predicted aryl hydrocarbon receptor binding affinity versus experimental binding affinity for a CoSCoSA model of 14 polychlorinated dibenzo-p-dioxin (PCDD) compounds based on $^{13}C$—$^{13}C$ COSY and short range (2.0 Å<$r_{ij}$<3.0 Å) and long range (5.0 Å<$r_{ij}$<7.2 Å) $^{13}C$—$^{13}C$ distance spectra using 2.0 ppm spectral ranges to define bins.

FIG. 6 shows plots of the predicted binding versus experimental binding for 14 PCDD compound CoSCoSA models based on only seven or five PCs from PCLR. FIGS. 6A and 6B are for models based on the combined $^{13}$C—$^{13}$C COSY and long range (5.0 Å<$r_{ij}$<7.2 Å) $^{13}$C—$^{13}$C distance spectra using, respectively, 1 ppm and 2 ppm bins. FIGS. 6C and 6D are based on the PCLR of combined $^{13}$C—$^{13}$C COSY, short-range (2.0 Å<$r_{ij}$<3.0 Å) $^{13}$C—$^{13}$C distance and long-range (5.0 Å<$r_{ij}$<7.2 Å) $^{13}$C—$^{13}$C distance spectra using, respectively, 1 and 2 ppm bins. In FIG. 6A the $r^2$ is 0.99 and the $q^2$ is 0.95. The model in FIG. 6B had an $r^2$ of 0.86 and a $q^2$ of 0.44. In FIG. 6C, the model had an $r^2$ is 0.94 and the $q^2$ is 0.83. The model in FIG. 6D had an $r^2$ of 0.91 and a $q^2$ of 0.91. These are good results for modeling and most are better than a previous 1.0 ppm resolution CoSA model which had an $r^2$ of 0.87 and a $q^2$ of 0.52 and a 2.0 ppm resolution CoSA model that had an $r_2$ of 0.91 and a $q^2$ of 0.81.

Figure 7:
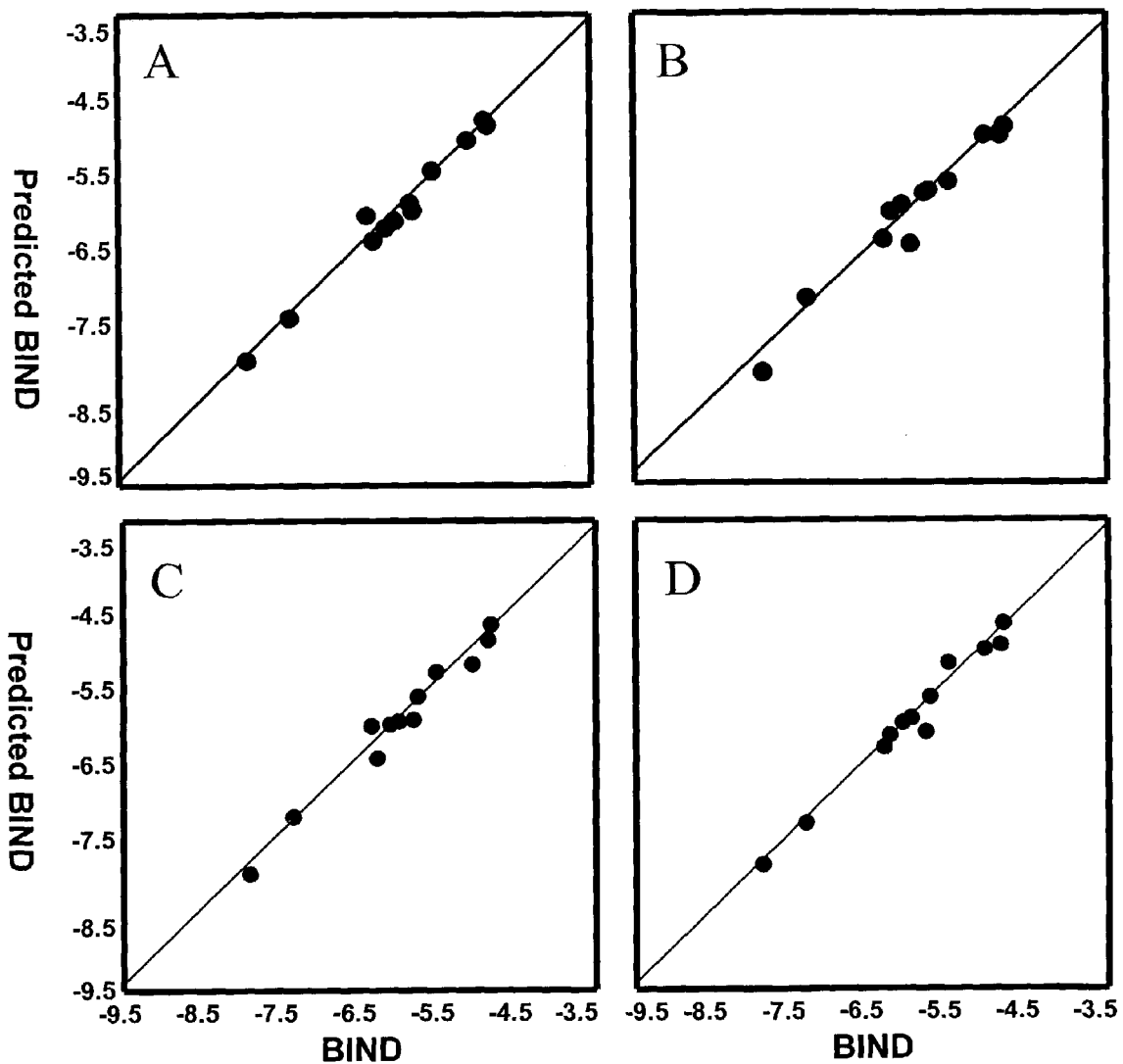
FIG. 7A is a graph of the predicted aryl hydrocarbon receptor binding affinity versus experimental binding affinity for a CoSCoSA model of 12 polychlorinated biphenyl (PCB) compounds based on $^{13}C$—$^{13}C$ COSY and long range (5.0 Å<$r_{ij}$<7.2 Å) $^{13}C$—$^{13}C$ distance spectra using 1.0 ppm spectral ranges to define bins.
FIG. 7B is a graph of the predicted aryl hydrocarbon receptor binding affinity versus experimental binding affinity for a CoSCoSA model of 12 polychlorinated biphenyl (PCB) compounds based on $^{13}C$—$^{13}C$ COSY and long range (5.0 Å<$r_{ij}$<7.2 Å) $^{13}C$—$^{13}C$ distance spectra using 2.0 ppm spectral ranges to define bins.
FIG. 7C is a graph of the predicted aryl hydrocarbon receptor binding affinity versus experimental binding affinity for a CoSCoSA model of 12 polychlorinated biphenyl (PCB) compounds based on $^{13}C$—$^{13}C$ COSY and short range (2.0 Å<$r_{ij}$<3.0 Å) and long range (5.0 Å<$r_{ij}$<7.2 Å) $^{13}C$—$^{13}C$ distance spectra using 1.0 ppm spectral ranges to define bins.
FIG. 7D is a graph of the predicted aryl hydrocarbon receptor binding affinity versus experimental binding affinity for a CoSCoSA model of 12 polychlorinated biphenyl (PCB) compounds based on $^{13}C$—$^{13}C$ COSY and short range (2.0 Å<$r_{ij}$<3.0 Å) and long range (5.0 Å<$r_{ij}$<7.2 Å) $^{13}C$—$^{13}C$ distance spectra using 2.0 ppm spectral ranges to define bins.

FIG. 7 shows plots of the predicted binding versus experimental binding for 12 PCB compound CoSCoSA models that are based on six or five PCs from PCLR. FIGS. 7A and 7B are for models based on the combined $^{13}$C—$^{13}$C COSY and long range (5.0 Å<$r_{ij}$<7.2 Å) $^{13}$C—$^{13}$C distance spectra using, respectively, 1 and 2 ppm bins. FIGS. 7C and 7D are based on the PCLR of combined $^{13}$C—$^{13}$C COSY, short-range (2.0 Å<$r_{ij}$<3.0 Å) $^{13}$C—$^{13}$C distance and long-range (5.0 Å<$r_{ij}$<7.2 Å) $^{13}$C—$^{13}$C distance spectra using, respectively, 1 and 2 ppm bins. In FIG. 7A the explained correlation ($r^2$) is 0.98 and a LOO cross-validated variance ($q^2$) is 0.93. The model in FIG. 7B had an $r^2$ of 0.96 and a $q^2$ of 0.79. In FIG. 7C the $r^2$ is 0.97 and the $q^2$ is 0.97. The model in FIG. 7D had an $r^2$ of 0.98 and a $q^2$ of 0.97. These are excellent results and are much better than a previous 1.0 ppm resolution CoSA model with an $r^2$ of 0.87 and a $q^2$ of 0.45 and a 2.0 ppm resolution CoSA model that had an $r^2$ of 0.75 and a $q^2$ of 0.27.

Figure 8:
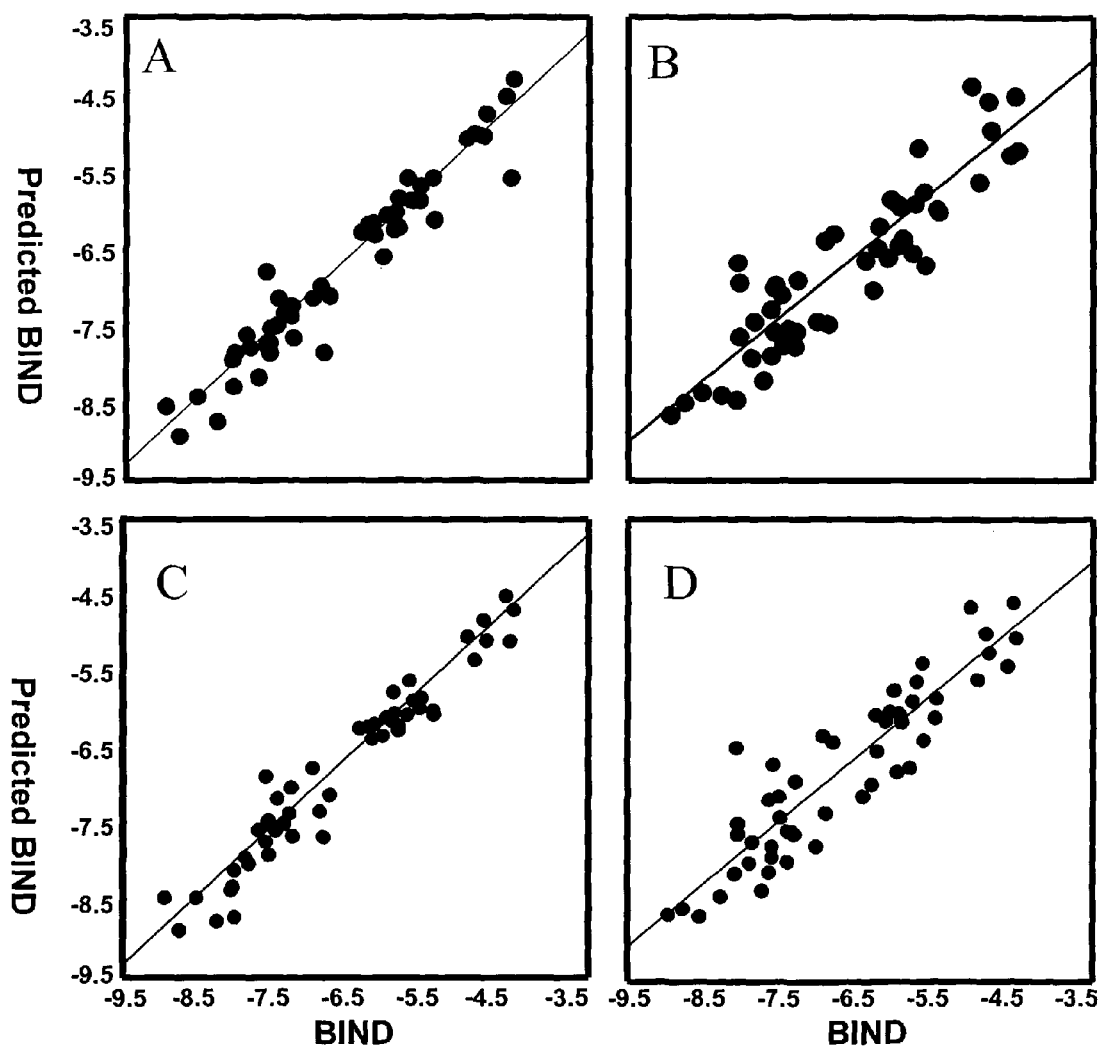
FIG. 8A is a graph of the predicted aryl hydrocarbon receptor binding affinity versus experimental binding affinity for a CoSCoSA model of 52 PCDF, PCDD and PCB compounds based on $^{13}C$—$^{13}C$ COSY and long range (5.0 Å<$r_{ij}$<7.2 Å) $^{13}C$—$^{13}C$ distance spectra using 1.0 ppm spectral ranges to define bins.
FIG. 8B is a graph of the predicted aryl hydrocarbon receptor binding affinity versus experimental binding affinity for a CoSCoSA model of 52 PCDF, PCDD and PCB compounds based on $^{13}C$—$^{13}C$ COSY and long range (5.0 Å<$r_{ij}$<7.2 Å) $^{13}C$—$^{13}C$ distance spectra using 2.0 ppm spectral ranges to define bins.
FIG. 8C is a graph of the predicted aryl hydrocarbon receptor binding affinity versus experimental binding affinity for a CoSCoSA model of 52 PCDF, PCDD and PCB compounds based on $^{13}C$—$^{13}C$ COSY and short range (2.0 Å<$r_{ij}$<3.0 Å) and long range (5.0 Å<$r_{ij}$<7.2 Å) $^{13}C$—$^{13}C$ distance spectra using 1.0 ppm spectral ranges to define bins.
FIG. 8D is a graph of the predicted aryl hydrocarbon receptor binding affinity versus experimental binding affinity for a CoSCoSA model of 52 PCDF, PCDD and PCB compounds based on $^{13}C$—$^{13}C$ COSY and short range (2.0 Å<$r_{ij}$<3.0 Å) and long range (5.0 Å<$r_{ij}$<7.2 Å) $^{13}C$—$^{13}C$ distance spectra using 2.0 ppm spectral ranges to define bins.

FIG. 8 shows plots of the predicted binding versus experimental binding for the combined 26 PCDF, 14 PCDD, and 14 PCDD compound CoSCoSA models that are based on 15 to 22 PCs from PCLR. FIGS. 8A and 8B are based on combined $^{13}$C—$^{13}$C COSY and long range (5.0 Å<$r_{ij}$<7.2 Å) $^{13}$C—$^{13}$C distance spectra using, respectively, 1 and 2 ppm bins. FIGS. 8C and 8D are based on the PCLR of combined $^{13}$C—$^{13}$C COSY, short-range (2.0 Å<$r_{ij}$<3.0 Å) $^{13}$C—$^{13}$C distance and long-range (5.0 Å<$r_{ij}$<7.2 Å) $^{13}$C—$^{13}$C distance spectra using, respectively, 1 and 2 ppm bins. In FIG. 8A the $r^2$ is 0.93 and the $q^2$ is 0.88. The model in FIG. 8B had an $r^2$ of 0.83 and a $q^2$ of 0.65. In FIG. 8C the $r^2$ is 0.83 and the $q^2$ is 0.84. The model in FIG. 8D had an $r^2$ of 0.94 and a $q^2$ of 0.91. These are excellent results and are much better than a previous 1.0 ppm CoSA resolution model with an $r^2$ of 0.87 and $q^2$ of 0.67 and a 2.0 ppm resolution CoSA model that had an $r^2$ of 0.77 and $q^2$ of 0.61.

Table 4 summarizes the performance parameters of four CoSCoSA, a CoSASA model, and a CoSA model for 26 PCDF compounds with respect to the n (number of PCs used), $r^2$, $q^2$, F and σ. It was surprising to find all four CoSCoSA models had a higher $r^2$ and $q^2$ than the 2D CoSASA model that combined spectra and structure information in 3D space.

TABLE 4

26 PCDF compound model performance parameters bin size, n (parameters used), $r^2$, $q^2$, and F.

| Model | Size | N (PC) | $r^2$ | $q^2$ | F |
|---|---|---|---|---|---|
| 1D CoSA | 1 ppm | 5 Bins | 0.93 | 0.90 | 54.7 |
| 2D CoSASA | — | 6 Atoms | 0.74 | 0.70 | 9.1 |
| COSY + (5.0–7.2) Å Distance | 1 ppm | 10 | 0.97 | 0.90 | 49.2 |
| COSY + (5.0–7.2) Å Distance | 2 ppm | 10 | 0.97 | 0.92 | 52.6 |
| COSY + (2.0–3.0) Å + (5.0–7.2) Å | 1 ppm | 10 | 0.95 | 0.94 | 28.9 |
| COSY + (2.0–3.0) Å + (5.0–7.2) Å | 2 ppm | 10 | 0.97 | 0.95 | 53.4 |

Table 5 summarizes the performance parameters of four CoSCoSA models, a CoSASA model, and a CoSA model for AhR binding of 14 PCDD compounds. Here, all four CoSCoSA models had a higher $r^2$ than the 2D CoSASA model and three of the four had higher $q^2$ values that the 2D-CoSASA models. Compared to the one-dimensional CoSA model, three of the four CoSCoSA models had higher $r^2$ and $q^2$ values and demonstrate the improvements possible with CoSCoSA modeling.

TABLE 5

14 PCDD compound model performance parameters bin size, n (parameters used), $r^2$, $q^2$, and F.

| Model | Size | N (PC) | $r^2$ | $q^2$ | F |
|---|---|---|---|---|---|
| 1D CoSA | 2 ppm | 5 Bins | 0.91 | 0.81 | 15.9 |
| 2D CoSASA | — | 5 Atoms | 0.81 | 0.53 | 6.7 |
| COSY + (5.0–7.2) Å Distance | 1 ppm | 7 | 0.99 | 0.95 | 92.4 |
| COSY + (5.0–7.2) Å Distance | 2 ppm | 6 | 0.86 | 0.44 | 6.9 |
| COSY + (2.0–3.0) Å + (5.0–7.2) Å | 1 ppm | 5 | 0.94 | 0.83 | 23.5 |
| COSY + (2.0–3.0) Å + (5.0–7.2) Å | 2 ppm | 5 | 0.91 | 0.91 | 16.2 |

Table 6 summarizes the results of four CoSCoSA models for AhR binding of 12 PCB compounds in comparison to a one-dimensional CoSA model of the same property. Here, all four CoSCoSA models exhibited superior performance statistics compared to the CoSA model.

TABLE 6

12 PCB compound model performance parameters: bin size, n (parameters used), $r^2$, $q^2$, and F.

| Model | Size | N (PC) | $r^2$ | $q^2$ | F |
|---|---|---|---|---|---|
| 1D CoSA | 2 ppm | 5 Bins | 0.87 | 0.45 | 8.1 |
| COSY + (5.0–7.2) Å Distance | 1 ppm | 6 | 0.98 | 0.93 | 44.6 |
| COSY + (5.0–7.2) Å Distance | 2 ppm | 5 | 0.96 | 0.79 | 6.9 |
| COSY + (2.0–3.0) Å + (5.0–7.2) Å | 1 ppm | 5 | 0.97 | 0.97 | 44.3 |
| COSY + (2.0–3.0) Å + (5.0–7.2) Å | 2 ppm | 5 | 0.98 | 0.97 | 47.0 |

Table 7 is a summary of the performance of four CoSCoSA models for all 52 PCDF, PCDD, and PCB compounds. Again, performance was measured with respect to six parameters: n (number of PCs used), $r^2$, $q^2$, F and σ. These results show that the PCDF, PCDD, PCB, and all 52 compound CoSCoSA models had enough information to generalize about the relevant substances' binding affinity to the AhR. All four models represent a significant LOO cross-validation improvement over previously published modeling approaches (Mekemyan et al., *Environ. Health Perspect*, 104:1302-1310, 1996; Turner et al., *J. Comput.-Aided Design*, 11, 409-422, 1997; Beger and Wilkes, *J. Chem. Inf. Comput. Sci*, 41: 1360-1366, 2001; Rannug et al., *Carcinogenesis*, 12:2007-2015, 1991; Kafafi et al., *Chem. Res. Toxicol*; 5:856-862, 1992).

TABLE 7

All 52 PCDF, PCDD, and PCB compound model performance parameters bin size, n (parameters used), $r^2$, $q^2$, and F.

| Model | Size | N (PC) | $r^2$ | $q^2$ | F |
|---|---|---|---|---|---|
| 1D CoSA | 1 ppm | 15 Bins | 0.87 | 0.67 | 16.6 |
| COSY + (5.0–7.2) Å Distance | 1 ppm | 22 | 0.93 | 0.88 | 18.5 |
| COSY + (5.0–7.2) Å Distance | 2 ppm | 15 | 0.83 | 0.65 | 11.5 |
| COSY + (2.0–3.0) Å + (5.0–7.2) Å | 1 ppm | 18 | 0.83 | 0.84 | 11.9 |
| COSY + (2.0–3.0) Å + (5.0–7.2) Å | 2 ppm | 15 | 0.94 | 0.91 | 28.8 |

By comparing the data in Tables 4-7 it is evident that the four 1 ppm CoSCoSA models had better $r^2$ than the 2 ppm CoSCoSA models. All 1 ppm CoSCoSA models except for PCDF CoSCoSA models had a better $q^2$ than the 2 ppm CoSCoSA models. CoSA modeling of binding to the ArH for 26 PCDF, 14 PCDD 12 PCB compounds (a total of 52 compounds) provided results that are at least equivalent to and often far superior to other modeling methods. By comparison, all four CoSCoSA models showed some form of improvement over the CoSA models. The CoSA models were based on selected "bins" from a ID spectrum, whereas the CoSCoSA models are based on selected PCs from 2D $^{13}C$—$^{13}C$ COSY and 2D $^{13}C$—$^{13}C$ distance spectra, and there is more structural information in the CoSCoSA model. Inclusion of structural information in the spectral data appears to be responsible for the improvements seen in the CoSCoSA models of binding to ArH.

The 1 ppm CoSCoSA model for all 52 compounds used 19% of the available bins in a 2D $^{13}C$—$^{13}C$ COSY spectrum covering spectral ranges of 107 to 159 ppm in each dimension. The 1 ppm CoSCoSA model for all 52 compounds used 14% of the available bins in a 2D $^{13}C$—$^{13}C$ distance spectrum covering the same spectral ranges. The 2 ppm CoSCoSA models used 38% and 22% of the available "2D-space" between 107 ppm and 159 ppm for the 2D $^{13}C$—$^{13}C$ COSY spectrum and the 2D $^{13}C$—$^{13}C$ distance spectrum, respectively. Considering that a typical 2D $^{13}C$—$^{13}C$ spectrum may range over 0 to 220 ppm the number of available bins used in 1 or 2 ppm CoSCoSA models for the 52 compounds drops to 1% of the available chemical shift "2D space". Because little of the available chemical shift "2D space" in the 52 compound CoSCoSA models is used, it is believed that accurate CoSCoSA models with much larger and diverse training sets are possible.

In one aspect, a 2D $^{13}C$—$^{13}C$ COSY spectrum is a 2D $^{13}C$—$^{13}C$ distance spectrum with the distances set less than 1.5 Angstroms. The 2D $^{13}C$—$^{13}C$ COSY spectrum and 2D $^{13}C$—$^{13}C$ distance spectrum are reduced forms of a 3D spectral connectivity matrix (see FIG. 13) where the $^{13}C$ chemical shift appears as the x- and y-axes and the distance ($r_{ij}$) between carbon atoms is the z-axis. In other words, for the 2D $^{13}C$—$^{13}C$ COSY spectrum all distances less than 1.5 Angstrom are selected and reduced to a 2D plane. For the 2D $^{13}C$—$^{13}C$ distance spectrum in these CoSCoSA models all distances greater than 5 Angstroms were selected and compressed into a 2D plane. No structural information regarding intercarbon connectivities between 2.0 and 5.0 Angstroms was used for the CoSCoSA models of binding to the AhR because prior models indicated that the 2, 3, 7, and 8 positions of PCDF and PCDD compounds were most important for AhR binding and these atoms are separated by greater than 5.0 Angstroms. Similarly the 3, 4, 5, 3', 4', and 5' positions of PCB compounds are known to be most important, and are separated by at least 5.0 Angstroms. However, for other groups of molecules, and different endpoints, other distance ranges may be important. Selecting a distance range of data from the 3D spectral connectivity matrix is like segmenting the spectral data in the inter-atomic (more generally, inter-structural component distance) dimension to form 3D bins. Where subtle differences in distance are important for determining a particular molecular property, small distance ranges or "bins" may be needed or desired to more faithfully model the property. Therefore, the distance dimension may be divided into "bins" of a width equal to or greater that the structural resolution (i.e. how finely can the structure be determined). The practical (although not theoretical) upper limit on the distance "bin" size is a range of distances that includes all distance interactions between structural components seen for the training set of molecules and any test or validation compounds for which a prediction of a property is desired. Examples of useful distance "bin" widths include 1, 2, 3, 4, 5, 6, 7, 8, 9 and 10 or greater Angstroms, and intermediate factional widths. Examples of bin ranges include 0-2, 0-3, 0-4, 0-5, 0-6, 0-7, 0-8, 0-9, 0-10, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10 and 9-10 Angstroms, and fractional intermediate ranges, and ranges expressed in other measures of distance, such as nanometers.

The CoSCoSA modeling system can be applied to systems where the structural information on the binding site is still unknown, and for many cases in the pharmaceutical industry this is the norm. In contrast, producing QSAR models without detailed structural information is very unreliable and based on intuition. Furthermore, even when the structural information is available for CoMFA QSAR models, the CoSCoSA QSDAR models outperform them based on tests of predictability. Because CoSCoSA modeling can be produced without subjective judgement and with very quick and accurate results, it can be a valuable modeling system for any industry that relies on structural models. CoSCoSA modeling is also ideally suited for dealing with high throughput binding data.

CoSCoSA modeling where fewer than all available chemical shift bins are used is similar to QSAR modeling which removes the data from points in space where the energy calculated is always too small. The choice of the number and size of bins in all dimensions desirably avoid the extremes. A bin size that is too large tends to inappropriately lump distinct spectral information into the same category and a bin size that is too small suffers from false distinctions between spectral features. Furthermore, lower average bin occupancy values that result from small bins may adversely affect the statistics needed to identify and confirm the pattern. If too large a number of bins (small bin size) is used the model is likely to exhibit an excellent $r^2$, but also exhibit a poor $q^2$ In this example, using $^{13}$C NMR data, 1 ppm and 2 ppm bins for the spectral data seemed to work best. The size of the two-dimensional bins in the $^{13}$C chemical shift plane and the distance cutoffs (ranges, distance bins) used for the $^{13}$C—$^{13}$C 2D distance spectra were not optimized. It is possible that different bin sizes in any of the dimensions may lead to better models. Nonetheless, very accurate models of PCDD, PCDF, and PCB compounds binding to AhR were obtained without having to optimize bin size and distance cutoffs. For other biological, physical, and toxicological endpoints optimized bin sizes, distance cutoffs, and the number of distance spectra used in the CoSCoSA may differ from those used here. The ease and speed with which models may be altered facilitate optimization of these parameters. Once the spectral data and connectivity information is obtained, the parameters may be optimized by repeatedly altering them and detecting improvements in the performance statistics.

Example 3

3D CoSCoSA Models of Steroid Binding to the Aromatase Enzyme

The aromatase enzyme catalyzes the conversion of testosterone to estradiol by the aromatization of the A-ring in steroids. Estrogen production from aromatase enzyme activity is important in the evolution and development of estrogen-dependent tumors. Inhibition of the aromatase enzyme, a cytochrome P450 complex that converts androgens to estrogens, is therapeutically significant because it may control breast cancer (See, for example, Brodie and Santon, *Breast Cancer Res. Treat.*, 30:1-6, 1994).

CoSCoSA models were produced using methods analogous to those described in Examples 1 and 2. Table 8 shows the core steroid structures, substitution patterns, and experimental aromatase binding data for the 50 steroids used to develop models of aromatase binding. Each compound in Table 8 had its $^{13}$C spectrum calculated and these spectra were used along with structural data to create a 3D spectral connectivity data matrix for each compound.

TABLE 8

Structural features and experimental binding data of the steroids used in 3D-QSDAR models of binding to the aromatase enzyme.

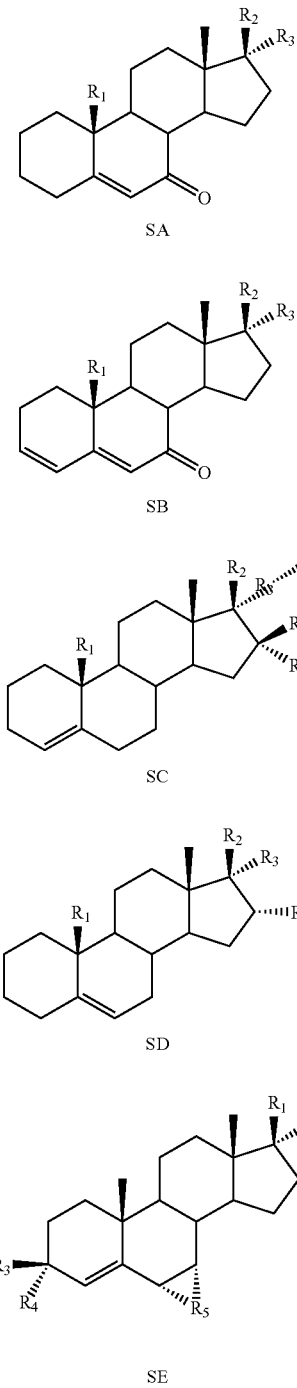

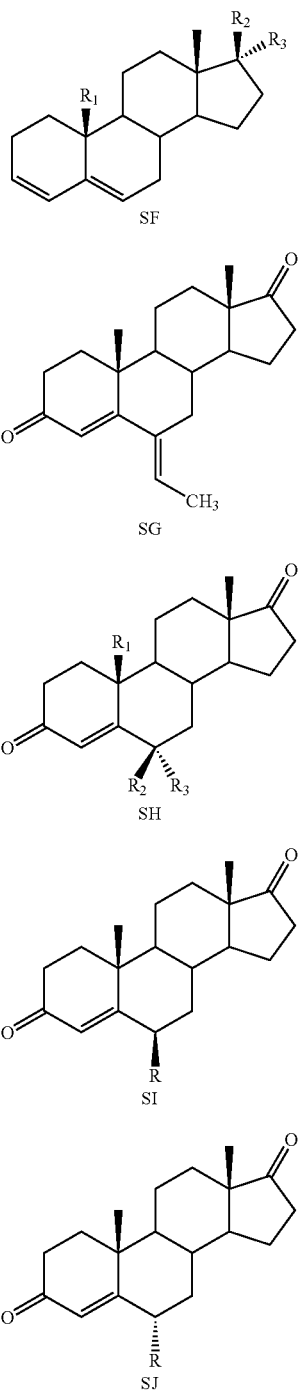

| # | Binding | structure | $R_1$ | $R_2$ | $R_3$ | $R_4$ | $R_5$ |
|---|---|---|---|---|---|---|---|
| 1 | −2.92 | SA | $CH_2OH$ | =O | | | |
| 2 | −3.54 | SA | $CH_2OH$ | OH | H | | |
| 3 | −3.00 | SA | CHO | =O | | | |
| 4 | −3.26 | SA | H | O | | | |
| 5 | −2.62 | SA | Me | OH | H | | |
| 6 | −3.06 | SB | $CH_2OH$ | =O | | | |
| 7 | −2.14 | SB | CHO | =O | | | |
| 8 | −2.36 | SB | H | =O | | | |
| 9 | −1.89 | SD | $CH_2OH$ | =O | | H | |
| 10 | −2.88 | SD | $CH_2OH$ | OH | H | H | |
| 11 | −2.03 | SD | CHO | =O | | H | |
| 12 | −0.97 | SD | Me | =O | | H | |
| 13 | −2.93 | SD | Me | =O | | Br | |
| 14 | −1.28 | SA | Me | =O | | | |
| 15 | −1.23 | SB | Me | =O | | | |
| 16 | −2.61 | SB | Me | OH | H | | |
| 17 | −2.36 | SD | Me | OH | H | H | |
| 18 | −0.65 | SF | =O | | | | |
| 19 | −2.19 | SF | OH | H | | | |
| 20 | −1.03 | SH | H | H | H | | |
| 21 | 0.00 | SC | Me | =O | | H | H |
| 22 | 0.46 | SC | $CH_2OH$ | =O | | H | H |
| 23 | −0.84 | SH | $CH_2OH$ | H | H | | |
| 24 | 0.15 | SH | Me | =O | | | |
| 25 | −0.13 | SE | =O | | =O | | $CF_2$ |
| 26 | 0.87 | SIE | =O | | H | H | $CH_2$ |
| 27 | −0.51 | SIE | OH | H | H | H | $CH_2$ |
| 28 | −1.35 | SC | Me | OH | H | H | H |
| 29 | −0.67 | SC | $CH_2OH$ | OH | H | H | H |
| 30 | −0.89 | SC | $MeC(O)OCH_2$ | =O | | H | H |
| 31 | −0.79 | SC | Me | =O | | H | Br |
| 32 | −1.09 | SC | Me | =O | | H | H |
| 33 | −1.08 | SC | $CF_3$ | =O | | H | H |
| 34 | 0.56 | SI | Me | | | | |
| 35 | 0.87 | SJ | Me | | | | |
| 36 | 1.56 | SI | $C_2H_5$ | | | | |
| 37 | 0.94 | SJ | $C_2H_5$ | | | | |
| 38 | 0.94 | SI | $C_3H_7$ | | | | |
| 39 | 0.78 | SJ | $C_3H_7$ | | | | |
| 40 | 0.65 | SI | $C_nH_9$ | | | | |
| 41 | 0.53 | SJ | $C_4H_9$ | | | | |
| 42 | 0.21 | SI | $CH(CH_3)_2$ | | | | |
| 43 | 0.04 | SJ | $CH(CH_3)_2$ | | | | |
| 44 | −0.04 | SI | $C_6H_5$ | | | | |
| 45 | 0.24 | SJ | $C_6H_5$ | | | | |
| 46 | −0.24 | SI | $CH_2C_6H_5$ | | | | |
| 47 | 0.61 | SJ | $CH_2C_6H_5$ | | | | |
| 48 | 0.91 | SI | $CH=CH_2$ | | | | |
| 49 | −0.32 | SI | C≡CH | | | | |
| 50 | 0.96 | SG | | | | | |

The predicted NMR spectra were calculated by the HOSE substructure similarity technique, which correlates similar structures with similar NMR chemical shifts. Therefore, the errors produced in the simulated NMR spectra were propagated through the similar structures found in the training set of the QSDAR models. This conveniently reduced the effective error when using the training set to predict unknown sample affinities for compound spectra predicted using the same HOSE routine.

Structurally assigned $^{13}C$ NMR spectra were used to produce the 3D spectral connectivity data matrix for each compound and theoretical 2D $^{13}C$—$^{13}C$ COSY and 2D $^{13}C$—$^{13}C$ distance spectra were derived from the data in the 3D spectral connectivity matrix. A 3D-connectivity matrix may be built by displaying all possible carbon-to-carbon connections and their assigned carbon NMR chemical shifts (see, for example, FIG. 13) so that the x-axis is the chemical shift of carbon i, the y-axis is the chemical shift of carbon j, and the z-axis is the distance between carbon i and carbon j ($r_{ij}$). The information in a 3D-connectivity matrix is over-determined, so it is possible reduce the information in the matrix that is needed for an effective model. One way to reduce the amount of information is to reduce the 3D matrix into sets of 2D planes. For example, the 3D $^{13}C$—$^{13}C$ spectral connectivity matrix could be reduced to any number of 2D spectral planes, such as four 2D spectral planes including a nearest neighbor through-bond connectivity plane (COSY, $r_{ij}$<20 Å), and short range (e.g. 2.0 Å<$r_{ij}$<3.6 Å), medium range (e.g. 3.6 Å<$r_{ij}$<6.0 Å) and long range (e.g. $r_{ij}$>6.0 Å) atom-to-atom through-space connectivity connections. In this example only the through-bond COSY data and long range through-space data was used because the models were not improved significantly by adding the short and medium range data. For other models this may not be true, and short or medium range data may be important. The resolution of the 2D spectra was reduced to 2.0 ppm in both chemical shift dimensions to populate more of the NMR bins for statistical analysis, and to reduce the effects of uncertainties in the simulated spectra. The spectral bin width of 2.0 ppm was chosen for convenience, but may be varied from the digital resolution of the spectral data to 10 ppm or greater, depending upon the number of spectral signals within a certain spectral range. The 2D $^{13}C$—$^{13}C$ NMR spectra were saved as two-dimensional bins under the peaks within a certain spectral range and normalized to an integer. A single carbon to carbon connectivity was assigned an area of 100; two carbon to carbon connections in a bin had an area of 200, and so forth. This was done so that all the carbon to carbon connections would have a similar signal-to-noise ratio.

At least four types of CoSCoSA models of binding to aromatase can be built from the 2D COSY and 2D long range distance spectra. In one embodiment, the combined spectra (3D) are used. In other embodiments, the combined PCs from the COSY PCs and Distance PCs are used. Referring again to FIG. 1, these approaches include using an approach represented by arrows A, where only the 2D $^{13}C$—$^{13}C$ COSY spectral data are reduced to PCs and these PCs are then used for multiple linear regression to produce a model from the 2D $^{13}C$—$^{13}C$ COSY data. Alternatively, arrows B represent an approach where only 2D $^{13}C$—$^{13}C$ distance connectivity spectral data are reduced to PCs and these PCs are then used for multiple linear regression to produce a model for the 2D $^{13}C$—$^{13}C$ distance connectivity data. Arrows C represent a procedure where the combined PCs from the 2D $^{13}C$—$^{13}C$ COSY and the 2D $^{13}C$—$^{13}C$ distance connectivity spectral data are used to produce a combined through-bond and through-space CoSCoSA model. Arrows D represent the procedure where the 2D $^{13}C$—$^{13}C$ COSY and the 2D $^{13}C$—$^{13}C$ distance connectivity spectral data are first combined and then reduced to PCs. By selecting only a particular distance range of connectivity data, a model based on only a part of the three-dimensional representation of the 2D $^{13}C$—$^{13}C$ COSY and 2D $^{13}C$—$^{13}C$ distance spectra data may be constructed. For example, models based on COSY and one or more ranges of connectivity data may be produced.

All PCLR statistical analyses were performed using Statistica software, versions 5.5 and 6.0 (StatSoft, Tulsa, Okla.). The CoSCoSA QSDAR models were produced in which the connectivity bins were evaluated with forward multiple linear regression analysis using only the most correlated PCs from both the 2D $^{13}C$—$^{13}C$ COSY and 2D $^{13}C$—$^{13}C$ distance connectivity spectra. The number of PCs selected was based on the number that produced a maximum value for the F-test.

The analysis of each PCLR CoSCoSA model was done by the leave-one-out (LOO) cross-validation procedure where each compound is systematically excluded from the training set and its binding activity is predicted by the model. The cross-validated $r^2$ (termed $q^2$) can be derived from $q^2=1-(PRESS)/SD$. Where PRESS is the sum of the differences between the actual and predicted activity data for each molecule during LOO cross-validation, and SD is the sum of the squared deviations between the measured and mean activities of each molecule in the training set. The value of $q^2$ is believed to be a more valid measure than $r^2$ for assessing the reliability of a mathematical model intended for predictive applications. Similarities between the pattern of 2D spectral data associated with the biological activity of the training set compounds and the spectral data for a test compound may then be detected based on the model and used to determine whether the test compound is predicted to exhibit the biological activity.

Table 9 compares the model performance parameters n, $r^2$, $q^2$, and the number of components used for previously reported models of aromatase binding affinity based on a combination QSAR/E-state model, a 1D CoSA model, a 2D CoSASA model, and the new CoSCoSA models described herein. In Table 9, the model entries labeled "2D COSY CoSCoSA" correspond to the approach of arrows A in FIG. 1, the entries labeled "2D 6-9 Å Distance CoSCoSA" correspond to arrows B in FIG. 1, the entries labeled "2D COSY+ Distance CoSCoSA" correspond to arrows C in FIG. 1, and the entries labeled "3D" correspond to arrows D in FIG. 1. All four CoSCoSA models with 7 or more PCs have a strong correlation ($r^2$) and cross-validated variance ($q^2$) and are favorable when compared to the previous published models of binding to the aromatase enzyme. The statistical results were further tested and validated by randomizing the binding activity data. The best statistical correlation occurred using actual binding data.

TABLE 9

Performance Characteristics of Models of Aromatase Binding

| Model | # of PC's | | $r^2$ | $q^2$ |
|---|---|---|---|---|
| CoMFA | 5 | | 0.94 | 0.72 |
| 1D CoSA | 5 | | 0.78 | 0.71 |
| 1D CoSA | 5 | bins | 0.82 | 0.77 |
| 2D CoSASA | 5 | | 0.75 | 0.67 |
| 2D CoSASA | 5 | atoms | 0.74 | 0.66 |
| 2D COSY CoSCoSA | 5 | | 0.77 | 0.68 |
| 2D COSY CoSCoSA | 9 | | 0.89 | 0.89 |
| 2D 6-9 Angstrom Distance CoSCoSA | 5 | | 0.65 | 0.65 |
| 2D 6-9 Angstrom Distance CoSCoSA | 7 | | 0.72 | 0.72 |
| 2D COSY + Distance CoSCoSA | 5 | | 0.77 | 0.68 |
| 2D COSY + Distance CoSCoSA | 10 | | 0.92 | 0.86 |
| 3D CoSCoSA | 5 | | 0.77 | 0.77 |
| 3D CoSCoSA | 8 | | 0.87 | 0.83 |

Figure 9:
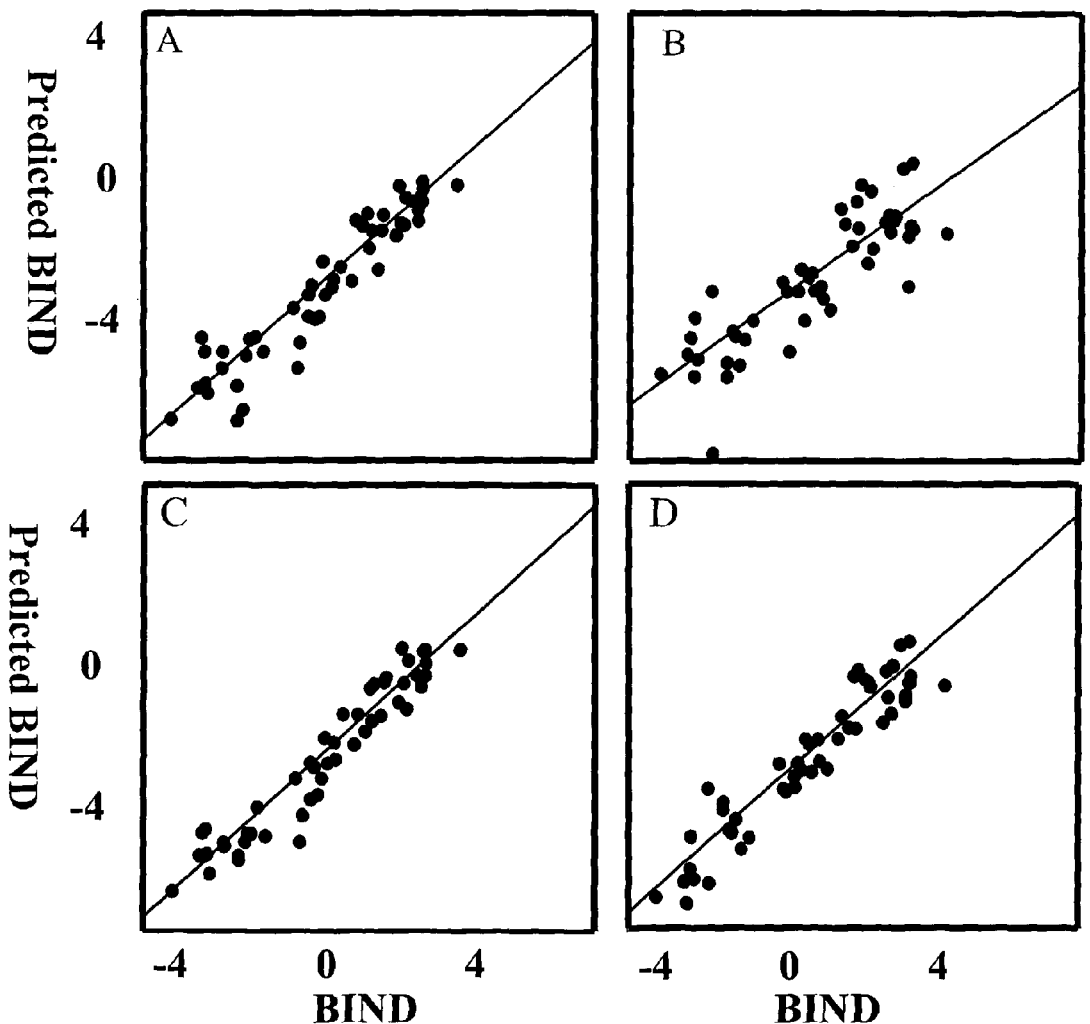
FIG. 9A is a graph of the predicted aromatase binding affinity versus experimental binding affinity for a CoSCoSA model of steroid binding based only on predicted $^{13}C$—$^{13}C$ COSY spectral data.
FIG. 9B is a graph of the predicted aromatase binding affinity versus experimental binding affinity for a CoSCoSA model of steroid binding based only on predicted $^{13}C$—$^{13}C$ distance spectral data for carbon atoms separated by 6 to 9 Angstroms.
FIG. 9C is a graph of the predicted aromatase binding affinity versus experimental binding affinity for a CoSCoSA model of steroid binding based on a combination of PCs derived from predicted $^{13}C$—$^{13}C$ COSY spectral data and $^{13}C$—$^{13}C$ distance spectral data for carbon atoms separated by 6 to 9 Angstroms.
FIG. 9D is a graph of the predicted aromatase binding affinity versus experimental binding affinity for a CoSCoSA model of steroid binding based on a combination of predicted $^{13}C$—$^{13}C$ COSY spectral data and $^{13}C$—$^{13}C$ distance spectral data for all through-space carbon-to-carbon connections.

FIG. 9A is a plot of the predicted binding versus experimental binding for the CoSCoSA 2.0 ppm resolution model based on $^{13}C$—$^{13}C$ COSY data. A model based on 9 PC's had an explained correlation ($r^2$) of 0.89 and the cross-validated variance ($q^2$) was 0.89, which indicates self-consistency and excellent predictive capability. FIG. 9B is a plot of the predicted binding versus experimental binding for the CoSCoSA 2.0 ppm resolution model based on $^{13}C$—$^{13}C$ distance connectivity data for through space carbon-carbon interactions of greater than 6.0 Angstroms. Using 7 PCs the $r^2$ of this model was 0.72 and the $q^2$ was 0.72. FIG. 9C is a plot of the predicted binding versus experimental binding for the CoSCoSA 2.0 ppm resolution model based on the combination of $^{13}C$—$^{13}C$ COSY and $^{13}C$—$^{13}C$ distance connectivity PCs. The model based on 10 PCs had an $r^2$ of 0.92 and a $q^2$ of 0.86, which indicates excellent self-consistency and predictive capability. FIG. 9D is a plot of the predicted binding versus experimental binding for the CoSCoSA 2.0 ppm resolution model where the $^{13}C$—$^{13}C$ COSY and $^{13}C$—$^{13}C$ distance connectivity spectral data were combined before principal component extraction. The model based on 8 PCs and had an $r^2$ of 0.87 and a $q^2$ of 0.83, which again indicates self-consistency and high predictive capability.

The effect of using different bin sizes was investigated by increasing the bin size to 3.0 ppm. For the model based on $^{13}C$—$^{13}C$ COSY data, the $r^2$ increased from 0.77 to 0.78 and $q^2$ increased from 0.68 to 0.77. For the model based on $^{13}C$—$^{13}C$ distance connectivity data, the $r^2$ increased from 0.65 to 0.79 and $q^2$ increased from 0.65 to 0.79. For the model based on the combined $^{13}C$—$^{13}C$ COSY and $^{13}C$—$^{13}C$ distance connectivity PCs, the $r^2$ increased from 0.77 to 0.80 and $q^2$ increased from 0.68 to 0.81. For the model based on the combined $^{13}$C—$^{13}$C COSY and $^{13}$C—$^{13}$C distance connectivity data before extraction of principal components, the $r^2$ increased from 0.77 to 0.78 and $q^2$ increased from 0.77 to 0.78. Overall, the performance parameters $r^2$ and $q^2$ of the four CoSCoSA models based on 5 PCs were slightly better with 3 ppm bins as opposed to 2 ppm bins in this instance.

All four CoSCoSA models based on the number of PCs giving an F-test maximum have a $q^2$ greater than the 0.72 seen for the CoMFA QSAR model. The reason models based on more than 5 PCs are compared to models based on 5 components is that the CoSCoSA models are "digital" in nature whereas QSAR models are in an "analog" format and require fewer variables to describe the same property. The CoSCoSA models display the same electrostatic information used in QSAR, but have a better signal to noise (predictability) than other models when more components are used.

Another possible explanation for the fact that the cross-validated variance of the QSDAR model was as good as the other models is that even simulated NMR spectral data are more accurate than the errors introduced by solvent effects, partial charges, dielectrics, and structural conformations used during the calculation of electrostatic potentials. All of the assumptions and approximations are prone to produce significant error. $^{13}$C NMR spectral data takes into account all structural conformations and complete solvent effects to produce a "quantum mechanical energy" that represents the average structural environment for every carbon atom in the molecule.

In the CoSA QSDAR model, only 256 spectral bins were used, a number then reduced to 87 spectral bins when all the bins with only zeroes or with only one non-zero entry were removed. This indicates that approximately 34% of the available space was needed to model aromatase binding with the one-dimensional CoSA method. By comparison, the 2.0 ppm CoSCoSA models start with 6441 two-dimensional bins, a number then reduced to 280 for the $^{13}$C—$^{13}$C COSY data and 397 for the $^{13}$C—$^{13}$C distance connectivity data when all the columns with only zeroes were removed. Less than 6% of the available 2D connectivity spectral space is used with this training set and a 2 ppm resolution bin size. Similarly, in the 3.0 ppm CoSCoSA models there are 2926 two-dimensional bins, a number then reduced to 194 for the $^{13}$C—$^{13}$C COSY data and 379 for the $^{13}$C—$^{13}$C distance connectivity data when all the columns with only zeroes were removed. Less than 7% of the available 2D COSY through-bond spectral space and 13% of the available through-space spectral space was used with this training set and a 3 ppm resolution bin size, indicating that much larger training sets including non-congeneric molecules may be accommodated.

The CoSCoSA QSDAR models take into account the average uncertainty in the predicted $^{13}$C NMR data and therefore reduce the information content of the spectra by reducing the number of spectral bins and ignoring the shape of the chemical shift peaks. Still, the CoSCoSA models retained enough information by increasing the number of chemical shifts in many spectral bins to produce reliable models of binding to the aromatase enzyme. The NMR chemical shift peak has information about atom adjacency, solvent effects, and average structural conformation, but the shape of the peak is greatly affected by shimming and temperature dependent dynamics. Inclusion of average uncertainty into the simulated $^{13}$C NMR data does not appear to affect the ability of simulated $^{13}$C NMR data to be used to model the binding affinity of structurally similar compounds to a receptor.

Overall, the selected combined structure and chemical shift information from the 3D-connectivity matrix was shown to provide a set of descriptors that may be used to produce very accurate models of steroids binding to the aromatase enzyme. The 3D-connectivity matrix uniquely combines quantum mechanical information from the chemical shifts with nearest neighbor and internal distance connectivity information. The combined information from COSY and long-range distance connectivity information from the 3D-connectivity matrix was able to produce CoSCoSA models that are much more accurate and reliable than QSAR or E-state models based on separate calculations for electrostatics and steric interactions. The cross-validated variance of CoSCoSA models based on simulated $^{13}$C NMR data should improve as the errors introduced by the simulation of the $^{13}$C NMR data are further reduced by improved spectral simulation programs.

The 2D $^{13}$C—$^{13}$C COSY nearest neighbor connectivity spectral data should be important for almost any molecular property or binding affinity. However, it is likely that the $^{13}$C—$^{13}$C distance connectivity data will be important when one or more distance separated structural features are required for a certain molecular property such as a large molecule binding to a receptor. This appears to be the case for steroids binding to aromatase because the widely separated regions around positions 3 and 17 of the steroid backbone are important for binding.

The CoSCoSA models that combined the $^{13}$C—$^{13}$C COSY and $^{13}$C—$^{13}$C distance connectivity PCs together produced the models with the highest $r^2$ and $q^2$. The combined $^{13}$C—$^{13}$C COSY and $^{13}$C—$^{13}$C distance connectivity PCs models were better than PCs extracted from the combined three-dimensional $^{13}$C—$^{13}$C COSY and $^{13}$C—$^{13}$C distance connectivity data, apparently because there were twice as many available PCs when the PC were first extracted from each type of data, and then combined.

The CoSCoSA modeling method may be further improved by including spectral data other than $^{13}$C NMR spectral. A promising type of NMR data is $^{15}$N NMR data because nitrogen is found in many important organic molecules, for example, alkaloids and antibiotics (See Example 5). Other types of NMR spectral data that could be used are $^1$H, $^{17}$O, $^{19}$F, and $^{31}$P data, depending on the endpoint and the structures of the training set compounds.

Another potential way to improve CoSCoSA models is to incorporate multiple structures so that flexible compounds can be modeled (see, Example 8). For example, a 4D-connectivity matrix can be made as a sum of 100 3D-connectivity matrices. In the 4D-connectivity matrix the chemical shifts of atom i and atom j will not change but the distance between atom i and atom j will fluctuate. A score of 100 in a 4D-connectivity matrix will represent unvarying distances between two atoms as seen in bonds and rigid molecules. For flexible molecules there will a distribution of distance hits along the z-axis varying from 1 to some maximum. The distributions will be gaussian or skewed-guassian shaped when there is one maximum distance. When there is more than one maximum other distribution shapes may be used.

Example 4

Estrogen Receptor Binding CoSCoSA Model

In this example, simulated 2D $^{13}$C—$^{13}$C COSY NMR spectral data are used to develop a model for 130 diverse compounds whose relative binding affinities (RBA) to the estrogen receptor are known (Table 10 below). The 2D $^{13}$C—$^{13}$C COSY NMR spectra were formed by using the NMR spectral assignments for predicted carbon chemical shifts to identify nearest neighboring carbon atoms and establish carbon-to-carbon through-bond connectivity spectral patterns of each compound. For the large number of estrogens, a CoSCoSA multiple linear regression (MLR) model using 18 bins selected from the $^{13}C$—$^{13}C$ COSY spectral data had an $r^2$ of 0.83, a leave-one-out cross-validation ($q_1^2$) of 0.77, a leave-13-out cross-validation average ($q_{13}^2$) of 0.76, and a leave-26-out cross-validation average ($q_{26}^2$) of 0.75. A second CoSCoSA model using 17 bins selected from the $^{13}C$—$^{13}C$ COSY spectral data plus one additional distance-related 3D constraint had an $r^2$ of 0.84, a $q_1^2$ of 0.78, an average $q_1^{32}$ of 0.78, and an average $q_{26}^2$ of 0.76. The predictions for 27 test compounds had $q_{pred}^2$ of 0.60 for one CoSCoSA model. The averaged predictions from CoSCoSA and CoMFA models of both internal (training) and external (test) data sets had better explained correlations with strong binding estrogenic compounds than individually by either CoMFA or CoSCoSA model predictions.

TABLE 10

| Name | Exp. Log(RBA) | 18 Bin CoSCoSA Log(RBA) | 17 Bin + L$_{<7.5Å}$ CoSCoSA Log(RBA) |
|---|---|---|---|
| Diethylstillbesterol | 2.6 | 1.52 | 1.51 |
| meso-hexestrol | 2.48 | 2.80 | 2.67 |
| ethinyl estradiol | 2.28 | 1.52 | 1.51 |
| 4-hydroxyestradiol | 2.24 | 2.52 | 2.45 |
| 4-hydroxytamoxifen | 2.24 | 0.58 | 0.58 |
| 17β-estradiol | 2 | 2.08 | 1.53 |
| α-zearalenol | 1.63 | 0.51 | 0.51 |
| ICI182780 | 1.57 | 1.51 | 1.53 |
| dienestrol | 1.57 | 1.52 | 1.51 |
| α-zearalanol | 1.48 | 0.51 | 0.51 |
| 2-hydroxyestradiol | 1.47 | 1.19 | 1.26 |
| diethylstilbestrol monomethyl ether | 1.31 | 1.52 | 1.51 |
| 3,3'-dihydroxyhestrol | 1.19 | 0.79 | 0.68 |
| droloxifene | 1.18 | 1.59 | 1.58 |
| dimethylstibestrol | 1.16 | −0.07 | −0.05 |
| ICI164384 | 1.16 | 1.51 | 1.53 |
| moxestrol | 1.14 | 1.52 | 1.51 |
| 17-deoxyestradiol | 1.14 | 0.18 | 0.35 |
| 2,6-dimethylhexestrol | 1.11 | 0.71 | 0.61 |
| estriol | 0.99 | 0.18 | 0.35 |
| monomethyl ether hexestrol | 0.97 | 0.50 | 0.94 |
| estrone | 0.86 | 0.18 | 0.35 |
| p-meso-phenol | 0.6 | 1.35 | 1.20 |
| 17α-estradiol | 0.49 | 0.75 | 0.35 |
| dihydroxymethoxychlorolefin | 0.42 | −0.11 | −0.11 |
| mestranol | 0.35 | 1.52 | 1.51 |
| zearalanone | 0.32 | 0.51 | 0.51 |
| tamoxifen citrate | 0.21 | 0.58 | 0.58 |
| toremifene citrate | 0.14 | 0.58 | 0.58 |
| α,α-dimethylbethyl allenolic acid | −0.02 | −0.04 | −0.06 |
| coumestrol | −0.05 | 0.75 | 0.35 |
| 4-ethyl-7-OH-(p-meoxyphenol)-dihydro-1-benzopyran-2-one | −0.05 | −1.28 | −1.26 |
| nafoxidine | −0.14 | 0.58 | 0.58 |
| clomiphene citrate | −0.14 | −0.42 | −0.41 |
| 1,3,5-Estratrien-3, 6α-17β-triol | −0.15 | 0.45 | 0.52 |
| β-zearalanol | −0.19 | 0.51 | 0.51 |
| 3-OH-estra-1,3,5-trien-16-one | −0.29 | −0.55 | −0.20 |
| 3-deoxyestradiol | −0.3 | −1.31 | −1.38 |
| 3,6,4'-trihydroxyflavone | −0.35 | −0.33 | −0.31 |
| genistein | −0.36 | −1.62 | −1.60 |
| 4,4'-dihroxystilbene | −0.55 | −0.63 | −0.57 |
| dihydroxymethoxychlor (HPTE) | −0.6 | −1.51 | −1.53 |
| monohydroxymethoxychlorolefin | −0.63 | −0.11 | −0.11 |
| 2,3,4,5-tetraCl-4'-biphenylol | −0.64 | −1.64 | −1.56 |
| norethynodrel | −0.67 | −2.64 | −2.56 |
| 2,2',4,4'-tetrahydroxybenzil | −0.68 | −0.80 | −0.81 |
| β-zearalenol | −0.69 | 0.51 | 0.51 |
| 4,6-dihydroxyflavone | −0.82 | −2.08 | −2.04 |
| equol | −0.82 | −0.39 | 0.5 |
| monohydroxymethoxychlor | −0.89 | −2.08 | −2.04 |
| 3β-androstanediol | −0.92 | −2.64 | −2.56 |
| bisphenol B | −1.07 | −2.64 | −2.56 |
| phloretin | −1.16 | −0.80 | −0.81 |
| dietheylstilbestrol dimethyl ether | −1.25 | −0.49 | −0.48 |
| 2',4,4'-trihydroxychalcone | −1.26 | −1.72 | −1.68 |
| 2,5-dichloro-4'-biphenylol | −1.44 | −1.64 | −1.56 |
| 4,4'-(1,2-ethanediyl)bisphenol | −1.44 | −2.64 | −2.56 |
| 17β-estradiol-16β-OH-16-methyl-3-ether | −1.48 | −1.87 | −1.00 |
| aurin | −1.5 | −0.63 | −0.57 |
| nordihydroguariareticacid | −1.51 | −2.64 | −2.56 |
| 4-nonylphenol | −1.53 | −1.64 | −1.56 |
| apigenin | −1.55 | −1.05 | −1.08 |
| kaempferol | −1.61 | −2.64 | −2.56 |
| daidzein | −1.65 | −1.64 | −1.56 |
| 3-methylestriol | −1.65 | −1.87 | −1.90 |
| 4-dodecylphenol | −1.73 | −2.64 | −2.56 |
| 2-ethylhexyl-4-hydroxybenzoate | −1.74 | −2.64 | −2.56 |
| 4-tert-octylphenol | −1.82 | −2.64 | −2.56 |
| phenolphthalein | −1.87 | −1.51 | −1.53 |
| kepone | −1.89 | −2.64 | −2.56 |
| heptyl-4-hydroxybenzoate | −2.09 | −2.64 | −2.56 |
| bisphenol A | −2.11 | −2.64 | −2.56 |
| naringenin | −2.13 | −2.64 | −2.56 |
| 4-Cl-4'-biphenylol | −2.18 | −2.64 | −2.56 |
| 3-deoxyestrone | −2.2 | −1.31 | −1.38 |
| 4-octylphenol | −2.31 | −2.64 | −2.56 |
| fisetin | −2.35 | −2.14 | −2.06 |
| 3',4',7-trihydroxyisoflavone | −2.35 | −2.64 | −2.56 |
| biochanin A | −2.37 | −1.62 | −1.60 |
| 4-OH-chalcone | −2.43 | −2.64 | −2.56 |
| 4'-OH-chalcone | −2.43 | −2.64 | −2.56 |
| 2,2'-methylenebis(4-chlorophenol) | −2.45 | −2.08 | −2.04 |
| 4,4'-dihydroxybenzophenone | −2.46 | −2.64 | −2.56 |
| benzyl-4-hydroxybenzoate | −2.54 | −2.64 | −2.56 |
| 2,4-dihydroxybenzophenone | −2.61 | −2.64 | −2.56 |
| 4'-hydroxyflavanone | −2.65 | −3.20 | −2.98 |
| 3α-androstanediol | −2.67 | −2.64 | −2.56 |
| 4-phenethylphenol | −2.69 | −2.64 | −2.56 |
| prunetin | −2.74 | −2.64 | −2.56 |
| doisynoestrol | −2.74 | −2.14 | −2.07 |
| myricetin | −2.75 | −2.64 | −2.56 |
| 2-Cl-4-biphenylol | −2.77 | −3.21 | −2.56 |
| triphenylethylene | −2.78 | −2.64 | −2.56 |
| 3'-OH-flavanone | −2.78 | −3.43 | −3.27 |
| chalcone | −2.82 | −2.64 | −2.56 |
| o,p',-DDT | −2.85 | −2.64 | −2.56 |
| 4-heptyloxyphenol | −2.88 | −2.64 | −2.56 |
| dihydrotestosterone | −2.89 | −2.64 | −2.56 |
| formononetin | −2.98 | −2.64 | −2.56 |
| bis-(4-hydroxyphenyl)methane | −3.02 | −2.64 | −2.56 |
| p-phenylphenol | −3.04 | −2.64 | −2.56 |
| 6-hydroxyflavanone | −3.05 | −2.14 | −2.06 |
| 4,4'-sulfonyldiphenol | −3.07 | −1.51 | −1.53 |
| butyl-4-hydroxybenzoate | −3.07 | −2.64 | −2.56 |
| diphenolic acid | −3.13 | −2.64 | −2.56 |
| 1,3-diphenyltetramethyldisiloxane | −3.16 | −2.64 | −2.56 |
| propyl-4-hydroxybenzoate | −3.22 | −3.51 | −3.51 |
| ethyl-4-hydrobenzoate | −3.22 | −3.51 | −3.51 |
| phenol red | −3.25 | −2.64 | −2.56 |
| 3,3',5,5'-tetraCl-4,4'-biphenyldiol | −3.25 | −2.64 | −2.56 |
| 4-tert-amylphenol | −3.26 | −2.64 | −3.71 |
| baicalein | −3.35 | −2.64 | −2.56 |
| morin | −3.35 | −2.64 | −2.56 |
| 4-sec-butyiphenol | −3.37 | −2.08 | −2.04 |
| 4-Cl-3-methylphenol | −3.38 | −2.64 | −3.71 |
| 6-hydroxyflavone | −3.41 | −2.64 | −2.56 |
| 4-benzyloxyphenol | −3.44 | −2.64 | −2.56 |
| 3-phenylphenol | −3.44 | −2.14 | −2.06 |
| methyl-4-hydrobenzoate | −3.44 | −2.64 | −3.71 |
| 2-sec-butylphenol | −3.54 | −3.14 | −2.94 |
| 2,4'-dichlorobiphenyl | −3.61 | −2.64 | −2.56 |

TABLE 10-continued

| Name | Exp. Log(RBA) | 18 Bin CoSCoSA Log(RBA) | 17 Bin + $L_{<7.5Å}$ CoSCoSA Log(RBA) |
|---|---|---|---|
| 4-tert-butylphenol | −3.61 | −3.78 | −3.71 |
| 2-Cl-4-methylphenol | −3.66 | −2.64 | −3.71 |
| phenolphthalin | −3.67 | −2.64 | −2.56 |
| 4-Cl-2-methylphenol | −3.67 | −2.64 | −3.71 |
| 7-hydroxyflavanone | −3.73 | −2.64 | −2.56 |
| 3-ethylphenol | −3.87 | −2.92 | −3.92 |
| rutin | −4.09 | −3.51 | −3.51 |
| 4-ethylphenol | −4.17 | −3.78 | −3.71 |
| 4-methylphenol | −4.5 | −3.78 | −3.71 |

Column 1 is the name of the compound, column 2 is the Exp Log(RBA), column 3 is the predicted Log (RBA) from the 18 bin CoSCoSA model, and column 4 is the predicted log (RBA) from the 17 Bin + $L_{<7.5Å}$ CoSCoSa model.

The log relative binding activity (RBA) data for these 130 structurally diverse compounds was used to train the CoSCoSA models. The data was produced at NCTR using a competitive ER binding assay with radiolabeled estradiol ($[^3H]E_2$) in rat uterine cytosol, which was obtained from ovariectomized uteri of Sprague-Dawley rats. This data set spanned 7 orders in magnitude, ranging from a log (RBA) value of 4 for a weak estrogen receptor binder, to a log (RBA) of 2 for a strong estrogen receptor binder. For a particular molecule, the relative binding affinity (RBA) to the estrogen receptor is defined as one hundred times the ratio of the molar concentrations of 17-β-estradiol and the competing compound required to decrease the amount of receptor-bound 17-β-estradiol by 50%. Thus 17-β-estradiol had an RBA of 100 and a base ten log(RBA) of 2.0. For each of the 130 compounds, the $^{13}C$ 2D $^{13}C$—$^{13}C$ COSY NMR experiment was simulated using the ACD Labs CNMR version 5.0 2D predictor software. The COSY NMR spectra could be saved as two tables per compound. One table showed the assigned carbon chemical shifts and the other indicated through-bond coupling of nearest neighbor carbon atoms. The use of predicted rather than experimentally measured NMR chemical shifts was not necessary for developing the CoSCoSA models, but it saved time and expense. Additionally, the use of $^{13}C$ NMR spectra, each based on the same edition of prediction software (rather than collected from spectral libraries or other sources) eliminated random variability due to the NMR solvent or other experimental factors.

The 2D $^{13}C$—$^{13}C$ COSY spectra were predicted for the compounds. The resolution of all 2D $^{13}C$—$^{13}C$ COSY spectra was reduced by defining bins, 2.0 parts per million (ppm) wide in both dimensions. The inherent resolution of NMR is much greater than this, but any signal appearing within a 2.0 ppm bin was counted toward the bin population. This choice was made so that many of the bins would be multiply populated, a characteristic that is advantageous for statistical analysis and model validation. The use of such wide bins also reduced the confounding effects on the modeled patterns caused by uncertainties or errors in simulated spectra. The specific 2.0 ppm value was chosen because that bin width was used successfully in other CoSCoSA models. Possible improvements in model efficacy through use of somewhat wider or narrower bins are possible. The generally excellent results reported below for this modeling approach probably leave some room for improvement from optimization of this factor alone.

The spectra were saved as two-dimensional bins under the peak within a certain spectral range, and normalized to an integer. A single carbon-to-carbon connectivity was assigned an area of 100, two carbon-to-carbon connections in a bin had an area of 200, and so forth. Occupancy of the 120-126 ppm spectral bin represents the same spectral connectivity relationship as that in the 126-120 ppm bin since the data are symmetric across the diagonal of the spectral plane. In this example, the 2 ppm bins are denoted by the format a-b, where a and b are the ppm values corresponding to the two "connected" atoms. For this reason, the 240 ppm by 240 ppm 2D spectral plane was consolidated into 7381 2 ppm×2 ppm bins, meaning only those bins above and including the diagonal were used. After binning all 130 compounds, only 605 bins from the 7381 bins had "hits" in them. Of the 605 populated bins only 337 bins had more than one "hit". From the remaining 337 multiply populated bins, an increasing number of the mostly highly correlated bins were selected by trial and error and used to construct multiple linear regression (MLR) models until a model was obtained that had an $r^2$ greater than 0.8 and an F-test value greater than 30. 17 bins were identified in this way, and one more bin was defined by grouping the data into a single, larger bin that joined 3 one-"hit" bins that were adjacent to each other. The addition of this one bin represented a manual-binning algorithm based on data inspection, but once defined was applied uniformly to the spectral representation of all compounds. This grouped bin was only populated in the case of three compounds, all weak binders that all had a log (RBA) lower than −3.22. The addition of this grouped bin improved the $r^2$ of the model by less than 2 percent.

The predicted NMR spectra were calculated using the substructure similarity technique HOSE, which correlates similar structures with similar NMR chemical shifts. Therefore, the errors produced in the simulated NMR spectra were propagated through the similar structures found in the training set of the QSDAR models. This conveniently reduced the effective error.

All statistical analysis was performed by Statistica version 6.0 software (StatSoft, Tulsa, Okla.). For each CoSCoSA model, forward multiple linear regression (MLR) was used on a selected subset of spectral bins until the model had an $r^2$ greater than 0.82. No bins with less than 2 "hits" were selected. The reason for this is that a bin with one "hit" can inappropriately add to the $r^2$ of a model but can not improve the leave-one-out cross-validation ($q_1^2$) of a model. The use of a large number of very small, singly populated bins is the reason that other techniques of using spectral data as descriptors have a high $r^2$ and very low $q_1^2$ (Bursi et al., "Comparative Spectral Analysis (CoSA): Spectra as three-dimensional molecular descriptors for the prediction of biological activities, *J. Chem. Inf. Comput. Sci.*, 39: 861-867, 1999).

Evaluations of the CoSCoSA models were done using leave-one-out (LOO) or leave-multiple-out cross-validation procedures in which one or more compounds were systematically excluded from the training set, and each developed model (missing any contribution from the excluded compound(s) was used to predict binding activities of the excluded compounds. The cross-validated $r^2$ (termed $q_1^2$) that results from fitting predictions obtained by cross-validation experiments can be derived from $q_1^2 = 1 - PRESS/SSD$. Here PRESS is the sum of the differences between the actual and predicted activity data for each molecule during LOO cross-validation, and SSD is the sum of the squared deviations between the measured and mean activities of each molecule in the training set. During the LOO cross-validation, each compound was removed from the training and the Beta-coefficients in the MLR equation were recalculated. This new MLR equation was used to recalculate the log(RBA) of the compound left out. To more rigorously test the validity of the CoSCoSA models, two leave-13-out (10% of the data excluded) and two leave-26-out (20% of the data excluded) cross-validations were performed on each of the models. In these "leave-multiple-samples-out" experiments, the compounds omitted were varied and the results of the two corresponding experiments were averaged.

Additionally, to further test the ruggedness of CoSCoSA models, the log(RBA)s of compounds from two published external data sets were predicted, namely those of Waller et al. (Waller et al, "Ligand-based identification of environmental estrogens," *Chem. Res. Toxicol.*, 9: 1240-1248, 1996) and Kuiper et al. (Kuiper et al., "Comparison of athe ligand binding specificity and transcript tissue distribution of estrogen receptors α and β, *Endocrinology*, 138: 863-870, 1997). The log(RBA)s from these external data sets possessed a greater variability in binding activity. So, a set of compounds that had their binding activity determined by all three methods (Waller, Kupier, and NCTR) were used to normalize the external data sets to the NCTR data. The CoSCoSA models were made using the resulting MLR equations to predict the log(RBA) of the compounds in the test set. Normalized log (RBA) for 27 compounds from Waller and Kuiper data were used for external testing of the CoSCoSA models. However, many of the occupied bins for the new compounds from the external data set did not fall into the original 605 occupied bins. (The original set of bins comprised only 8.2% of the 2D COSY spectral plane.) In the different molecular contexts of the external data sets, it is possible that NMR chemical shift information was expressed in adjacent but non-included bins since NMR chemical shifts exist along a continuum, and the process of binning them for this type of pattern recognition may miss a signal for a smaller bin size.

To account for this source of confusion with the external data, we tried adding various fractions of "near-miss" signals into each compound's spectrum. With this in mind we used the CoSCoSA model's MLR equation to predict the normalized log(RBA) of the compounds in the external test set. However, compounds from the external test set with bins that were one bin away (one of 8 bins surrounding a 2D bin) from the original 605 populated bins were modeled using none, one-quarter, and one-half of that bin's intensity in the nearest neighboring bin used in the original CoSCoSA model.

Figure 10:
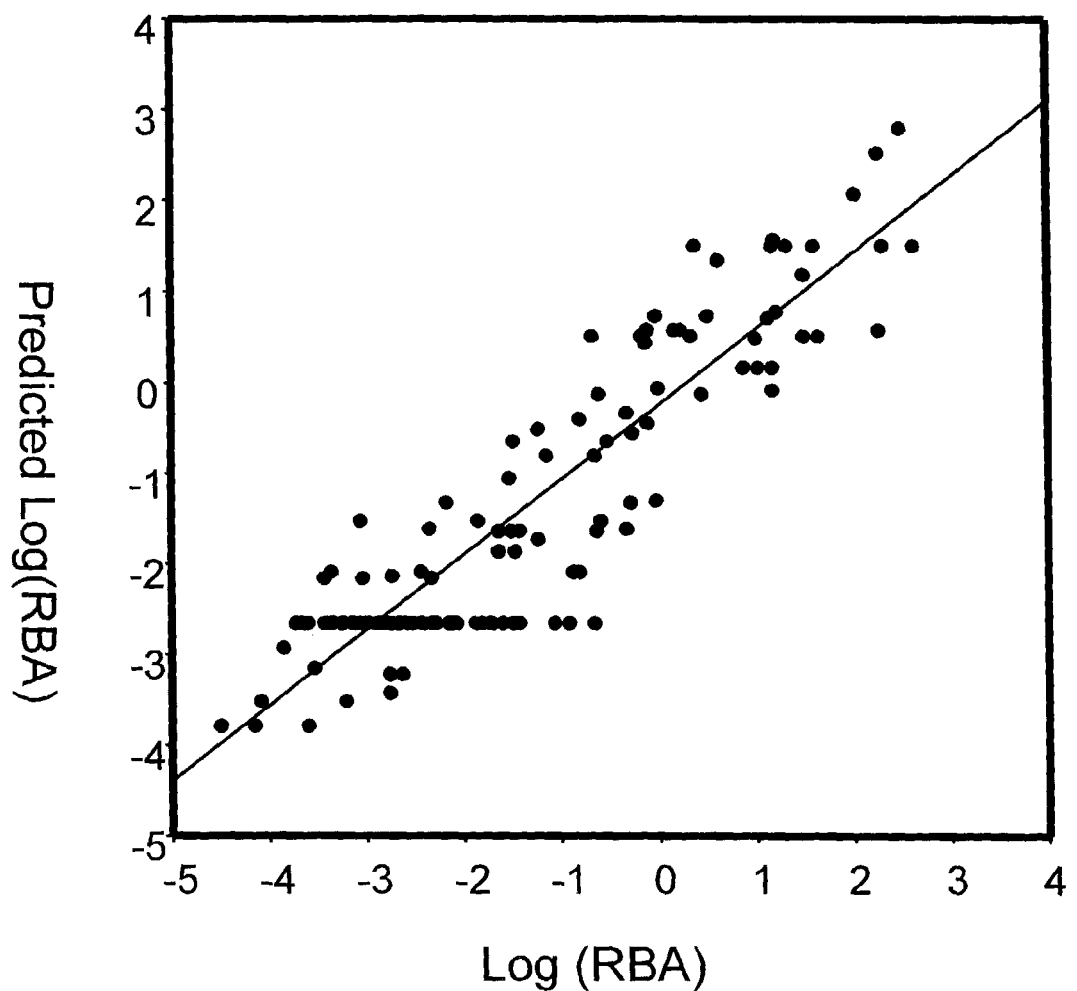
FIG. 10 is a graph of the predicted log (RBA) versus experimental log (RBA) based on 18 COSY spectral bins obtained for a CoSCoSA model of estrogen receptor binding.

FIG. 10 shows the CoSCoSA model that was based on the MLR analysis of 18 selected 2D bins from the $^{13}C-^{13}C$ COSY spectral data. The 18 bin COSY model for the 130 estrogenic compounds had an explained variance ($r^2$) of 0.83, a leave-one-out (LOO) $q_1^2$ of 0.77, an average leave-13-out cross-validated variance ($q_1^2$) of 0.76±0.01, and an average leave-26-out cross-validated variance ($q_{26}^2$) of 0.75±0.01. The CoSCoSA model was based on COSY bins 28-12, 68-16 (grouped bin), 36-24, 72-20, 54-28, 50-38, 64-56, 158-94, 164-104, 152-108, 156-110, 140-112, 142-112, 154-112, 154-114, 156-114, 128-116, and 126-120. All bins had more than three "hits" in the bin except for bins 152-108 and 140-112 that had only two "hits" each. The correlation matrix for the 18 bins were calculated and only two sets of bins had correlation between them that were greater than 0.5. The greatest average correlation between any bin with the other 17 bins was 0.04 and many of the average correlations were much lower than 0.04. The lack of a large correlation among bins suggests that the resulting patterns were based on essentially orthogonal data. The COSY bin 28-12 was most often associated with the $CH_3$ carbon connected to the $CH_2$ in the ethyl groups in DES and hexestrol-like compounds. Twelve of the fourteen compounds with a COSY hit in 28-12 had a log(RBA) greater than −0.05. Compounds that populated a COSY bin at 154-112 were most often associated with the 3 carbon position connected to the 2 carbon position in the A-ring of 17-O-estradiol like compounds. Nine of the ten compounds with a COSY hit in bin 154-112 had a log(RBA) greater than −0.05. Fourteen compounds had a "hit" in the COSY bin at 128-116. The 128-116 COSY bin was most often associated with the 2 to 3 and 5 to 6 carbon positions in a phenol ring. Twelve of the fourteen compounds with a COSY hit in bin 128-116 had a log(RBA) less than 0.60. The 24 compounds that had a hit or multiple hits in the COSY bin at 156-114 was most often associated with the hydroxylated carbon of a phenol ring connected to its two nearest neighboring carbons. Only 5 of the 24 compounds with a COSY hit in bin 156-114 had a log(RBA) less than −1.65. The 6 compounds that had a COSY bin at 64-56 was most often associated with the two carbons between the oxygen ester and the nitrodimethyl of tamoxifen-like compounds. Similar spectral-structural associations could be made for the other COSY bins used for receptor binding prediction in the CoSCoSA models.

Figure 11:
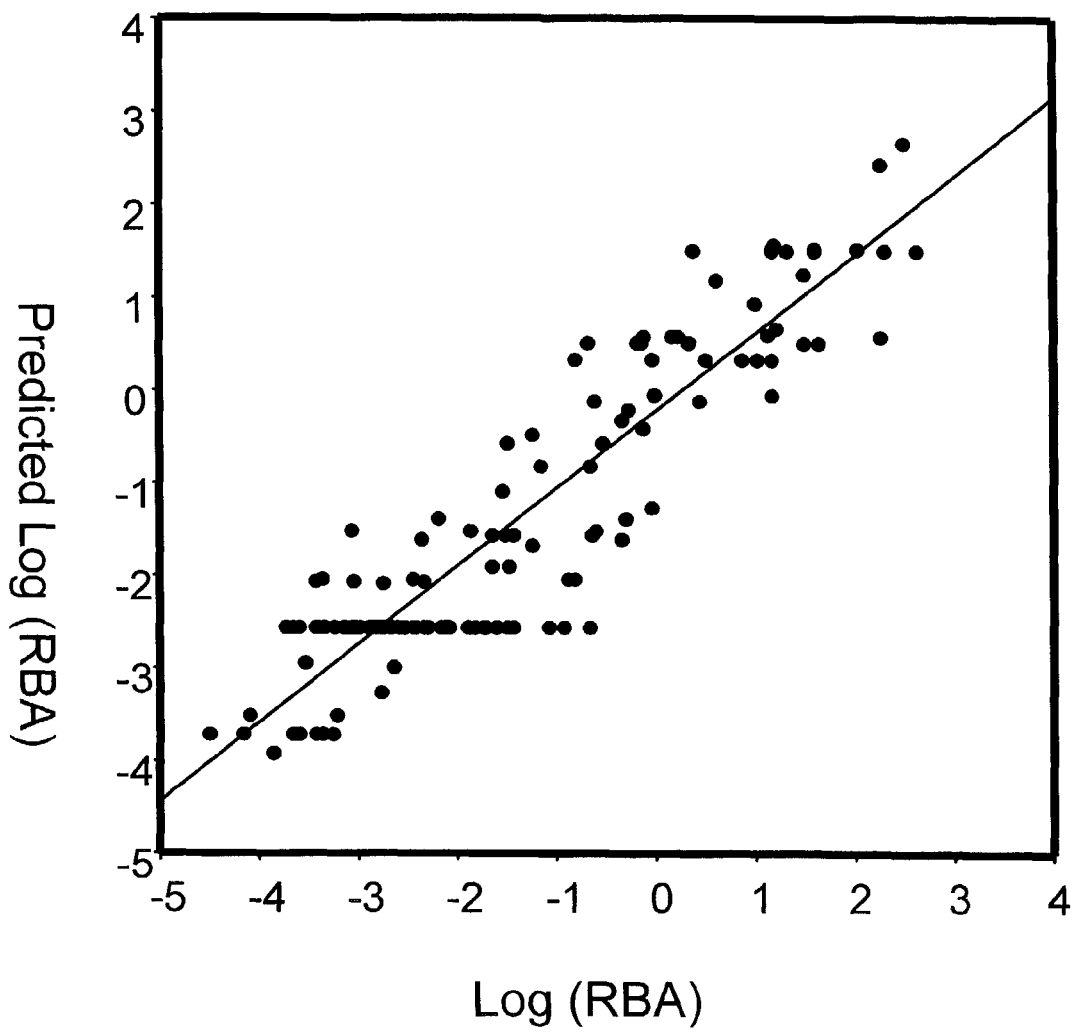
FIG. 11 is graph of the predicted log (RBA) versus experimental log (RBA) based on 17 COSY spectral bins plus the $L_{<7.5 Å}$ variable obtained for a CoSCoSA model of estrogen receptor binding.

FIG. 11 shows results for the CoSCoSA model that was based on the MLR analysis of 17 selected 2D $^{13}C-^{13}C$ COSY bins plus the one distance variable. The distance variable, $L_{<7.5 Å}$, was assigned a value of 1 when the maximum distance between non-hydrogen atoms in a compound was less than 7.5 Å (compact) and a value of zero for all other compounds. The $L_{<7.5}$ Å variable replaced the COSY bin at 154-114 in the previous 18 bin CoSCoSA model. This 17 bin-with-$L_{<7.5 Å}$ model had an $r^2$ of 0.84, a $q_1^2$ of 0.78, an average $q_1^{32}$ of 0.76±0.01, and an average $q_{26}^2$ of 0.769±0.01. In this model, the $L_<7.5$ Å variable selected 9 compounds all of which had a log (RBA) lower than −3.26. Smaller, compact molecules tended to bind weakly.

In FIGS. 10 and 11, the line of compounds predicted to have a log(RBA) of −2.60 is a set of compounds that did not have a hit in any of the 18 bins used to formulate the two CoSCoSA models. The removal of these compounds from the models did not change the $r^2$ or $q^2$ of the model more than 2%. Almost all of the compounds with no hits in the 18 bins had experimental log(RBA) lower than −1.0. The CoSCoSA models did not find a spectral relationship for these weakly binding compounds to the estrogen receptor. Most of the other bins in both CoSCoSA models were used to form a relationship between a spectral bin and binding to the estrogen receptor with a log(RBA) stronger than −2.60.

Table 11 summarizes predictions for 21 compounds from the Waller et al. data set using both the 18 bin and 17 bin-plus-$L_{<7.5 Å}$ model of estrogen binding. To make the predictions, simulated the 2D spectra of the 21 compounds were calculated, again using ACD Labs CNMR version 5.0 2D predictor software. The simulated spectra of the test set were binned into the same 605 bins. However, many of the occupied bins for these compounds did not fall into the original 605 occupied bins (that represent only 8.2% of the 2D COSY spectral plane). Therefore, if the simulated spectra did not fall into one of the original 605 populated bins, none, one-quarter, and one-half of the bin's intensity was put into the neighboring bin or bins used in the CoSCoSA model. The CoSCoSA models were made and the resulting MLR equation was used to predict the log(RBA) of the compounds in the test set. Only 6 of the 27 compounds from the Waller et al. and Kuiper et al. external data sets had binned COSY chemical shifts that were not in the original 605 bins and that bin that was within one bin of those 18 bins used to formulate a CoSCoSA model. In Table 1, for these 6 compounds, the predicted log(RBA) using one-quarter intensity in a neighboring bin and plus or minus the deviation seen when predicting the Log(RBA) when using none and one-half intensity in the neighboring bin was used for a CoSCoSA model. For the Waller et al. test set and one quarter of a bin's intensity in neighboring bins a $q_{pred}^2$ of 0.47 for the 18 bin CoSCoSA model and a $q_{pred}^2$ 0.61 for the 17 bin-plus-$L_{<7.5\ \text{Å}}$ CoSCoSA model was achieved. When using one half of a bin's intensity in a neighboring bin a $q_{pred}^2$ of 0.40 was seen for the 18 bin CoSCoSA model and a $q_{pred}^2$ 0.53 for the 17 bin-plus-$L_{<7.5\ \text{Å}}$ CoSCoSA model. Using none of a bin's intensity in a neighboring bin a $q_{pred}^2$ of 0.40 for the 18 bin CoSCoSA model and a $q_{pred}^2$ of 0.47 for the 17 bin-plus-$L_{<7.5\ \text{Å}}$ CoSCoSA model was seen.

TABLE 11

| Name | Normalized log (RBA) | 18-CoSASA | 17 + $L_{<7.5\text{Å}}$-CoSCoSA | CoMFA |
|---|---|---|---|---|
| 2-tert-butylphenol | −4.55 | −2.64 | −3.71 | −3.83 |
| 3-tert-butylphenol | −4.82 | −1.43 ± 0.70 | −2.48 ± 0.70 | −3.33 |
| 2,4,6,-triCl-4'-biphenylol | −0.16 | −1.64 | −1.56 | −1.60 |
| 2-Cl-4,4'-biphenyldiol | −0.61 | −1.64 | −1.56 | −1.49 |
| 2,6-dichloro-4'-biphenylol | −1.11 | −1.64 | −1.56 | −2.41 |
| 2,3,5,6,tetraCl-4,4'-biphenyldiol | −2.18 | −1.64 | −1.56 | −0.82 |
| 2,2',3,3',6,6'-hexaCl-4-biphenylol | −2.74 | −2.14 | −2.06 | −3.06 |
| 2,2',3,4',6,6'-hexaCl-4-biphenylol | −2.60 | −1.64 | −1.56 | −2.48 |
| 2,2',3,6,6'-pentaCl-4-biphenylol | −1.97 | −1.64 | −1.56 | −3.07 |
| 2,2'5,5'-tetraCl-biphenyl | −2.67 | −2.64 | −2.56 | −2.74 |
| 2,2',4,4',5,5'-heaxCl-biphenyl | −2.83 | −2.64 | −2.56 | −1.52 |
| 2,2',4,4',6,6'-hexaCl-biphenyl | −1.87 | −2.64 | −2.56 | −1.83 |
| 2,2',3,3',5,5'-heaxCl-6'-biphenylol | −2.69 | −2.36 | −2.30 | −3.01 |
| 4'-deoxyindenestrol | −1.371 | −0.86 ± 0.71 | −0.79 ± 0.72 | −0.53 |
| 4'-deoxyindenestrol | −0.230 | −0.86 ± 0.71 | −0.79 ± 0.72 | 0.111 |
| 5'-deoxyindenestrol | −0.588 | −0.57 | −0.52 | −1.00 |
| 5'-deoxyindenestrol | 0.35 | −0.57 | −0.52 | −0.59 |
| Indenestrol A (R) | 1.08 | 0.85 ± 1.41 | 0.93 ± 1.45 | 0.29 |
| Indenestrol A (S) | 2.39 | 0.85 ± 1.41 | 0.93 ± 1.45 | 0.62 |
| R 5020 | −1.81 | −4.96 | −4.97 | −0.70 |
| Zearalenone | 0.91 | 0.51 | 0.51 | −0.12 |
| 5-Androstenediol | −0.49 | −2.64 | −2.56 | −0.66 |
| 16a-bromoestradiol | 1.41 | 0.18 | 0.35 | 0.33 |
| 16-ketoestradiol | −0.38 | 0.18 | 0.35 | 0.58 |
| 17-epi-estriol | 0.98 | 0.18 | 0.35 | −0.16 |
| 2-OH-estrone | −0.19 | 1.19 | 1.26 | 0.36 |
| Raloxifene | 1.34 | 0.99 ± 1.41 | 0.31 ± 0.73 | −0.24 |

Column 2 shows the experimental log(RBA) values for binding to the estrogen receptor for each compound. In column 3 are found the predicted log(RBA)s from the 18 bin 2D-CoSCoSA model; column 4, the predicted log(RBA)s from the 17 bin plus $L_{<7.5\text{Å}}$ CoSCoSA model; and in column 5, the predicted log(RBA)s from the CoMFA model (38). The plus and minus sign reveals the variation seen when using none and one-half of a bin's intensity in a neighboring bins usedto formulate the CoSCoSA model.

Although the two CoSCoSA models had an $r^2$ of 0.83 and 0.84, respectively, the leave-one-out cross-validations of the models were always above 0.77. The cross-validations of both CoSCoSA models remained consistently above 0.75 whether they were calculated by leave-one-out, leave-13-out (10% of training set) or leave-26-out (20% of training set). Compared to CoMFA models formed in three-dimensional space, the ruggedness under cross-validation of the CoSCoSA models is related to the fact that the patterns are representations of a "digital-like" occupancy number of two-dimensional bins. This was true not only for the COSY spectral data, but also for the $L_{<7.5\ \text{Å}}$ variable inputted in a "digital-like" yes or no manner. In contrast, a published CoMFA model of the same 130 compounds based on analogue estimates of electric field spatial distributions, had a remarkably good $r^2$ of 0.91 but much less impressive cross-validation results: $q_1^2$ of 0.66, a mean $q_{13}^2$ of 0.65, and a mean $q_{26}^2$ of 0.62. The large falloff in CoMFA model quality under cross-validation indicates the extent to which the model was based on non-linear relationships among the input training data. By using semi-digital data representations and basing our 2D-CoSCoSA models only on multiply populated bins, some of the non-linear relationships are presumably removed.

For the 21 compounds in the Waller et al. test set, the 18 bin CoSCoSA model had a $q_{pred}^2$ of 0.47 and the 17 bin-plus-$L_{<7.5\ \text{Å}}$ CoSCoSA model had a $q_{pred}^2$ of 0.61. When two outliers (3-tert-buytlphenol and R 5020) were removed, the CoSCoSA models using one-quarter of a bin's intensity in neighboring bins used in a CoSCoSA model had a $q_{pred}^2$ increased to 0.79 and 0.84, respectively. A CoMFA model had a $q_{pred}^2$ of 0.70 for Waller et al. test set.

Log(RBA) predictions were made for 6 compounds from the Kuiper et al. data set that had known experimental log (RBA) greater than −1.0 (shown in Table 1 rows 22 to 27). The 14 compounds from Kuiper's and Waller's data with log (RBA) stronger than −1.0 to were selected make predictions. For these stronger binders, using one-quarter of a bin's intensity in neighboring bins resulted in a $q_{pred}^2$ of 0.41 for the 18 bin CoSCoSA model and a $q_{pred}^2$ of 0.38 for the 17 bin-plus-$L_{<7.5\ \text{Å}}$ CoSCoSA model, while the CoMFA model had a $q_{pred}^2$ of 0.29. When using one half of a bin's intensity in a neighboring bin the 18 bin the CoSCoSA model $q_{pred}^2$ increased to 0.54 for, and for the 17 bin-plus-$L_{<7.5\ \text{Å}}$ CoSCoSA model, $q_{pred}$ increased to 0.51. When no intensity was used in the neighboring bins, a $q_{pred}^2$ of 0.13 for the 18 bin CoSCoSA model was obtained, and $q_{pred}^2$ of 0.12 for the 17 bin-plus-$L_{<7.5\ \text{Å}}$ CoSCoSA model was obtained. Apparently, for the complete data sets, the CoMFA model achieved a better overall $q_{pred}^2$ because it predicted the lower binding affinity, less biologically relevant, compounds better than the CoSCoSA models. It is significant that the CoSCoSA models were better at predicting tighter binding compounds. It makes sense that the spectral characteristics that can be associated with binding to a well-defined site can also be modeled well, but that there is no single basis for defining a spectral relationship for non-binding.

For the Waller et al. 21 external test compounds, averaging quantitative log(RBA) estimates from the CoMFA model with those from the 17 bin-plus-$L_{<7.5\ \text{Å}}$ CoSCoSA model produced a $q_{pred}^2$ of 0.77, an increase of 0.07 over the CoMFA model's predictions alone. Likewise, when compounds with a log (RBA) greater than −1.0 were selected from the 130 compound training set (weak binders), the $r^2$ of the CoMFA model was 0.65 and the $r^2$ of the 17 bin-plus $L_{<7.5\ \text{Å}}$ CoSCoSA model was 0.61. Where the average of the CoMFA and 17 bin-plus-$L_{<7.5\ \text{Å}}$ CoSCoSA model was used, the resulting values had an $r^2$ of 0.73 for compounds with a log (RBA) greater than −1.0. It appears, at least for estrogen receptor binding and its strong or weak-binding subsets, that the information used to produce CoMFA and CoSCoSA models can be constructively averaged to produce more accurate predictions. In the 2D-CoSCoSA models, the $r^2$ and $q_1^2$ increased with increasing number of bins used in the model. The addition of the one three-dimensional parameter, $L_{<7.5\ \text{Å}}$, increased $r^2$, $q_1^2$, $q_{13}^2$, $q_{26}^2$, by 1 to 2%, and increased the $q_{pred}^2$ by 10% over the 18 bin 2D-CoSCoSA model.

The predictions of binding for the 27 Waller et al. and Kuiper et al. external compounds had a $q_{pred}^2$ of 0.50 for the 18 bin model and $q_{pred}^2$ of 0.60 for the 17 bin-plus-$L_{<7.5\ \text{Å}}$ model when using one quarter intensity of a bin in a neighboring bin for the CoSCoSA model. Similar, but slightly lower predictive results are seen for all 27 compounds when using one half of a bin's intensity in a neighboring bin. When using none of a bin's intensity in a neighboring bin used in the CoSCoSA model a $q_{pred}$ of 0.43 for the 18 bin model and $q_{pred}^2$ of 0.48 for the 17 bin-plus-$L_{<7.5 Å}$ model were obtained. The CoSCoSA model predictions for Indenestrol A and Indenestrol B that had a deviation of 1.41 and 1.45 log (RBA) units due to the different models using none, one-quarter, and one-half of that bin's intensity in the nearest neighboring bin in the CoSCoSA model. This deviation is consistent with the experimental log(RBA) difference in binding activity between Indenestrol A and Indenestrol B of 1.31 log(RBA) units. The average deviation for the other 3 of the 4 compounds, due to the different models using none, one-quarter, and one-half of a bin's intensity, was about 0.72 log(RBA) units.

Example 5

CoSCoSA Model of Cephalosporin Antiobiotic Activity

This example describes the application of the disclosed CoSCoSA methods to model the minimum inhibitory concentration of cephalosporin antibotics, using only the through-bond (COSY-type) connections between carbons and between carbons and nitrogens in their structures. Bin sizes of 3 ppm by 3 ppm for carbon to carbon bins were used, and 10 ppm by 3 ppm for the nitrogen to carbon bins. MLR selected 4 bins, specifically: 135 Carbon-24 Carbon; −230 Nitrogen-156 Carbon; −280 Nitrogen-162 Carbon; and −230 Nitrogen-168 Carbon. The structures of the cephalosporins used in the model are shown below.

Cefaclor

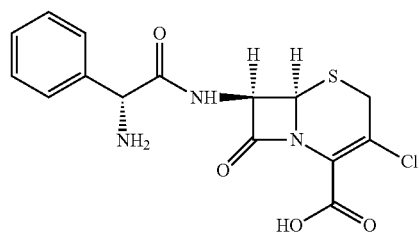

Cefadroxil

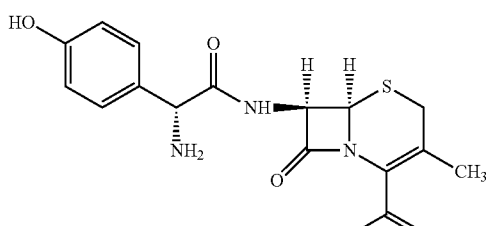

Cefmatazole

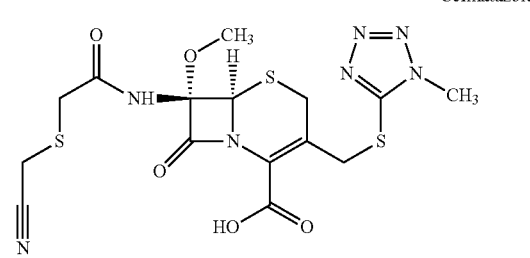

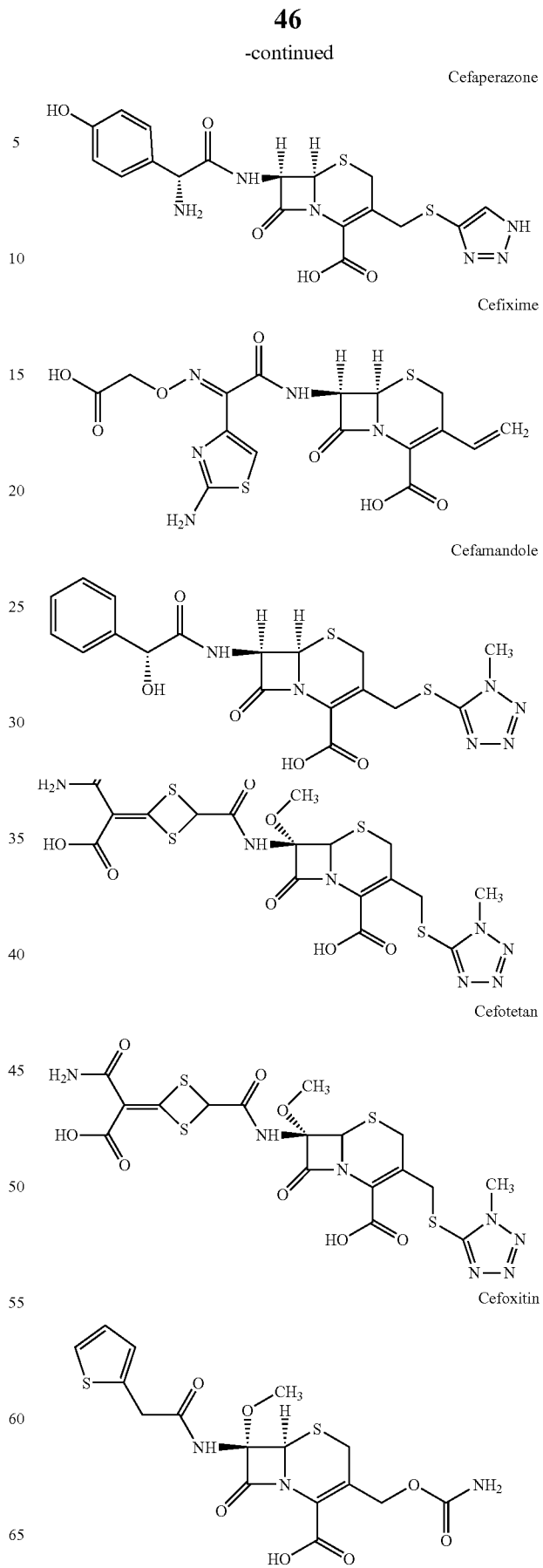

Cefaperazone

Cefixime

Cefamandole

Cefotetan

Cefoxitin

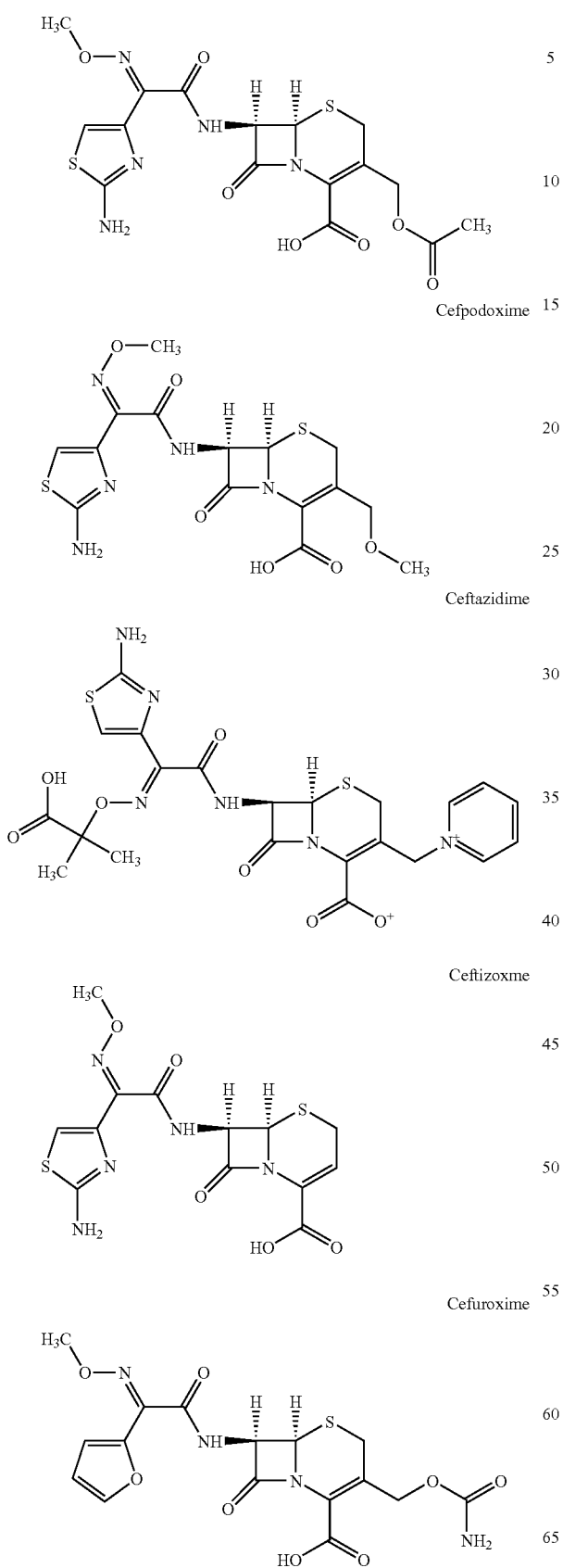
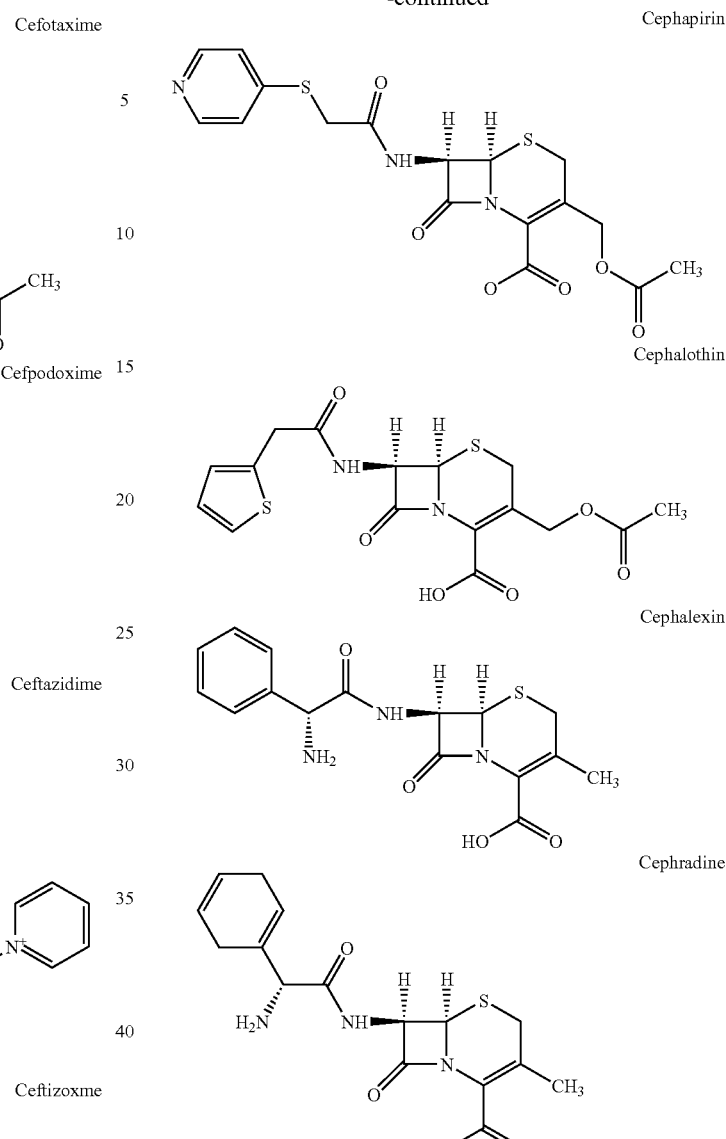

Nitrogen chemical shifts were predicted from software available on the ACD Labs ILAB website. Carbon shifts were predicted as before. In building the Nitrogen to Carbon connectivity matrix, 700 ppm were added to the predicted nitrogen chemical shifts. When 700 ppm was added to the nitrogen chemical shifts the nitrogen chemical shifts fell in the range 300 ppm to 700 ppm, and could be added directly after the carbon to carbon connectivity bins, which ranged from 0 ppm to 240 ppm. The CoSCoSA models were produced as described in previous examples, and the results are shown in Table 12 below.

TABLE 12

| Compounds | MIC | Log(1/MIC) | Leave-1-out Log(1/MIC) Predicted | Leave-4-out Log(1/MIC) Predicted |
|---|---|---|---|---|
| Cefaclor | 8 | −.90 | −1.22 | −1.23 |
| Cefadroxil | 8 | −.90 | −.90 | −.90 |
| Cefamandole | 16 | −1.20 | −1.15 | −1.15 |

TABLE 12-continued

| Compounds | MIC | Log(1/MIC) | Leave-1-out Log(1/MIC) Predicted | Leave-4-out Log(1/MIC) Predicted |
|---|---|---|---|---|
| Cefaperazone | 16 | −1.20 | −1.15 | −1.13 |
| Cefixime | 8 | −.90 | −.88 | −1.20 |
| Cefmetazole | 16 | −1.20 | −1.15 | −1.15 |
| Cefotaxime | 16 | −1.20 | −1.21 | −1.23 |
| Cefotetan | 16 | −1.20 | −1.15 | −1.13 |
| Cefoxitin | 16 | −1.20 | −1.15 | −1.23 |
| Cefpodoxime | 2 | −.30 | −.32 | −.32 |
| Ceftazidime | 16 | −1.20 | −1.21 | −1.23 |
| Ceftizoxime | 8 | −.90 | −.85 | −.83 |
| Cefuroxime | 4 | −.60 | −.63 | −.42 |
| Cephalexin | 8 | −.90 | −.90 | −.90 |
| Cephalothin | 8 | −.90 | −.90 | −.90 |
| Cephapirin | 8 | −.90 | −.90 | −.90 |
| Cephradine | 8 | −.90 | −.90 | −.90 |

Results of Cephalosporin CoSCoSa modeling;
MIC = Minimal Inhibitory Concentration.

Figure 12:
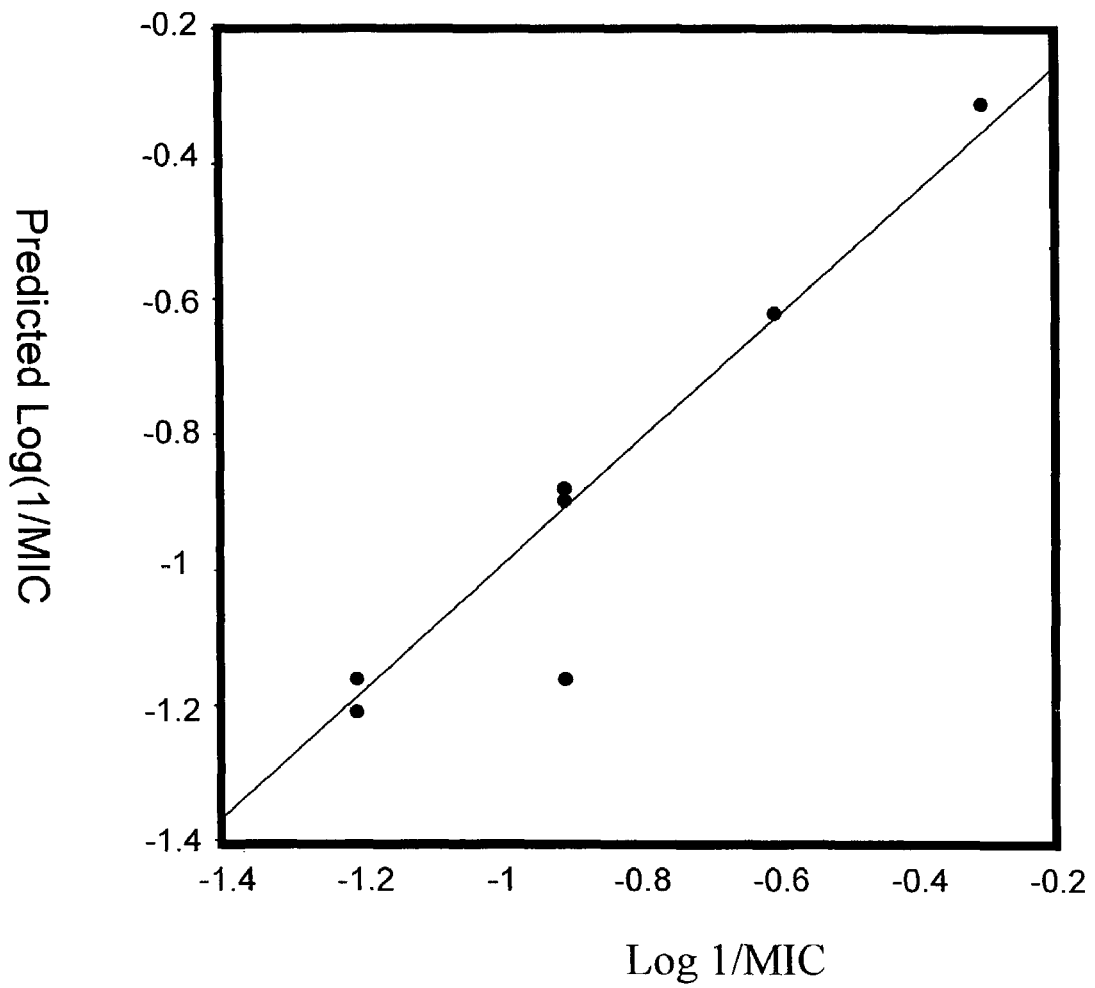
FIG. 12 is a graph showing the predicted log (1/MIC) versus experimental log (1/MIC) for a CoSCoSA model of cephalosporin minimum inhibitory concentrations.

The resulting model is shown in FIG. 12. The model showed a correlation $r^2$ 0.92, a F=36.2, a P<0.000005, a Leave-one-out $q_1^2$=0.88, a Leave-four-out $q_4^2$=0.79, and a Standard deviation 0.03.

Example 6

Structural Connectivity Spectral Data

Structural connectivity spectral data is spectral data attributable to components (e.g. atoms, groups of atoms, and bonds) of a molecule's structure combined with a relationship describing the relative positions within the structure of the molecule that these components occupy. Structural connectivity spectral data may be based on any type of spectral data that can be attributed to a component of molecular structure. For example, NMR data (including $^1$H, $^{13}$C, $^{15}$N, $^{17}$O, $^{19}$F, $^{35}$S, and $^{31}$P NMR data and combinations thereof), IR data, MS data, and UV-Vis, fluorescence and phosphorescence data where the molecules contain one or more chromophores. Furthermore, structural connectivity spectral data may be based on any combination of these types of spectral data. The relationship of the various components giving rise to particular signals may be any relationship that reflects the relative positions or shapes of components that are responsible for (or at least contribute to) the spectral signals exhibited by the molecule.

Structural connectivity spectra can, for example, be experimental $^{13}$C—$^{13}$C COSY and $^{13}$C—$^{13}$C distance spectra that reflect through-bond and through-space relationships between carbon atoms, respectively. In other embodiments, structural connectivity spectral data is predicted from one-dimensional experimental data and the molecule's structure. Predicted one-dimensional spectral data and molecular structure data may also be combined to predict structural connectivity spectral data. Another possibility is to use combinations of experimental spectral data and predicted spectral data along with structural data. In any case, the structural data can be experimental or predicted. As suggested above, structural connectivity spectral data may reflect through-bond relationships, through-space relationships, and combinations thereof. For example, $^{13}$C—$^{13}$C COSY data, $^{13}$C—$^{13}$C distance data, and combinations thereof may be used.

Where the spectral data is IR data, signals that correspond to stretching vibrations are particularly useful because such spectral signals may be identified to arise from specific bonds or groups of bonds between atoms, whereas bending vibrations may or may not be easily identified with particular bonds. For example, the first harmonic of the stretching vibration modes may be assigned to the center of the bond between the two atoms responsible for the signal in the same manner as a chemical shift is assigned to a particular atom in NMR data. Structural connectivity spectral data may then be predicted by combining the stretching frequencies identified with particular bonds with the distances between the centers of the bonds in the structure.

In another aspect, a relationship describing the relative positions of the components of structure responsible for (or that at least contribute to) particular signals is a geometric relationship such as a distance, angle, or vector that describes the relative positions of the components. The geometric relationship may be a distance between atoms derived from the molecule's known or calculated structure. Similarly, groups of atoms may be related to one another by the distance between the central atom of the group, or the center of mass of the group. Where the component is a bond, a distance between the center of each bond may be used to describe the relationship between bonds to which spectral data are attributable. If the relationship between components is a vector, the vector may be defined, for example, by a distance between particular components and an angle, such as an angle from the long or short axis of the molecule, between the components. Similarly an angle alone may be used to describe the relative positions of components in a structure.

In yet another aspect, the structural relationship between components may be described by the topological indices of the components, for example, chi and kappa indices (see, for example, Hall and Kier, "The Molecular Connectivity Chi Indices and Kappa Shape Indices in Structure-Property Modeling," in *Reviews of Computational Chemistry*, Volume 2, Boyd and Lipkowitz, eds, 1991). Another method to combine spectral data and structural data relating individual components of structure is to describe atoms by their topological state indices (see, for example, Hall and Kier, *Quant. Struct.-Act. Relat.*, 9: 115, 1990). Similarly, electrotopological state indices (E-state) and the electrotopological state for hydrogen atoms (HE-state) may be used (see, for example, Kellog et al., "The E-state Fields: Applications to 3D QSAR," *J. Comp. Aid. Molec. Des.*, 10: 513-520, 1996, and Kier and Hall, "Molecular Structure Description: The Electrotopological State," Academic Press, 1999). Bond-type electrotopological state indices may be useful, especially for IR data (see, for example, Molconn-Z 3.50 Manual, Chapter 2, Virginia Biotech, eduSoft, LC, P.O. Box 1811, Ashland, Va.).

Figure 13:
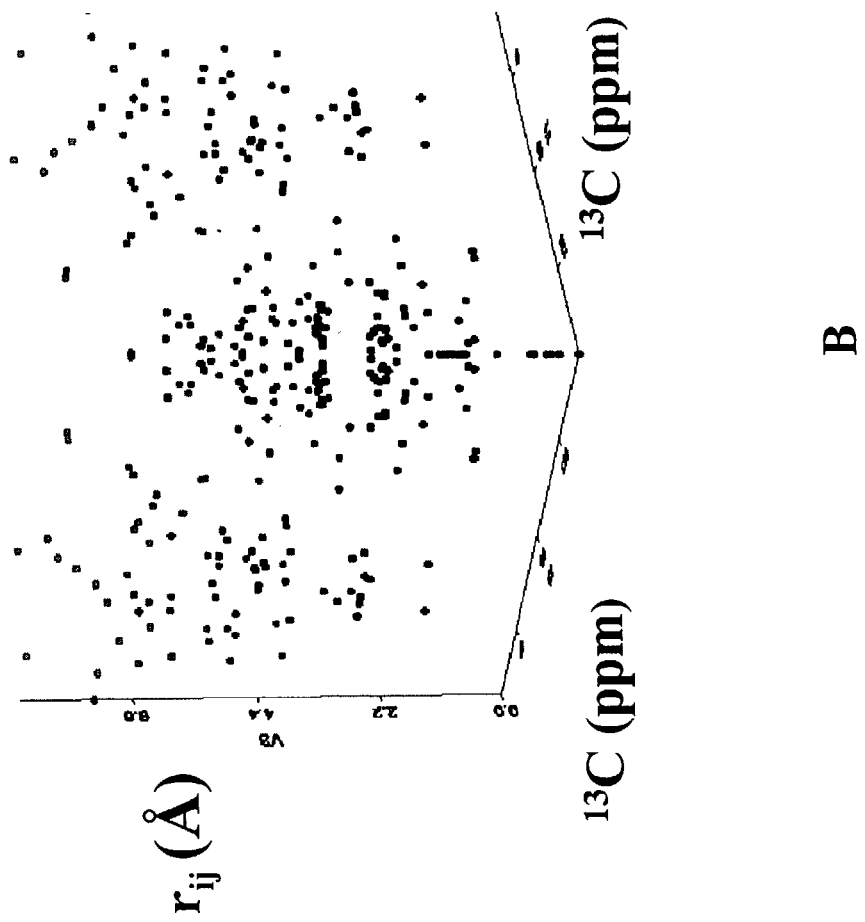
FIG. 13 is a representative three-dimensional $^{13}C$ NMR connection matrix for all possible carbon-to-carbon connections in a steroid molecule, where the x, y, and z axes respectively represent the chemical shift of a first carbon atom ($C_i$), the chemical shift of a second carbon atom ($C_j$), and the distance in Angstroms between the first and second carbon atoms ($r_{ij}$) as determined from the structure of the steroid molecule.
Figure 13:
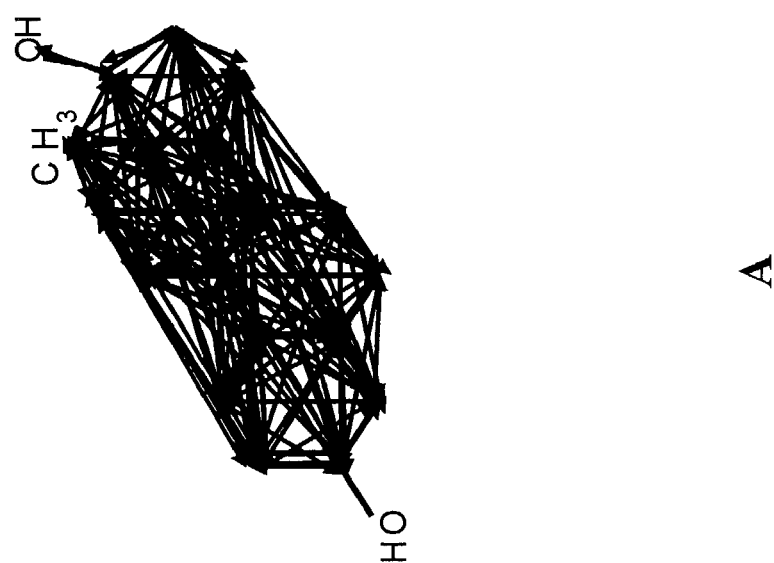
Figure 14:
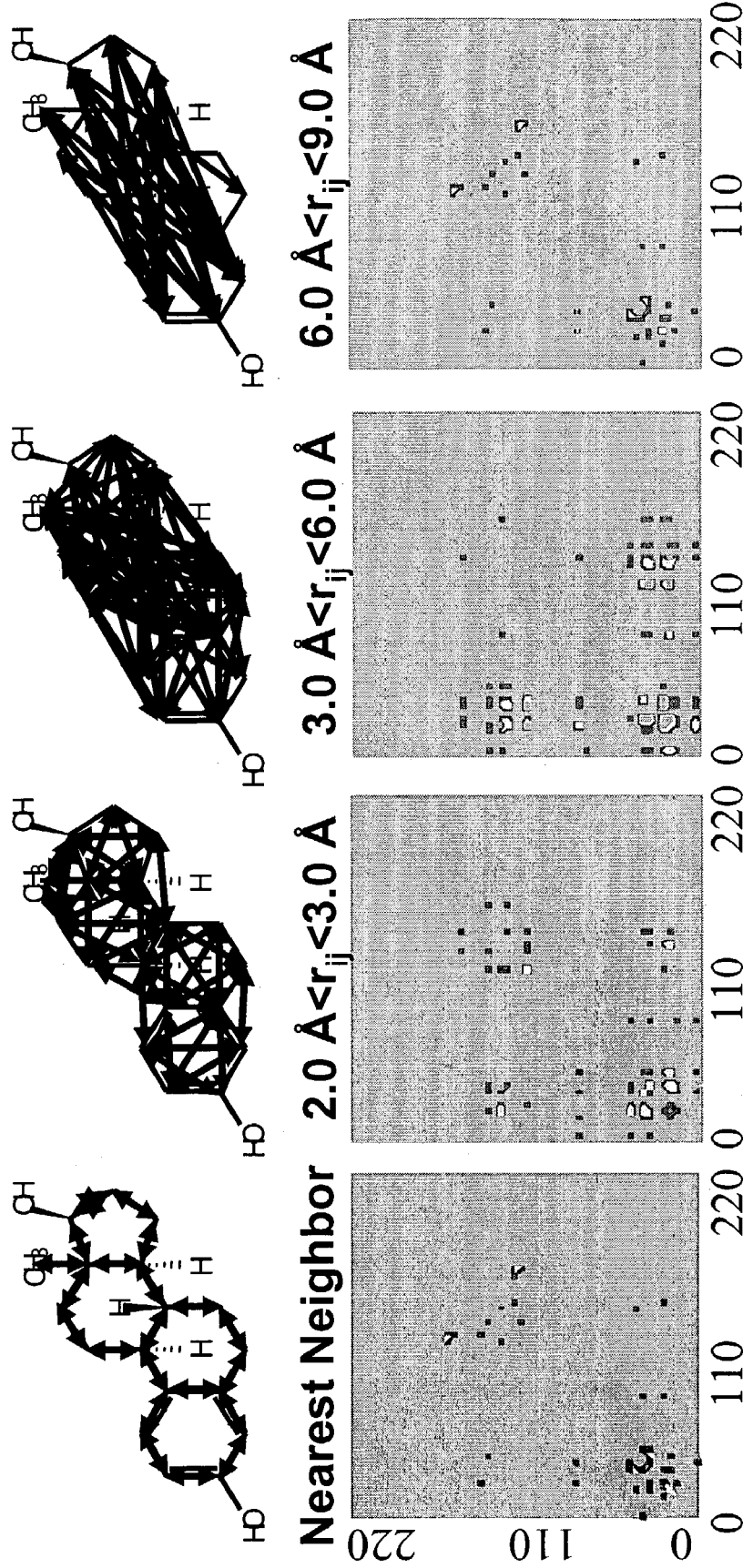
FIG. 14 is a diagram showing four representative sets of 2D $^{13}C$—$^{13}C$ structural connectivity spectral data derived from the 3D-connection matrix of FIG. 10.

An example of structural connectivity spectral data is shown in FIG. 13. Here, each atom of a steroid molecule is described by the NMR chemical shifts of the carbon atoms in the structure and the distances between each pair of carbon atoms (FIG. 13A). The result is a 3D spectral connectivity matrix (FIG. 13B). It is not necessary to use all possible data in the matrix because the matrix is symmetrical, and each connection effectively rotates the molecule in space. Furthermore, particular distance ranges that relate the spectral signals of the carbon atoms may be selected. This is illustrated in FIG. 14, where the 3D-spectral connection matrix has been reduced to 2D planes that include only data appearing in particular distance ranges. In FIG. 14 four representative sets of 2D $^{13}$C—$^{13}$C structural connectivity spectral data derived from the 3D-spectral connection matrix of FIG. 13 are shown. From left to right these 2D sets of data represent through-bond carbon-carbon connections between nearest neighbor atoms separated by less than 2.0 Å (i.e. a simulated $^{13}$C—$^{13}$C COSY spectrum), through-space connections between carbons separated by 2 to 3 Å (i.e. a simulated short range $^{13}C$—$^{13}C$ distance spectrum), through-space connections between carbons separated by 3 to 6 Å (i.e. a simulated medium range $^{13}C$—$^{13}C$ distance spectrum), and through-space connections between carbons separated by 6 to 9 Å (i.e. a simulated long range $^{13}C$—$^{13}C$ distance spectrum). These 2D distance-related planes may be used as sets of descriptors in an SDAR or QSDAR model. The distance planes may be further reduced to PCs correlated to the endpoint prior to combining them.

Figure 15:
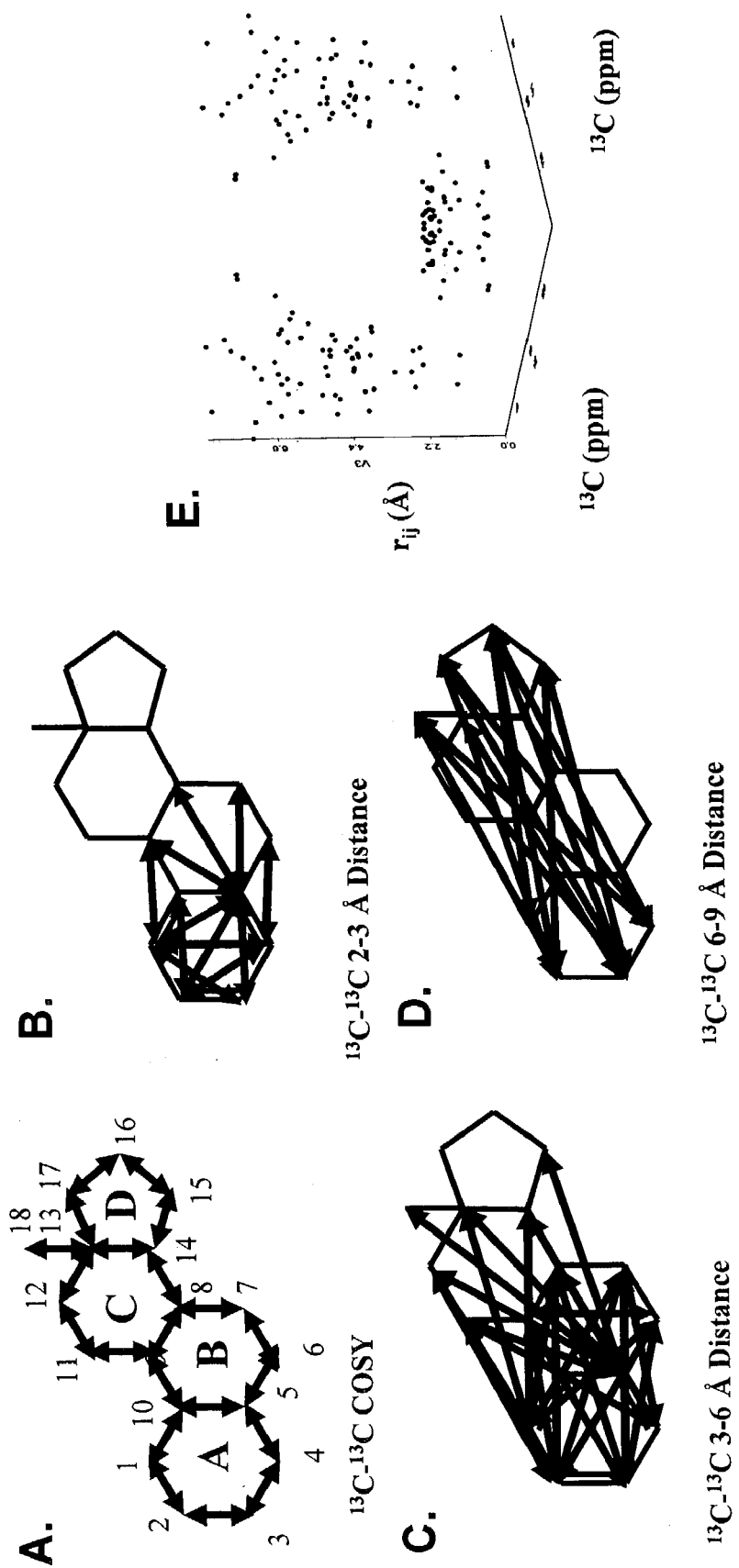
FIG. 15 is a diagram showing several embodiments of pharmacophore selection within a steroid structure and a representative 3D-spectral connectivity matrix.

An alternative method of producing a 3D-spectral connectivity matrix is to define distances with reference to a particular structural component, rather than with reference to the distances between each pair of components. For example, FIG. 15 shows a 3D-spectral connectivity matrix of $^{13}C$ NMR structural connectivity spectral data for a steroid skeleton (FIG. 15E). Here the matrix was constructed based on the distance between each carbon and the carbon at position 3 (the "anchor" component, in this case a "anchor" atom, which serves as the origin of the distance coordinate system) in the steroid, rather than based on the distance between each pair of carbon atoms. As shown in FIG. 14, the data shown in FIG. 15E could be reduced to 2-D planes corresponding to the distance ranges shown in FIGS. 15A-D. When the structural connectivity data is prepared in this manner, it may be used for pharmacophore analysis of a training set. For example, if one component of structure is known to be an important part of the pharmacophore of a molecule (e.g. carbon number 3 of the steroid skeleton), additional pharmacophore components within the molecule's structure may be identified by detecting the distance and/or angle (e.g. relative to the long axis of the molecule) of other correlated spectral signals from the known pharmacophore component. In theory any position in, on, or outside the structure of a molecule may be used as a "anchor" point from which distances used to create the matrix are measured. However, it may be advantageous to select a structural element that is shared by all the molecules in a training set of molecules as an "anchor." Multiple anchor points may also be used.

Example 7

"Anchored" CoSCoSA Model of PCDF, PCDD and PCB Binding to the Aryl Hydrocarbon Receptor The most comprehensive form of a 3D-connectivity matrix is built by plotting all possible carbon-to-carbon connections (through-bond and through-space) in relation to their assigned carbon NMR chemical shifts. In this type of matrix representation the x-axis shows the chemical shifts of carbon i, the y-axis shows the chemical shift of carbon j, and the z-axis the distance between carbons i and j ($r_{ij}$). Representation of a typical organic compound in this way dramatically increases the information content available to use as a basis for pattern recognition. Each carbon-to-carbon connection in the 3D matrix acts as a constraint on the structure of the molecule. However, the number of carbon-to-carbon constraints in a 3D-connectivity matrix increases as the square of the number of carbon atoms in the molecule. There are 3N-6 degrees of freedom in a molecule, where N is the number of atoms in the molecule. When the number of structural constraints exceeds the number of degrees of freedom, the information in a 3D-connectivity matrix is said to over-determine the structure of a molecule. For molecules the size of PCDFs, PCDDs, and PCBs, it is possible to reduce the detail in the 3D-connectivity matrix without losing access to the implicit structure-activity characteristics available from this way of describing them. One way to reduce the information is to reduce the third (distance) dimension of the 3D matrix into a set of distance categories or 2D spectral planes (See, for example, FIG. 14). The first 2D plane represents the nearest neighbor through-bond connectivity plane. The other 2D planes are constructed by compressing specific inter-atomic distances along the z-axis into a few distance categories, one containing all short distance atom-to-atom through-space connections, another for medium- and a third for long-distance atom-to-atom through-space connections. The particular distance intervals used in a model are not predetermined and can be among the parameters adjusted to optimize a model's performance. Once the ranges have been determined, the compressed connectivity spectra can be defined for any number of compounds. Pattern recognition techniques can then be used to develop the associations between patterns in 2D spectral data and the known biological activity of each compound. The known compounds comprise a training set for the pattern recognition. Once trained, the connectivity spectrum for any test compound can be used by the developed pattern relationships to predict that compound's biological activity.

This examples uses $^{13}C$ NMR spectra combined with structural information in the form of through-bond and selected through-space inter-atomic distances, defined relative to particular reference atoms called structural anchors. It demonstrates that such spectra/distance combinations can be used to produce reliable models of PCDF, PCDD, and PCB compounds binding to the AhR. It also demonstrates successful combination of spectra/distance matrices for all three compound types into a single model.

Table 13 column 3 contains previously reported log $EC_{50}$ binding activity data used for training these models. For each compound in Table 13, its $^{13}C$ NMR spectrum was simulated using the ACD Labs CNMR version 5.0 predictor software. For these compounds, there were no chemical shift peaks outside of 107.0 to 159.0 ppm range. Each compound's spectral pattern was defined using, as a surrogate for peak volume, the number of atoms having chemical shifts within segments of this range. The segments are referred to as bins and the number of atoms as the population of a bin. These binned spectral peaks were combined with the associated inter-atomic distances provided the spectral component of the CoSCoSA models.

TABLE 13

| # | Compound | Experimental Log $EC_{50}$ | 52 Compound Predicted Log $EC_{50}$ |
|---|---|---|---|
| 1 | 1-Cl-dibenzofuran | −5.53 | −6.53 |
| 2 | 2,8-diCl-dibenzofuran | −6.05 | −5.79 |
| 3 | 2,3,7-triCl-dibenzofuran | −8.10 | −7.86 |
| 4 | 2,3,8-triCl-dibenzofuran | −7.00 | −6.53 |
| 5 | 2,6,7-triCl-dibenzofuran | −7.35 | −6.53 |
| 6 | 1,2,3,6-tetraCl-dibenzofuran | −7.46 | −7.97 |
| 7 | 1,2,3,7-tetraCl-dibenzofuran | −7.96 | −7.38 |
| 8 | 1,2,4,8-tetraCl-dibenzofuran | −6.00 | −6.53 |
| 9 | 2,3,4,6-tetraCl-dibenzofuran | −7.46 | −7.38 |
| 10 | 2,3,6,8-tetraCldibenzofuran | −7.66 | −7.38 |
| 11 | 2,3,7,8-tetraCl-dibenzofuran | −8.60 | −8.55 |
| 12 | 1,2,3,7,8-pentaCl-dibenzofuran | −8.12 | −8.23 |
| 13 | 1,2,3,7,9-pentaCl-dibenzofuran | −7.40 | −7.66 |
| 14 | 1,2,4,7,9-pentaCl-dibenzofuran | −5.70 | −5.22 |
| 15 | 1,3,4,7,8-pentaCl-dibenzofuran | −7.70 | −7.01 |
| 16 | 2,3,4,7,8-pentaCl-dibenzofuran | −8.82 | −8.34 |
| 17 | 1,2,4,6,7,8-hexaCl-dibenzofuran | −6.08 | −6.56 |
| 18 | 2,3,4,6,7,8-hexaCl-dibenzofuran | −8.33 | −8.45 |
| 19 | 1,2,3,4,7,8-hexaCl-dibenzofuran | −7.64 | −7.49 |
| 20 | 1,2,3,6,7,8-hexaCl-dibenzofuran | −7.57 | −7.01 |
| 21 | 2,3,4,7,9-pentaCl-dibenzofuran | −7.70 | −7.38 |

TABLE 13-continued

| # | Compound | Experimental Log EC$_{50}$ | 52 Compound Predicted Log EC$_{50}$ |
|---|---|---|---|
| 22 | 2,3,4-triCl-dibenzofuran | −5.72 | −5.44 |
| 23 | 2,3-diCl-dibenzofuran | −6.33 | −6.62 |
| 24 | 2,6-diCl-dibenzofuran | −4.61 | −4.27 |
| 25 | 2-Cl-dibenzofuran | −4.55 | −5.12 |
| 26 | 4-Cl-dibenzofuran | −4.50 | −4.27 |
| 27 | 1-Cl-dibenzodioxin | −5.00 | −4.85 |
| 28 | 2,8-diCl-dibenzodioxin | −6.49 | −6.53 |
| 29 | 2,3,7-triCl-dibenzodioxin | −8.15 | −7.90 |
| 30 | 1,3,7,8-tetraCl-dibenzodioxin | −7.10 | −7.21 |
| 31 | 2,3,7,8-tetraCl-dibenzodioxin | −9.00 | −9.28 |
| 32 | 1,2,3,4,7-pentaCl-dibenzodioxin | −6.19 | −6.65 |
| 33 | 1,2,3,4,7,8-hexaCl-dibenzodioxin | −7.55 | −7.21 |
| 34 | 1,2,3,7,8-pentaCl-dibenzodioxin | −8.10 | −7.21 |
| 35 | octaCl-dibenzodioxin | −6.00 | −6.53 |
| 36 | 1,2,3,4-tetraCldibenzodioxin | −6.88 | −6.53 |
| 37 | 1,2,4,7,8-pentaCl-dibenzodioxin | −6.96 | −7.21 |
| 38 | 1,2,4-triCl-dibenzodioxin | −5.88 | −6.53 |
| 39 | 2,3,6,7-tetraCl-dibenzodioxin | −7.79 | −7.90 |
| 40 | 2,3,6-triCl-dibenzodioxin | −7.66 | −7.21 |
| 41 | 2,2',4,4',5,5'-hexaCl-biphenyl | −5.10 | −4.96 |
| 42 | 2,2',4,4'-teraCl-biphenyl | −4.89 | −4.96 |
| 43 | 2,3,3',4,4',5-hexaCl-biphenyl | −6.30 | −6.53 |
| 44 | 2,3,3',4,4'-pentaCl-biphenyl | −6.15 | −6.53 |
| 45 | 2,3',4,4',5,5'-hexaCl-biphenyl | −5.80 | −6.53 |
| 46 | 2,3',4,4',5-pentaCl-biphenyl | −6.04 | −6.13 |
| 47 | 2,3,4,4',5-pentaCl-biphenyl | −6.38 | −6.13 |
| 48 | 2',3'4,4',5-pentaCl-biphenyl | −5.85 | −6.53 |
| 49 | 2,3,4,4'-tetraCl-biphenyl | −5.55 | −6.53 |
| 50 | 2,3,4,5-tetraCl-biphenyl | −4.85 | −4.96 |
| 51 | 3,3',4,4',5-pentaCl-biphenyl | −7.92 | −7.14 |
| 52 | 3,3',4,4'-tetraCl-biphenyl | −7.37 | −7.76 |

In column two are the compounds used in CoSCoSA models of binding to AhR, column three is the structure's experimental Log EC$_{50}$ and column four is the predicted Log EC$_{50}$ from the 52 compound CoSCoSA model of the present example.

Figure 16:
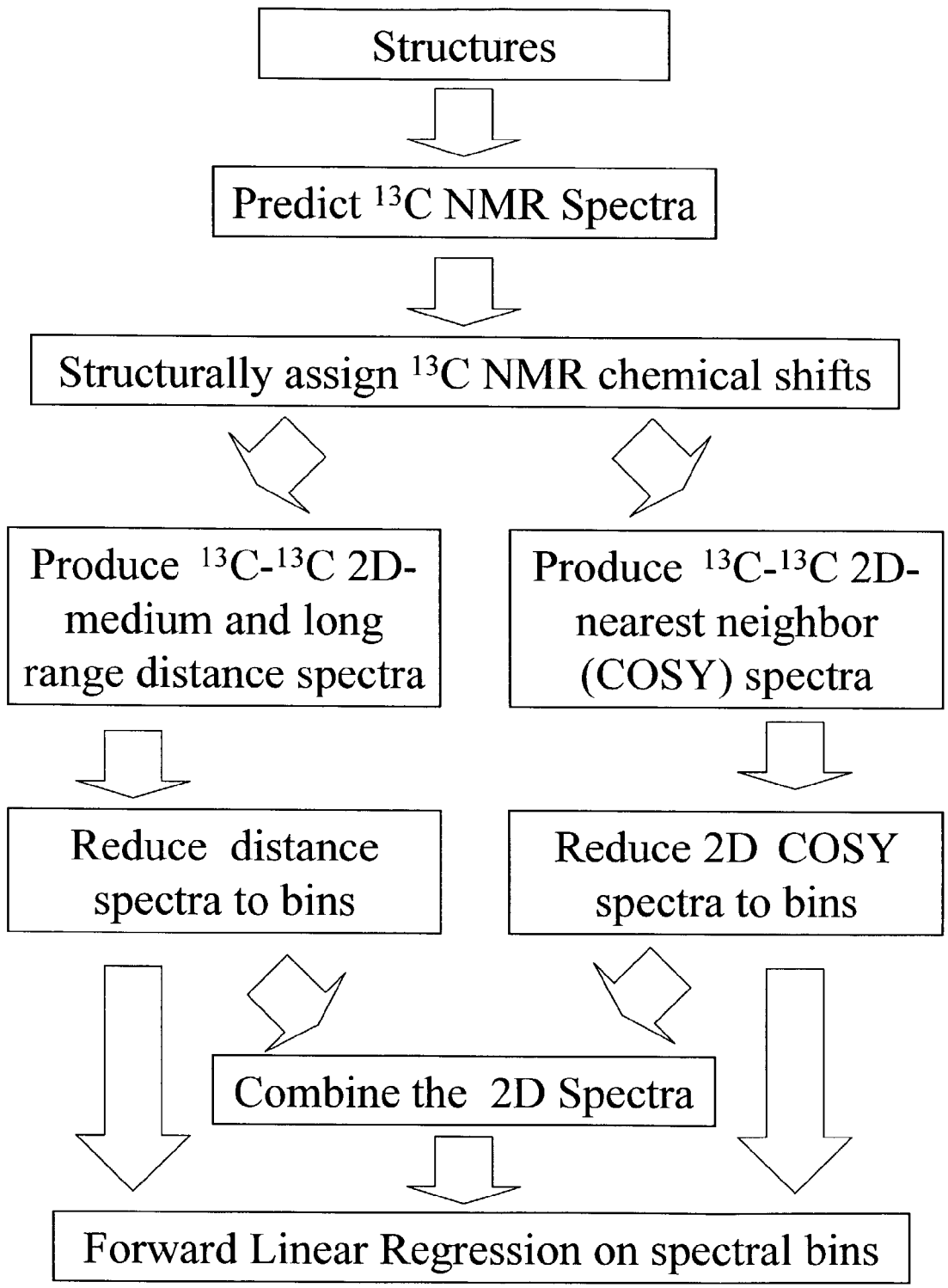
FIG. 16 is a flow chart for a particular embodiment of CoSCoSA modeling.

The competitive in vitro binding affinities EC$_{50}$ of PCDF, PCDD, and PCB compounds have been determined previously using [3H]-2,3,7,8-tetrachlorodioxin as the radioligand and rodent hepatic cytosol as a source of the AhR. These binding affinities represented the biological activity component of the CoSCoSA models. FIG. 16 shows the flow chart for the CoSCoSA modeling procedure of this example. The ID $^{13}$C NMR spectra were predicted for the compounds in Table 13. The chemical shifts and atom assignment were used from the ID prediction software and all possible carbon interatomic distances were obtained from ACD 3D Viewer software provided with the ACD $^{13}$C NMR prediction software. Since the structures of PCDDs and PCDFs are planar and rigid, the 2D mol file coordinates were usable in the ACD 3D Viewer to determine intramolecular distances between carbon atoms. Similarly, the 2D mol file coordinates of PCB structures were used in the 3D Viewer because the PCB compounds used in this study were considered to have a planar structure. Greater care would be required to determine intramolecular distances for very flexible compounds. 2D planes were built from the combined chemical shift and structural information. One 2D plane represented through-bond COSY spectra. Another represented distances from "anchoring atoms" to atoms in the middle of the compound. The third, long distance plane served the range from the anchor locations to atoms on the opposite end of the compound. All 2D spectral planes were reduced to a 2.0 ppm resolution in both chemical shift dimensions. These choices resulted in 625 bins. A 2.0×2.0 ppm bin size was used in order to multiply populate as many as possible of the 2D bins. That is, for the training set of compounds it was important that each populated bin be represented by more than one molecule, so that binding affinity inferences from the resulting model would represent generalizations based on multiple examples rather than rote "memorization" of single discrete features. To facilitate generalization, bin dimensions can be increased as long as the inclusion of signals in a single bin does not render signals from different parts of the molecule that should be distinguished from each other as equivalent. Confusion might occur if signals that arose from atomic environments that contribute differently to the biological activity being modeled were combined. On the other hand, multiply populated bins are advantageous for statistical analysis of the models, particularly model validation. They also reduce the effects of uncertainties from the use of simulated rather than experimental spectra. The first 2D bin included chemical shifts from 157.00 to 158.99 in both the x- and y-dimensions. A 2.0 ppm spectral bin width was chosen in particular because it was used successfully in prior AhR CoSA and CoSCoSA models. The raw 2D $^{13}$C—$^{13}$C NMR spectra were represented as two-dimensional bins populated by the number of carbon atoms having a chemical shift within each bin, with the number normalized to a three digit integer. For these rigid compounds, each molecule was assumed to have only a single conformation. Typically, a single carbon-to-carbon connectivity on any 2D plane was assigned an area of 100, two carbon-to-carbon connections populating a bin had an area of 200, and so forth.

Figure 17:
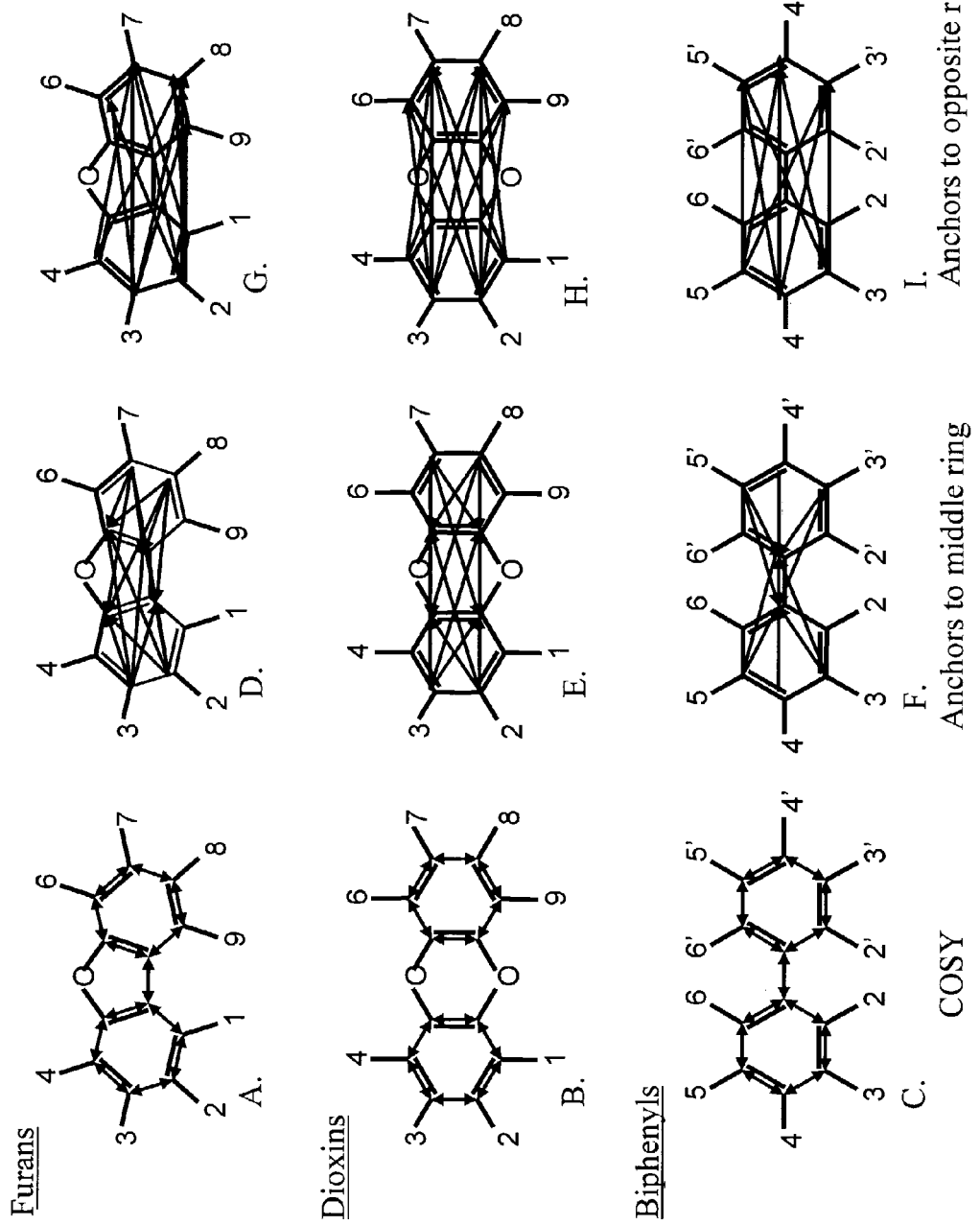
FIG. 17 is diagram showing a set of distance relationships used for 2D $^{13}C$—$^{13}C$ COSY spectra for PCDFs (A), PCDDs (B) and PCBs (C); middle range 2D $^{13}C$—$^{13}C$ distance spectra for PCDFs (D), PCDDs (E) and PCBs (F); and long range 2D $^{13}C$—$^{13}C$ distance spectra for PCDFs (G) PCDDs (H) and PCBs (I).

CoSCoSA models were produced by using the assigned $^{13}$C NMR chemical shifts at the 12 carbon positions in the PCDF, PCDD, and PCB molecules, as shown in FIG. 17. The arrows in FIGS. 17A, 17B, and 17C show the through-bond COSY carbon-to-carbon connections of the PCDF, PCDD, and PCB molecules, respectively. These through-bond carbon-to-carbon connections were used to simulate 2D $^{13}$C—$^{13}$C COSY spectra of the PCDF, PCDD, and PCB compounds. As mentioned earlier, instead of using all interatomic distances that might be included in the 2D-medium- or long-range planes of the 3D-connectivity matrix, a meaningful subset was defined by breaking each PCDD, PCDF, or PCB molecule into three pieces. The atoms in each compound were segregated into those in an "anchoring position," those a middle distance from the anchors, and those at a long-range distance—opposite the "anchor position."

2,3,7,8-tetrachlorodibenzodioxin is a strong binder in AhR and the presence of these four chlorine atoms constitutes an important factor in determining the compound's toxicity. The distance between positions 2 and 8 or 3 and 7 is 7.0 Å. 2,3,7,8-tetrachlorofuran is also a strong binder to the AhR and the distance between its chlorinated positions 2 and 8 or 3 and 7 is 6.76 Å. Generally, for PCDDs and PCDFs, any pattern that includes chlorination at positions 2, 3, 7 and 8 is known to be associated with the compound's strong binding to the AhR. That is the reason the 2, 3, 7, and 8 positions were used as structural "anchors" for the distance-related CoSCoSA models.

The arrows in FIGS. 17D and 17E show the medium range through-space connections from the 2 and 3 or 7 and 8 anchoring positions to the middle ring carbons in PCDF and PCDD molecules, respectively. PCBs, of course, do not contain a middle ring. For PCB molecules in FIG. 17F, anchoring positions were defined as the 3, 4, and 5 positions and the 3', 4', and 5' positions. Atoms in the middle-distance range from these anchors consisted of just the two ring-connecting carbons. The arrows in FIGS. 17G and 17H show the long-range through-space connections from the 2 and 3 or 7 and 8 anchoring positions to the opposite ring carbons in PCDF and PCDD molecules, respectively. Likewise, for PCB molecules in FIG. 17I, the long-range connections are from the 3, 4, and 5 positions and the 3', 4', and 5' positions to the carbons on the opposite ring. Since this long-range connectivity interaction overlapped the two anchoring points for each molecule, we choose only one anchor ring as the "origin" from which all long-range through-space connections originated.

CoSCoSA models were built (1) using the nearest neighbor 2D through-bond spectral plane only, (2) using the anchoring structural through-space distance 2D planes, and (3) using a combination of through-bond and through-space information. Since there were two anchors per molecule, we could theoretically have separated the medium-range through-space distance connections from the outer ring anchors to the middle of the compound (FIGS. 17D, E, and F) into two separate 2D planes. However, this was not done because of symmetry and because the resulting training set would have been too small for meaningful statistics. In contrast, for the short distance 2D COSY, the connectivity arrows point both to and from the nearest neighbor atom. Because of this duality only half of the 2D COSY spectra is needed to define all of the spectra/short distance relationships. Since the medium-range and long-range through-space distances that originate from the anchoring "origins" do not have the connectivity arrow dual directionality, the whole 2D spectral plane is used in model development. CoSASA models for PCDD and PCDF compounds were built from 12 assigned carbon chemical shifts All statistical analysis was performed by Statistica version 6.0 software. For each CoSCoSA model, forward multiple linear regression (MLR) was used on selected bins. The models did not use any bins that had less than 2 "hits". Each CoSCoSA model was built with the goal of comparing performance not only to previous CoSA models but also to that of the other CoSCoSA models shown in Example 2 that used the same set of congeners for training. Therefore, the number of bins selected was not optimized for each particular CoSCoSA model, even though for some sets of molecules, inclusion of more bins could have increased the F-test value whereas in other types of models the number used exceeded F-test maximum. For the 26 PCDFs, the following standards were set for the forward MLR. The "F to Enter", a user-defined $F_{critical}$ threshold, was set to 1.0 for the selection of 6 bins. This was done from COSY data alone, for through-space distance from the anchors alone and finally for the through-space distance from the anchors data combined with COSY data. This produced three corresponding CoSCoSA models. Similarly, for the 14 PCDDs or 12 PCBs the forward MLR was conducted with "F to enter" set to 1.0 and specifying the selection of 3 bins, CoSCoSA models were produced based on COSY alone, through-space distance alone, and combined spectral data. Finally, a CoSCoSA model of all 52 compounds was produced using forward MLR with "F to enter" set to 1.0 for the selection of 10 bins from the combined COSY and through-space distance generated 2D spectral planes.

Assessments of these ten CoSCoSA models were achieved using leave-one-out (LOO) or leave-multiple-out cross-validation procedures in which one or more compounds were systematically excluded from the training set and each developed model (missing any contribution from the excluded compound(s)) was used to predict inhibitor binding activities. The cross-validated $r^2$ (termed $q^2$) that resulted from the cross-validation experiments was derived from $q^2=1-$ PRESS/SSD. PRESS indicates the sum of the differences between the actual and predicted activity data for each molecule during LOO cross-validation, and SSD is the sum of the squared deviations between the measured and mean activities of each molecule in the training set. During the LOO cross-validation, each compound was removed from the training set and the B-coefficients in the MLR equation were recalculated. This new MLR equation was used to recalculate the log(RBA) of the compound left out. To more rigorously test the validity of the CoSCoSA models, leave-two-out cross validations were performed on the models developed for the 14 PCDDs and the 12 PCBs, and leave-four-out cross-validations were executed on the models for the 26 PCDFs and the multiple compound type model that contained 52 compounds.

Tables 14 through 17 report values of n, $r^2$, $q^2$, $q_n^2$, SE (standard error), and F and also identify the 2D bins used for the PCDF, PCDD, PCB, and all 52 compound CoSCoSA models, respectively. For comparison, all of the CoSCoSA models for PCDF compounds were based on 6 MLR-selected 2D bins. All CoSCoSA models for PCDD and PCB compounds were based on 3 objectively selected bins. The CoSCoSA model for all 52 compounds was based on 10 selected bins.

Figure 18:
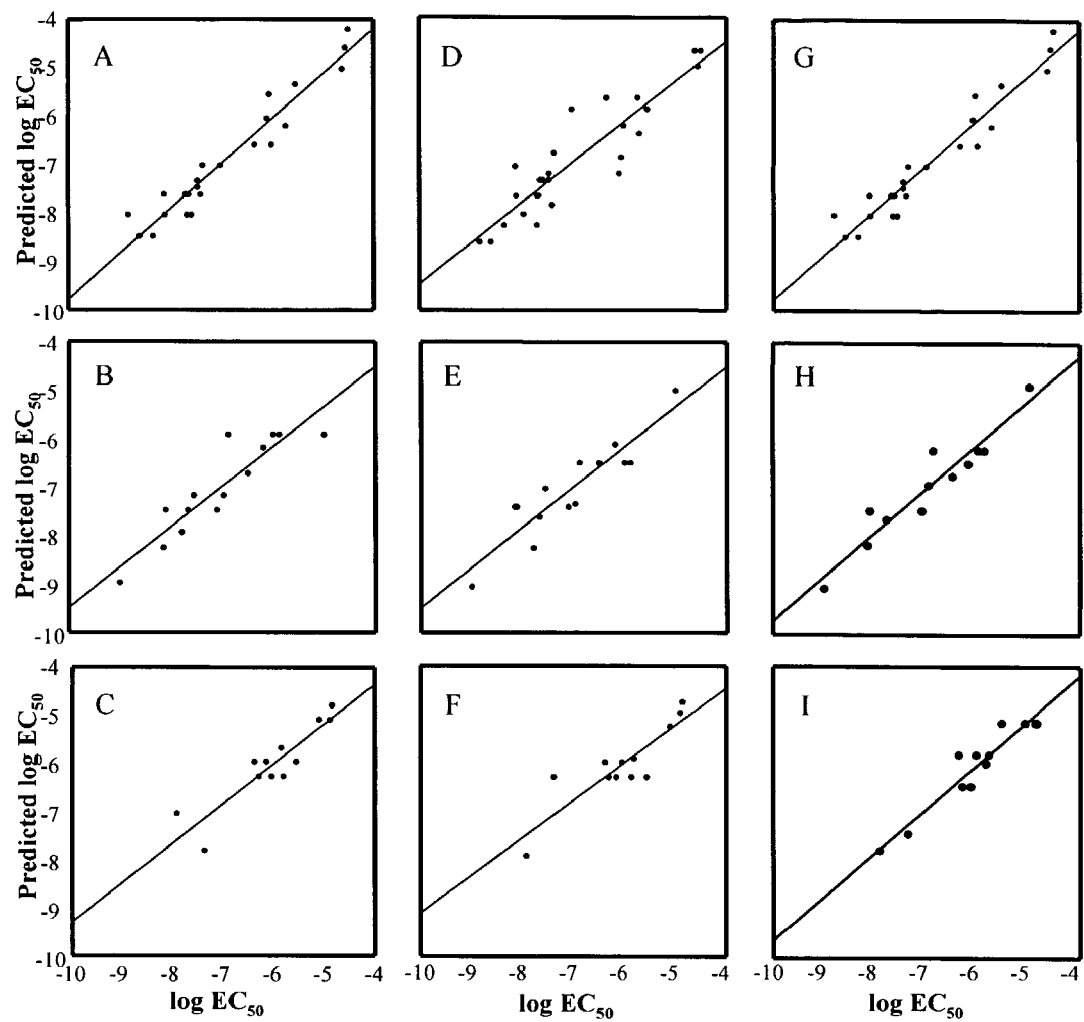
FIG. 18 is a set of graphs showing the CoSCoSA predicted binding versus experimental binding based on COSY spectra for PCDFs (A), PCDDs (B) and PCBs (C); the predicted binding versus experimental binding based on medium-range and long-range distance spectra for PCDFs (D), PCDDs (E) and PCBs (F); and the predicted binding versus experimental binding based on the combined COSY and distance spectra for PCDFs (G), PCDDs (H) and PCBs (I).

In Table 14 for PCDF compounds, two of three CoSCoSA models had a higher $r^2$ and $q^2$ than the corresponding ID CoSA model using a 2 ppm bin size. Additionally, all three CoSCoSA models for the PCDF compounds had higher $r^2$ and $q^2$ than the 2D CoSASA model that associated spectral chemical shift changes at structurally assigned locations with binding to the AhR. The COSY model for PCDF, shown by FIG. 18A, was based on COSY bins 119-113 (All 2 ppm bins are written using the format a-b, where a and b are the ppm values corresponding to the two "connected" atoms), 125-113, 153-113, 127-119, 155-119, and 127-125. The COSY bin 153-113 identified 10 of the 11 compounds that had activities weaker than −7.0 with only one outlier. The COSY bin 155-119 identified 12 of 15 compounds that had binding activities stronger than −7.0 with 3 outliers. Both the COSY bin at 153-113 and bin 155-119 identified energies of carbon number 5 or 12 from the middle ring connected to the furyl oxygen. These bins are consistent with the fact that bins associated with the furyl oxygen in PCDF compounds also showed a high correlation to binding in previous 1 ppm and 2 ppm resolution CoSA models. Both the COSY bins at 127-125 and 127-119 identified energies from the carbons numbered 2, 3, 7, and 8. FIG. 18D shows performance of the PCDF CoSCoSA model based on medium-range and long-range distance bins. FIG. 18G shows the PCDF CoSCoSA model based on COSY, medium-range, and long-range distance bins. The CoSCoSA models for PCDF compounds started with 625 two-dimensional bins in all three 2D planes. When all the bins with only zero population values were removed from the 2D COSY spectral plane, the PCDF CoSCoSA models had 63 remaining bins for that part of the data. Similarly, when all the bins with only zero values were removed from the 2D medium and long range distance planes, the PCDF CoSCoSA models actually had available a combined 133 bins.

TABLE 14

26 PCDF compound model performance parameters n (parameters used), $r^2$, $q^2$, $q_4^2$, SE, F and MLR Equation (C stands for COSY, M stands for medium-range and L stands for long-range spectra).

| Model | n | $r^2$ | $q^2$ | $q_4^2$ | SE | F | MLR Equation |
|---|---|---|---|---|---|---|---|
| 1D CoSA | 5 Bins | 0.82 | 0.72 | | 0.60 | 18.6 | |
| 2D CoSASA | 6 Atoms | 0.74 | 0.70 | | 0.75 | 9.1 | |
| COSY | 6 Bins | 0.92 | 0.84 | 0.84 | 0.40 | 38.7 | $-0.03443 * (C_{119-113}) +$ $0.01245 * (C_{125-113}) +$ $0.01031 * (C_{153-113}) +$ $0.00782 * (C_{127-119}) -$ $0.00426 * (C_{155-119}) +$ $0.02003 * (C_{127-125})$ |
| Mid + Long | 6 Bins | 0.83 | 0.63 | 0.65 | 0.61 | 15.1 | $0.00616 * (M_{127-115}) +$ $0.00576 * (M_{125-117}) -$ $0.00184 * (L_{119-125}) +$ $0.00949 * (L_{125-125}) +$ $0.00967 * (L_{113-127}) +$ $0.01783 * (L_{121-127})$ |
| COSY + Mid + Long | 6 Bins | 0.92 | 0.84 | 0.84 | 0.40 | 38.7 | $-0.03443 * (C_{119-113}) +$ $0.01245 * (C_{125-113}) +$ $0.01031 * (C_{153-113}) +$ $0.00782 * (C_{127-119}) -$ $0.00426 * (C_{155-119}) +$ $0.02003 * (C_{127-125})$ |

A previous 2 ppm resolution CoSA model based on five bins for 26 PCDF compounds had an $r^2$ of 0.82 and $q^2$ of 0.72. A structural parameter model that used Lmax, HOMOs, E(HOMO-LUMO), Log P, and GIW (the geometric analogue of Weiner topological indices) produced by Mekenyan et al. (Mekemyan et al, *Environ. Health Perspect.* 104: 1302, 1996) was used to produce a 5 component model for 25 PCDF compounds (all 26 PCDF compounds except for 237-trichlorodibenzofuran) with an $r^2$ of 0.85 and $q^2$ of 0.71. The best model for 39 dibenzofurans proposed by Turner et al., one that used three infrared EVA molecular descriptors had an $r^2$ of 0.96 and a $q^2$ of 0.73. Another six-component QSAR CoMFA model had an $r^2$ of 0.85 and a $q^2$ of 0.72 (Turner et al., *Comput. Aid. Mol. Des.*, 11:409, 1997). These performance results were compared to those of the CoSCoSA PCDF models.

As shown in Table 15, for the PCDD compounds, all three CoSCoSA models had $r^2$ and $q^2$ values similar to the corresponding 1D CoSA model based on three 2 ppm bins. The CoSCoSA models were based on the selection of 3 2D bins and the previous 1D CoSA model was based on 3 1D bins. All three CoSCoSA models for PCDD compounds had a much higher $r^2$ and $q^2$ values than the 2D CoSASA model. FIG. 18B shows the COSY model for PCDD compounds that was based on COSY bins 127-123, 141-123, and 143-123. The COSY bin 143-123 correctly identified all 8 compounds with binding activities stronger than −6.96 with only one outlier. The bins at 141 and 143 ppm always identified the energies of one of the four carbon atoms in the middle ring next to the two oxygen atoms. These bins are consistent with the fact that bins in our previous 1 ppm and 2 ppm resolution CoSA models associated with the carbon atoms next to the two oxygens in PCDD compounds had a high correlation to binding. FIG. 18E shows the PCDD CoSCoSA model based on medium-range and long-range distance bins. FIG. 18H shows the PCDD CoSCoSA model based on COSY, medium-range, and long-range distance bins. The PCDD CoSCoSA models had 48 bins for the $^{13}C$—$^{13}C$ COSY data and a combined 54 bins for the medium and long $^{13}C$—$^{13}C$ distance connectivity data when all the bins with only zero values were removed from the 2D spectral planes. For comparison, a previous 1D CoSA model based on three chemical shift bins for the 14 PCDD compounds had an $r^2$ of 0.83 and a $q^2$ of 0.74. Five structural parameters were used by Mekenyan et al to produce a five component model for 14 PCDD compounds that had an $r^2$ of 0.95 and $q^2$ of 0.82. The model for 25 dibenzodioxins proposed by Turner et al. that used two infrared EVA molecular descriptors had an $r^2$ of 0.88 and a $q^2$ of 0.65, and a two component QSAR CoMFA model had an $r^2$ of 0.88 and a $q^2$ of 0.73.

TABLE 15

14 PCDD compound model performance parameters bin n (parameters used), $r^2$, $q^2$, $q_2^2$, SE, F and MLR Equation (C stands for COSY, M stands for medium-range and L stands for long-range spectra).

| Model | n | $r^2$ | $q^2$ | $q_2^2$ | SE | F | MLR Equation |
|---|---|---|---|---|---|---|---|
| 1D CoSA | 3 Bins | 0.83 | 0.74 | | 0.50 | 16.5 | |
| 2D CoSASA | 5 Atoms | 0.81 | 0.53 | | 0.60 | 6.7 | |
| COSY | 3 Bins | 0.83 | 0.75 | 0.74 | 0.51 | 15.9 | $0.00375 * (C_{127-123}) -$ $0.01145 * (C_{141-123}) -$ $0.00794 * (C_{143-123}) -$ |
| Mid + Long | 3 Bins | 0.83 | 0.75 | 0.71 | 0.51 | 16.3 | $0.00516 * (M_{123-141}) -$ $0.00095 * (M_{125-141}) -$ $0.0017 * (M_{127-141})$ |
| COSY + Mid + Long | 3 Bins | 0.90 | 0.79 | 0.79 | 0.41 | 16.2 | $-0.0071 * (C_{141-123}) -$ $0.00527 * (C_{143-123}) +$ $0.00441 * (M_{123-141})$ |

As shown in Table 16 for the PCB compounds, all three CoSCoSA models had higher $r^2$ and much higher $q^2$ values than the corresponding 1D CoSA model using 2 ppm bins. The CoSA and CoSCoSA models were based on the selection of 3 bins. FIG. 18C shows the PCB COSY model based on COSY bins 137-125, 127-127, and 133-131. The COSY bin at 137-125 correctly identified-both compounds with a binding activity stronger than −7.0. The COSY bin 137-125 is identified with a bridge carbon having energy associated with 137 ppm and a connecting carbon on one of the rings at 125 ppm. FIG. 18F shows the PCB CoSCoSA model based on medium-range and long-range distance bins. FIG. 18I shows the PCB CoSCoSA model based on the COSY, medium-range and long-range distance bins. After all the bins with only zero values were removed from the 2D spectral planes, the PCB CoSCoSA models had 28 remaining populated bins available for the $^{13}C$—$^{13}C$ COSY data and a combined 39 populated bins for the medium and long $^{13}C$—$^{13}C$ distance connectivity data. For comparison, a previous CoSA model based on three bins for the 12 PCB compounds had an $r^2$ of 0.66 and a $q^2$ of 0.30. The model for 33 biphenyls proposed by Turner et al. that used one infrared EVA molecular descriptor had an $r^2$ of 0.72 and a $q^2$ of 0.16 and a previous three component QSAR CoMFA model had an $r^2$ of 0.87 and a $q^2$ of 0.49. Mekenyan et al. used structural parameters to produce a model for 12 PCB compounds that had an $r^2$ of 0.95 and $q^2$ of 0.79.

Figure 19:
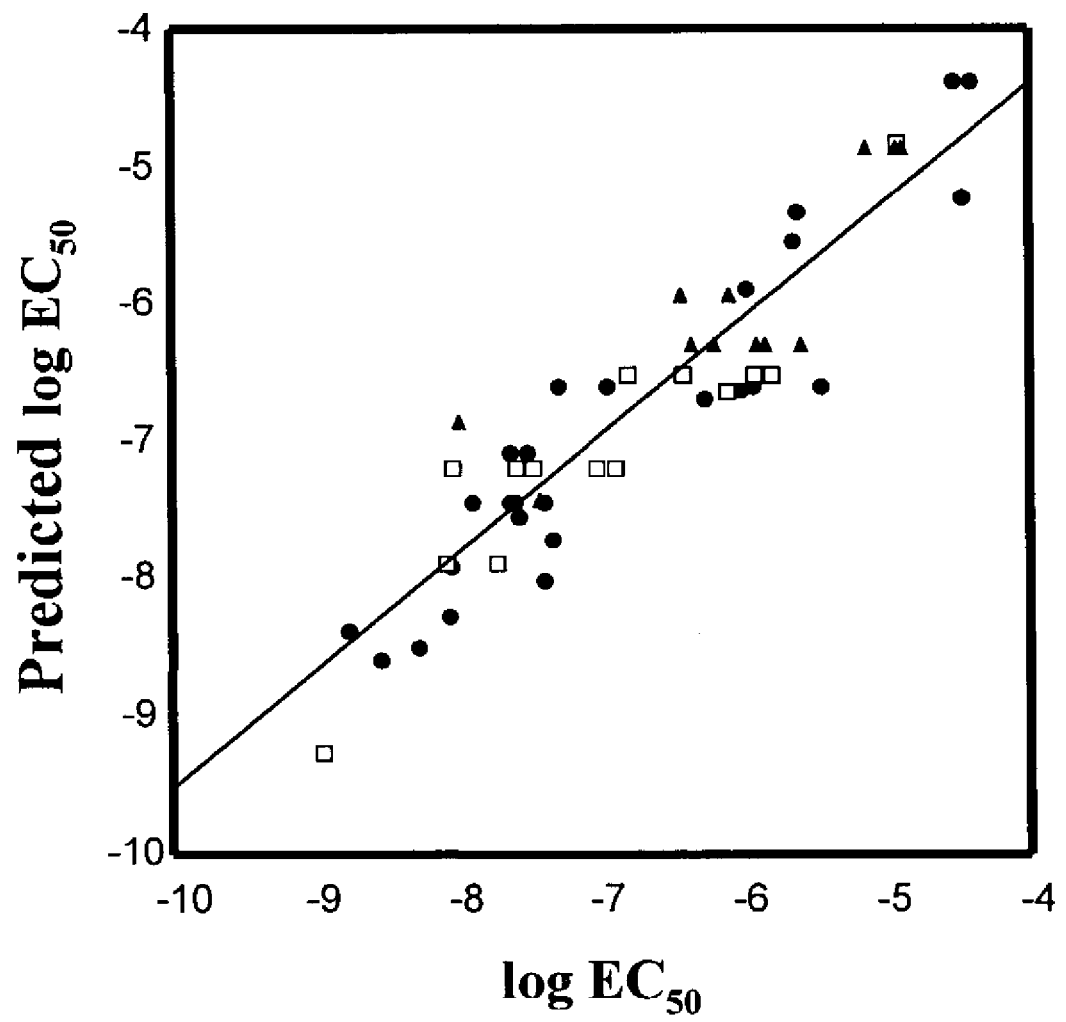
FIG. 19 is a graph showing the predicted binding versus experimental binding for all 52 PCDF, PCDD and PCB compounds from a CoSCoSA model based on the combined COSY plus medium- and long-range spectra. The PCDF compounds are shown with filled circles (●), PCDD compounds are shown with open squares (□), and PCB compounds are shown with filled triangles (▲).

In Table 17, results for the single CoSCoSA model of all 52 PCDF, PCDD, and PCBs are shown. Here, the combined COSY and through space CoSCoSA model had significantly higher $q^2$ values than the corresponding 1D CoSA model using 2 ppm bins. Additionally the CoSCoSA model was based only on 10 2D bins, whereas the CoSA models were based on 15 or 12 1D bins, respectively. FIG. 19 is a plot of the predicted versus experimental binding for all 52 compounds using the combined COSY, medium and long-range distance spectra. The PCDF compounds are shown with filled circles, the PCDD compounds are shown with open squares, and the PCB compounds are shown with filled triangles. In the combined CoSCoSA model of all 52 compounds, the $r^2$ for the PCDF compounds is 0.87, the $r^2$ of the PCDD compounds is 0.84, and the $r^2$ of the PCB compounds is 0.75. The CoSCoSA model of 52 compounds is composed from 10 2D bins, 3 of which are derived from the COSY spectra, 4 from the medium-range, and the other 3 from the long-range distance spectra. Another interesting feature of this combined model is that each the 10 selected 2D bins contains peaks only found in one of the three compound types. There is a COSY and a medium-range bin that has "hits" (are occupied) for PCDDs only. There is another COSY and another medium-range bin that has hits for only PCBs. The remaining 6 bins have hits only from PCDFs. Only 6 of the 10 bins (2 bins for each compound type) used in the 52 compound model were used by the previous bin CoSCoSA models for each specific compound type.

TABLE 16

12 PCB compound model performance parameters n (parameters used), $r^2$, $q^2$, $q_2^2$, SE, F, and MLR Equation (C stands for COSY, M stands for medium-range and L stands for long-range spectra).

| Model | n | $r^2$ | $q^2$ | $q_2^2$ | SE | F | MLR Equation |
|---|---|---|---|---|---|---|---|
| 1D CoSA | 3 Bins | 0.66 | 0.30 | | 0.63 | 5.2 | |
| COSY | 3 Bins | 0.82 | 0.58 | 0.58 | 0.33 | 12.2 | −0.01714 * ($C_{135-125}$) + 0.0028 * ($C_{127-127}$) + 0.00275 * ($C_{133-131}$) |
| Mid + Long | 3 Bins | 0.77 | 0.66 | 0.47 | 0.35 | 9.1 | 0.00275 * ($M_{133-135}$) − 0.00299 * ($L_{133-133}$) + 0.00359 * ($L_{133-133}$) |
| COSY + Mid + Long | 3 Bins | 0.91 | 0.80 | 0.80 | 0.28 | 26.3 | −0.01467 * ($C_{137-125}$) − 0.00225 * ($M_{133-137}$) − 0.00301 * ($M_{131-139}$) |

TABLE 17

All 52 PCDF, PCDD, and PCB compound model performance parameters n (parameters used), $r^2$, $q^2$, $q_4^2$, and MLR Equation (C stands for COSY, M stands for medium-range and L stands for long-range spectra)

| Model | n | $r^2$ | $q^2$ | $q_4^2$ | SE | F | MLR Equation |
|---|---|---|---|---|---|---|---|
| 1D CoSA | 12 Bins | 0.75 | 0.61 | | 0.68 | 9.9 | |
| COSY + Mid + Long | 10 Bins | 0.85 | 0.73 | 0.52 | 0.51 | 24.0 | 0.01303 * ($C_{121-117}$) − 0.00688 * ($C_{141-123}$) − 0.00617 * ($C_{137-125}$) + 0.01908 * ($M_{119-117}$) − 0.00482 * ($M_{129-119}$) + 0.00392 * ($M_{133-135}$) + 0.00560 * ($M_{123-141}$) − 0.01177 * ($L_{119-123}$) − 0.00852 * ($L_{119-125}$) + 0.02260 * ($L_{121-127}$) |

Table 18 shows the correlation matrix for the 10 bins used to form the 52 compound CoSCoSA model. In table 18 there are only two correlations between bins that are greater than 0.25, so there is very little co-linearity between bins used to make the CoSCoSA model. The greatest average correlation between any bin with the other 10 bins was 0.1 and most of the average correlations were much lower than that. The lack of strong correlation among bins suggests that the resulting patterns were based on essentially orthogonal data. The best previous 1D CoSA model for all 52 compounds had an $r^2$ of 0.75 and a $q^2$ of 0.61 and was based on the 2 ppm bin size. The current CoSCoSA model had an $r^2$ of 0.85, a $q^2$ of 0.73, and a $q_4^2$ of 0.52 and was based on 10 2D bins selected from the 3D-connectivity matrix. When two outliers are removed from the cross-validation of the 52 compound CoSCoSA model, the $q^2$ and $q_4^2$ are 0.77, and thus much improved. Both outliers occurred when a compound had all zeros in every bin except for one column (bin) and that column had only two bin hits in it. When a column with only one remaining "hit" in it is used during the leave-one-out or leave-four-out cross-validation process, the linear regression B-coefficient can change sign. In comparison, a six component QSAR CoMFA model of polychlorinated and polybrominated biphenyls, dibenzofurans, and dibenzo-p-dioxins had an $r^2$ of 0.88 and a $q^2$ of 0.71. The 10 bin CoSCoSA model for the 52 PCDF, PCDD, and PCB compounds represents an improvement over previously published modeling approaches.

information reflecting the pull on the electron density of the middle ring oxygen atoms by the outer ring chlorine atoms. The number of chlorine substitutions and the position of the substitutions on the outer rings could significantly influence the electron densities of the inner ring carbons through the mechanism described. It is possible that the NMR bins of these carbon atoms are able to record these effects, and that pattern recognition is able to correlate the differences with the activities of the molecules.

In many of the CoSCoSA models, the overall F score, $r^2$, and $q^2$ were still increasing with increasing number of bins used in the model. The continued increase in overall F-test score, $q^2$ and $q_n^2$ values with bin number argues that overfitting had not yet occurred and that some continued improvement may be possible by using more bins in the models.

Example 8

Time-Dependent/Multistructural Multidimensional CoSCoSA Modeling

For some molecular properties, flexibility of the molecule is an important factor. For example, when a ligand binds to an enzyme the enzyme and ligand tend to conform to each other rather than fitting together rigidly as lock and key. Molecular flexibility may be introduced into CoSCoSA models by using multiple structures of a molecule to form a set of structural connectivity spectra.

TABLE 18

The correlation matrix for the 10 bins used to form the 52 compound CoSCoSA model.

| Bin | 1) COSY 121–117 | 2) COSY 141–123 | 3) COSY 137–125 | 4) MED 119–117 | 5) MED 129–119 | 6) MED 133–135 | 7) MED 123–141 | 8) LONG 119–123 | 9) LONG 119–125 | 10) LONG 121–127 |
|---|---|---|---|---|---|---|---|---|---|---|
| 1) | 1.00 | −0.08 | −0.04 | −0.04 | 0.05 | −0.06 | −0.04 | −0.05 | 0.08 | −0.07 |
| 2) | −0.08 | 1.00 | −0.07 | −0.08 | −0.15 | −0.11 | 0.00 | −0.10 | −0.17 | −0.12 |
| 3) | −0.04 | −0.07 | 1.00 | −0.04 | −0.07 | −0.05 | −0.03 | −0.05 | −0.09 | −0.06 |
| 4) | −0.04 | −0.08 | −0.04 | 1.00 | 0.05 | −0.06 | −0.04 | 0.23 | 0.42 | −0.07 |
| 5) | 0.05 | −0.15 | −0.07 | 0.05 | 1.00 | −0.11 | −0.07 | −0.10 | 0.11 | −0.13 |
| 6) | −0.06 | −0.11 | −0.05 | −0.06 | −0.11 | 1.00 | −0.05 | −0.08 | −0.13 | −0.09 |
| 7) | −0.04 | 0.00 | −0.03 | −0.04 | −0.07 | −0.05 | 1.00 | −0.05 | −0.08 | −0.06 |
| 8) | −0.05 | −0.10 | −0.05 | 0.23 | −0.10 | −0.08 | −0.05 | 1.00 | −0.03 | 0.46 |
| 9) | 0.08 | −0.17 | −0.09 | 0.42 | 0.11 | −0.13 | −0.08 | −0.03 | 1.00 | −0.04 |
| 10) | −0.07 | −0.12 | −0.06 | −0.07 | −0.13 | −0.09 | −0.06 | 0.46 | −0.04 | 1.00 |

Almost all the new CoSCoSA models described (26 PCDFs, 14 PCDDs, 12 PCBs, and combined 52 compounds) produced results at least equivalent to other modeling methods. All CoSCoSA models showed some form of improvement over our earlier 1D CoSA models based on the same or fewer 2 ppm bins.

The PCDF and PCDD CoSCoSA models showed major improvement in $r^2$ $q^2$, SE, and F-test over CoSASA models, in which the structural information is embedded on a 2D structural template grid. The CoSASA models were based on selected assigned chemical shifts, whereas the CoSCoSA models were based on selected 2D Bins from 2D $^{13}$C—$^{13}$C COSY and/or through-space 2D $^{13}$C—$^{13}$C distance spectra. Thus, there was more specific structural and spectral information available for the latter group of models. In many of the previous 1D CoSA models of PCDF and PCDD models of binding to AhR, the chemical shifts of carbon positions on the inside middle ring showed some of the strongest correlations to AhR binding. Likewise many of the CoSCoSA models for PCDF and PCDD compounds are based on bins from the middle ring carbons that are connected to the oxygen atom(s). A possible explanation for this is that these bins contain Structures of molecules that may be used to construct structural connectivity spectral data can be obtained in a number of ways. For example, structure can be calculated using molecular mechanics programs, calculated from typical bond angles and distances, determined from NMR spectra (solid or solution), and/or determined from solid phase crystal structures (including co-crystallized structures of ligand molecules and the proteins or nucleic acids that bind them). In a molecular mechanics program, simple equations are used to describe the energy needed to deviate from the most stable conformation of a molecule. These equations describe the molecular mechanics force field and allow a minimum energy conformation to be determined. Molecular mechanics programs that may be used to derive, for example, "lowest energy" structures include CHARMm and Discover (Accelrys, Burlington, Mass.), and AMBER (Peter Kollman, University of California, San Francisco). Thus, for example, a set of structural connectivity spectra may be predicted for each of the available types of structures, such as crystal and molecular mechanics structures, and used as descriptors of a particular molecule. If the molecule is rigid, these sets of spectral data will be similar. However, if the molecule is flexible, the data sets will be different. A combination of the variously derived data sets may be used to describe a flexible molecule. For example, where the molecule is flexible, multiple "bins" in the distance dimension of a 3D spectral connectivity matrix may be populated while "bins" in the spectral dimensions remain the same. As an alternative, a molecule may have spectra that vary for each of the structures and each structure may thus lead to different "bins" being populated in each of the dimensions. Regardless, the combination of multiple structural connectivity spectra may be used as a set of descriptors for a molecule.

An alternative to using "static" structures determined by the methods just described is to use a molecular dynamics calculation to produce a series of structures (called a "trajectory") that a molecule will "explore" during a certain amount of time (e.g. less than a nanosecond). Such calculations reflect the fluctuations in structure that molecules exhibit due to thermal energy. Molecular dynamics calculations utilize Newtonian equations of motion, a potential energy function, and an associated force field to follow the displacement of atoms in a molecule over time at a particular temperature and pressure. Since it is possible to adjust the temperature of the calculation, it is possible to model structural flexibility and more accurately predict intermolecular interactions at a particular temperature, for example, 37° C. Similarly, biological properties at elevated temperatures (e.g. ligand-protein interactions in thermophilic bacteria) could be modeled with this method. Alternatively, structures may also be obtained for lower and higher temperatures to more accurately model properties that occur over temperature ranges. Examples of Molecular Dynamics programs that may be used to obtain trajectories of molecular structure include CHARMm and Discover (Accelrys, Burlington, Mass.), AMBER (Peter Kollman, University of California, San Francisco), GROMOS and GROMACS (Biomos B.V., The Netherlands), Hyperchem (HyperCube, Inc., Gainesville, Fla.), and SYBYL (Tripos, St. Louis, Mo.). Advantageously, Hyperchem may be used on a personal computer just as the pattern-recognition programs used to establish CoSCoSA models may be executed on a personal computer.

Molecular dynamics structures may be sued to predict multiple sets of structural connectivity spectral data. For example, a set of 100 structures in a trajectory may be used to construct 100 structural connectivity spectra. If the molecule is rigid, the spectra will be similar. However, if the molecule is flexible the inter-component distance (or any geometric or topological relationship between components of structure attributable to particular spectral signals) will vary. If spectra are not recalculated for each structure, the only variable will be the distance. Therefore, a molecule may be described by a 3D spectral connectivity matrix where multiple "bins" in the inter-component distance dimension are populated for each cross-peak between components having assigned spectral features appearing in the spectral dimensions. The values in each of these distance "bins" may be normalized to represent the percentage of time (or the number of structures in a trajectory over a fixed period of time) a molecule exists in a structure with a particular inter-component distance. For example, if two structural components are separated by 4 angstroms 80% of the time and 5 Angstroms 20% of the time the distance "bins" covering these distances might be given values of 80 and 20 respectively. The more flexible a molecule is the more distance "bins" its trajectory may populate in the distance dimension, depending on the defined distance "bin" size. Alternatively, where structural distortions lead to significant changes in the spectral properties of a molecule, multiple "bins" in each dimension of the structural connectivity spectral data may be populated.

Example 9

Inverse CoSCoSA SDAR-Designing Molecules from Multidimensional SDAR Models

As an alternative to predicting a property of a molecule using an established CoSCoSA model, it is possible to design models based on an established CoSCoSA model. Because the CoSCoSA spectral data-activity methods of the disclosure can reveal important structural feature types (as revealed by their spectral features) as well as important structural relationships between the structural feature types, it is possible to use CoSCoSA models to "reverse engineer" a molecule from the CoSCoSA relationship for a particular endpoint. For example 1 f a CoSCoSA model reveals that a carbon atom having a $^{13}$C NMR chemical shift of 120 ppm at a distance of 5 Angstroms from a carbon atom having a chemical shift of 155 ppm is the most important feature determining a particular property of a group of molecules, other molecules that exhibit this feature may be designed. The method is analogous to the inverse QSAR method using chi or kappa indices (see, for example, Kier et al., "Design of Molecules from Quantitative Structure-activity Relationship Models," *J. Chem. Inf. Comput. Sci.*, 33:143, 1992).

Example 10

Endpoints

Endpoints for use with the SDAR methods of the disclosure encompass the full range of biological, chemical, and physical properties exhibited by molecules. The disclosed methods can be used to assist in drug design, biological activity predictions, toxicological predictions, chemical reactivity predictions, and metabolic pathway predictions. An endpoint is any molecular property or activity that can be measured qualitatively or quantitatively. Endpoints may be expressed in absolute or relative terms.

Endpoints may be chosen to establish SDARs that can be used to predict the environmental fate and toxicity of compounds. The ability of compounds to penetrate membranes, bind to enzyme active sites, react with soil, air, or water constituents, bind to soil constituents, hydrolyze, oxidize, and be transported in the environment can be used, along with spectral data for those compounds, to produce useful CoSCoSA models.

Spectral data can be used in combination with non-specific measures of toxicity, mutagenticity, teratogenicity, and carcinogenicity to establish CoSCoSA models. One example of such a non-specific measure is the Ames test. DNA damage and repair tests, Phosphorous-32 postlabeling, mutation induction in transgenes are others. Yet others include transgenic mouse assays, including the p53+/− deficient model, the Tg.AC model, the TgHras2 model, and the XPA deficient model. $LD_{50}$ and $EC_{50}$ may provide endpoints for CoSCoSA methods as well. Alternatively, the ability of compounds to induce specific biological outcomes such as cellular changes can be chosen as the endpoint used to establish the CoSCoSA models. For example, relevant tissues may be examined for changes at the cellular level using morphological, histochemical, or functional criteria. As appropriate, attention may be directed to such changes as the dose-relationships for apoptosis, cell proliferation, liver foci of cellular alteration, or changes in intercellular communication.

A CoSCoSA model may be established based upon any measurable response elicited in animals, plants, and microbes by exposure to a series of compounds. Examples include antiviral and antimicrobial activity. The ability of compounds to induce metabolic disorders such as alterations in sugar metabolism may provide a useful endpoint. Phytotoxicity and stimulation of plant growth and reproduction are other examples. Pesticidal activity is yet another example. Measures of anti-hypertensive activity, anti-pyretic activity, anti-depressant activity, and the like further illustrate useful endpoints that are usually related to human health. Similarly, phototoxicity, both specific and non-specific, may be correlated with spectral features to yield a CoSCoSA model.

Multiple endpoints may be utilized to establish multiple CoSCoSA models from sets of structural connectivity spectral data. Compounds may then be screened using multiple CoSCoSA models for any combination of desirable or undesirable endpoints. One example of a useful combination is that of maximal potential efficacy as a therapeutic agent with minimal potential side effects. Agrochemicals may be screened using multiple CoSCoSA models for species-specific toxicities and tolerances.

An especially useful application of the disclosed methods is for prediction of ligand-target molecule binding. The binding of a molecule to a target such a protein, nucleic acid, synthetic polymer, chimeric molecule, or membrane constituent is often the most important step in the elicitation of a particular property or activity by a molecule. Binding affinities for ligand-target molecule interactions can be expressed in either absolute (e.g., an equilibrium constant) or in relative (e.g., relative to a reference compound, as determined for example by a competitive binding experiment) terms. Example 1 above is one example of how the relative binding affinity of a series of molecules can be utilized along with spectral data to establish a predictive CoSCoSA models. CoSCoSA models based upon relative binding affinities may be useful for rapidly and inexpensively screening compounds for a particular activity. They also may be useful tools for rational drug design when used to identify the spectral, and thus structural, features responsible for that activity.

The metabolic pathway involved in the production or destruction of a series of molecules is another endpoint useful for the disclosed methods. A predictive CoSCoSA model based upon pathway-structure relationships may be able to predict the biosynthetic path for newly discovered naturally occurring compounds. Similarly, CoSCoSA models made using biodegradability as an endpoint may be useful for predicting the residence time of pollutants in the environment.

Rates of reaction and other measures of reactivity, such as site of reaction on a molecular structure, including the site of electrophilic aromatic substitutions on aromatic compounds, are useful chemical endpoints for the practice of the disclosed methods.

Physical constants such as water-octanol partition coefficients, vapor pressures, pKa, pKb, hydrophobicities, relative acidities and basicities as well as water solubilities can be used with spectral data to provide CoSCoSA models. Such estimates may be especially useful for physical properties that are difficult and time-consuming to measure. For example, octanol-water partition coefficients are important for modeling the environmental transport of chemicals. While the octanol-water partition coefficient of a compound might be available, it is less likely that transient species derived from that compound during biodegradation are available in sufficient quantities to measure their octanol-water partition coefficients. CoSCoSA modeling also provides an efficient way to predict the octanol-water partition coefficient for transient species for which environmental transport characteristics need to be modeled.

Other examples of useful endpoints may be found in Hansch and Leo, Exploring QSAR: *Fundamentals and Applications in Chemistry and Biology*, American Chemical Society, 1995. Further examples of useful endpoints may be found in *Quantitative Structure-Activity Relationships in Environmental Sciences—VII*, Chen and Schürmann, eds., SETAC Press, 1997.

Example 11

Spectral Data

Spectroscopy refers to branch of analytical chemistry in which atomic and molecular structure is studied by measuring radiant energy absorbed or emitted by a substance in any of the wavelengths of the electromagnetic spectrum, in response to excitation by an external energy source. The types of absorption and emission spectroscopy are usually identified by the wavelength involved, such as gamma-ray, X-ray, UV, visible, infrared, microwave, and radiofrequency. Nuclear magnetic resonance spectroscopy (NMR) examines differences in energy states created by a magnetic field. Spectral data refers to the measurements of the energy differences across the spectrum, and spectral patterns refer to differences in the detected energy differences measured across a region of the electromagnetic spectrum. Any instrumental method that produces data that depend upon the structural and quantum mechanical properties of a molecule may be utilized with the disclosed methods.

Spectral data as used in some embodiments includes the entire spectrum (or spectra) generated by the instrumental method (or methods) of spectroscopy or by calculation. Furthermore, the spectral data need not be assigned to particular structural features. In other embodiments the spectral data comprises only a portion of the spectrum or spectra available. The spectral portions utilized in the disclosed methods may cover a spectral region known to typically arise from one or more particular structural features. For example, with respect to $^{13}$C NMR spectral data, spectral data can be obtained from the entire $^{13}$C NMR spectrum (0 to 220 ppm), or at least half or a third of that spectrum, or at least a 10 ppm, 30 ppm, 60 ppm, 80 ppm, 100, or 150 ppm portion of the spectrum. Similarly $^{15}$N NMR data may be selected from the entire spectrum of 0 to 900 ppm (referenced to ammonia), or at least half or a third of that spectrum, or at least a 10 ppm, 30 ppm, 60 ppm, 80 ppm, 100, or 150 ppm portion of the spectrum. Likewise, 170 NMR data may be selected from the entire spectrum of −50 to 600 ppm (referenced to $H_2O$), or at least half or a third of that spectrum, or at least a 10 ppm, 30 ppm, 60 ppm, 80 ppm, 100, or 150 ppm portion of the spectrum. NMR data for $^{19}$F may be selected from the entire spectrum of −60 to 240 ppm (referenced to $CCl_3F$), or at least half or a third of that spectrum, or at least a 10 ppm, 30 ppm, 60 ppm, of 80 ppm portion of the spectrum. NMR data for $^{31}$P may be selected from the entire spectrum of −120 to 200 ppm (referenced to $P_4O_6$), or at least half or a third of that spectrum, or at least a 10 ppm, 30 ppm, 60 ppm, of 80 ppm portion of the spectrum. With respect to IR spectral data, for example, the spectral data can be obtained from the entire IR spectrum (4000 $cm^{-1}$ to 500 $cm^{-1}$), or at least a hundredth, fiftieth, quarter, or half of that spectrum, or at least a 35, 50, 100, 200, 500, or 1000 $cm^{-1}$ portion of the spectrum.

Nuclear magnetic resonance (NMR) data often contains a large amount of structural and electronic/steric information. NMR instrumentation is widely available and NMR spectra are obtained routinely during structure elucidation. Additionally, the NMR spectra of many compounds have already been measured and are available for example, in the Spectral Data Base System for Organic Compounds (Agency of Industrial Science, Japan), the *Aldrich Library of $^{13}C$ and $^{1}H$ FT NMR Spectra* (Pouchert and Behnke, Eds., Aldrich Chemical Company, Volumes 1-3, 1993), and *Spectral Data of Steroids* (Frenkel and Marsh, eds., Thermodynamics Research Center: College Station, 1994).

$^{13}C$ NMR and $^{1}H$ NMR spectral data (especially $^{13}C$ NMR spectral data) are very sensitive to subtle changes in substitution, conformation, chirality, and electronic density. Moreover, changes in $^{13}C$ NMR chemical shifts can occur at a site as many as five carbon atoms removed from the site of the variation. Solvation and proton-exchange effects on the electronic properties of molecules are more clearly reflected in $^{1}H$ NMR chemical shifts and line widths. Furthermore, modern FT-NMR instruments are capable of providing NMR spectral data for as little as 1 nanogram of a compound (an amount likely insufficient for performing standard bioassays such as the Ames test).

NMR data and structural connectivity spectral data may be segmented into bins prior to analysis, along with endpoint data, in a pattern-recognition program. Suitable bin widths will vary according to the identity of the nuclei for which the spectrum is generated, and whether the technique is one or two-dimensional. For one-dimensional $^{13}C$ NMR spectral data, the bin width may be varied from the digital resolution of the instrument (typically about 0.1 ppm) to about 50 ppm, such as from 0.5 ppm to 10 ppm, from 1.0 ppm to 5.0 ppm or from 1.0 to 3.0 ppm. For one-dimensional $^{1}H$ NMR spectral data, the bin width may be varied from the instrumental digital resolution (typically about 0.01 ppm) to about 2 ppm, such as from 0.2 ppm to 1.5 ppm or 0.5 ppm to 1.0 ppm. For two-dimensional $^{13}C$—$^{1}H$ heterocorrelation data, the bin may be defined by similar corresponding widths in both the $^{13}C$ and $^{1}H$ dimensions. NMR data of higher dimensions (e.g., three, four, etc.) including NMR spectral data from other nuclei, such as $^{15}N$, 31P, $^{19}F$, $^{17}O$, and $^{35}S$ may be used. Correspondingly, bins may be defined with respect to each dimension and may be of a width equal to the digital resolution of the data or greater. In general, NMR spectral bins may be from 0.1 ppm to 50 ppm, such as from 0.5 ppm to 25 ppm, from 1.0 ppm to 10 ppm, or from 2 ppm to 5 ppm.

In another embodiment spectral data is predicted from a molecule's structure. For example, $^{13}C$ NMR spectral data may be predicted by calculation (see, for example, Dios et al., *Science* 260:1491-1496, 1993 and Kvasnicka, V., *J. Math. Chem.*, 6: 63-76, 1991). Software for predicting $^{13}C$ NMR spectra is available from Advanced Chemistry Development (Toronto, Ontario, Canada). Other $^{13}C$ NMR prediction packages include an artificial neural network (Meiler et al., "Fast Determination of $^{13}C$ NMR Chemical Shifts Using Artificial Neural Networks," *J. Chem. INf. Comp. Sci.*, 40: 1169-1176, 2000) and NMRscape software from Bio-Rad Laboratories (Philadelphia, Pa.). Predicted $^{13}C$ NMR spectral data may be used, for example, to aid in rational drug design, by allowing proposed structures to be tested for potential activities before synthesis is attempted. Software for predicting $^{1}H$, $^{15}N$, $^{19}F$, and $^{31}P$ spectra is also available from Advanced Chemistry Development.

If predicted NMR data is utilized to establish an SDAR, the spectral data may be segmented into bins that are a width equal to the average standard deviation in chemical shift predicted by the method, or greater. Likewise, test structure predicted spectra may be segmented in a similar fashion. In general, predicted NMR spectral bins may be of the same dimensions as for experimental data, for example, from 0.1 ppm to 50 ppm, such as from 0.5 ppm to 25 ppm, from 1.0 ppm to 10 ppm, or from 2 ppm to 5 ppm.

Mass spectrometry can provide a measure of the size of a molecule, the size and identity of a molecule's structural subunits, and information regarding bond strengths within a molecule. Mass spectral data, especially electron impact mass spectral (EI MS) data, has already been obtained for many compounds and, even more so than NMR data, is available from convenient sources (see Example 1). EI MS data is also a standard technique used in structure elucidation.

Other mass spectrometric techniques that are useful for providing additional and often complementary information include time-of-flight mass spectrometry (TOF-MS), chemical ionization mass spectrometry (CI-MS), fast-atom bombardment (FAB). Modern TOF-MS spectrometers are capable of providing mass-spectral data from 1 ng or less of purified material (an amount that is likely insufficient for performing standard activity screens such as the Ames test).

Mass spectral data may be segmented into bins according to m/z ratio or its equivalent (for instance, into bins having widths ranging from about the digital resolution of the instrumental method, typically about 0.1 amu, to about 50 amu) or may be segmented according to integer m/z ratio, with non-integer m/z ratios being rounded to the nearest integer. In general, mass spectral bins may be defined to be of any width, for example, of a width from 0.5 amu to 20 amu, such as a width from 1.0 amu to 10 amu, or from 2.0 amu to 5 amu.

Infrared (IR) spectra may also be used. IR spectra may be treated in a similar fashion to NMR spectral data in that each spectrum may be separated into bins having a width that covers a range of spectral energies, for example, a range from about 1 $cm^{-1}$ to about 200 $cm^{-1}$, such as from 2 $cm^{1}$ to 100 $cm^{-1}$, from 5 $cm^{-1}$ to 50 $cm^{-1}$ or from 10 $cm^{-1}$ to 25 $cm^{-1}$. IR spectra may also be predicted from a molecule's structure, for example, using the Insight II C2IR/Raman program (Accelrys, San Diego, Calif.).

Ultraviolet-Visible (UV-Vis) spectral data, which is inherently reflective of the electronic energy levels of a molecule, may be used by segmenting the spectral data into bins of a certain spectral range, for example from about the digital resolution of the instrumental method to about 50 nm. For example, bins for UV-Vis data may be from 1 nm to 20 nm in width or from 2 to 10 nm in width. UV-Vis spectral data can be used, for example, in predicting phototoxicity under solar illumination. Similarly, fluorescence and phosphorescence spectra may be handled analogously to UV-Vis spectra and utilized to establish a CoSCoSA model. Fluorescence and phosphorescence spectra reflect the energy redistribution within a molecule upon absorption of light and thus may provide important structure descriptors for predicting the light driven properties of molecules.

In addition to the possibility of using a single type of spectral data to establish a CoSCoSA model, spectral data of various types may be combined to form composite sets of spectral data. Entire spectra or particular regions of spectra may be combined to yield spectral data sets that may be used in the disclosed methods. Spectral data may come from any composite of NMR, MS, IR, Fluorescence, Phosphorescence, and UV-Vis spectra, including composites of different species of spectra within these broad genera of spectra. Furthermore, different regions of any type of spectrum can be segmented into bins of different sizes so, for example, portions of a spectrum with many closely spaced signals can be described by narrow spectral bins and portions of a spectrum without many signals can be described by wide spectral bins.

In some embodiments the spectral data is not used in its raw form to establish an SDAR, but rather the data is subjected to pattern recognition analysis after some sort of pre-treatment to improve the ability of pattern recognition to extract the SDAR. For example normalization may be used to equalize the importance of spectral data derived from different instrumental methods when forming a composite, such as, a composite of MS data and NMR data wherein the maximum signals might be 100 and 1000 respectively. Scaling, such as autoscaling may be used to equalize the importance of inherently weak spectral data to inherently strong spectral data within the spectral data, for example, where UV-Vis absorption bands within an absorption spectrum have very different extinction coefficients. Fisher-weighting may be used to emphasize the spectral data or bins containing spectral data that are most important for predicting the endpoint, such as spectral data found in compounds with a large endpoint values but absent from compounds with small endpoint values.

In general, techniques for pre-treating data include artifact removal and/or linearization, centering, and scaling and weighting. A common form of artifact removal is baseline correction of a spectrum. Common linearizations include the conversion of spectral transmittance into spectral absorbance and the multiplicative scatter correction for diffuse reflectance spectra. Centering, sometimes called mean centering is simply the subtraction of the mean spectral signal at each frequency or m/z from each spectrum. Scaling or weighting involves multiplying all of the spectra by a different scaling factor for each sub-spectral region. This is done to increase or decrease the influence of certain spectral regions or features. A particular example of weighting is Fisher-weighting. Two types of scaling are typically encountered, variance scaling and autoscaling. Further discussion of data pretreatment may be found in Kramer, R., *Chemometric Techniques for Quantitative Analysis*, Marcel Dekker, Inc., 1998. Additional methods for the pre-treatment of data prior to pattern recognition are known in the art and are within the contemplated scope of the disclosed methods.

Since structural connectivity spectral data is utilized in some embodiments in the same manner as 3D-QSAR utilizes comprehensive descriptors for structural and statistical analyses (CODESSA) (see, Tong et al., *J. Med. Chem.*, 39: 380-387, 1995 and Collantes et al., *J. Anal. Chem.*, 68: 2038-2043, 1996, both of which are incorporated herein by reference) it is possible to combine the structural connectivity spectral data with other descriptors, including other types of spectral data descriptors, topological descriptors, electrostatic descriptors and bulk descriptors (such as the octanol/water partition coefficient). In particular embodiments, the other types of spectral data descriptors include unassigned spectral data. (see for example, U.S. patent application Ser. No. 09/629,557).

Example 12

Pattern-Recognition Programs

There are two types of pattern-recognition programs useful for detecting patterns in spectral data; statistical and artificial intelligence. Statistical methods include Principal Component Analysis (PCA) and variations of PCA such as linear regression analysis, principal component linear regression (PCLR) analysis, cluster analysis, canonical variates, and discriminant analysis, soft independent models of class analogy (SIMCA), expert systems, and auto spin (see, for example, Harrington, *RESolve Software Manual*, Colorado School of Mines, 1988, incorporated by reference, and Jain et al., "Statistical Pattern Recognition: A Review," *IEE Transactions on Pattern Analysis and Machine Intelligence,* 22: 4-37, 2000). Examples of statistical analysis software available include SPSS(SPSS Inc., Chicago, Ill.), JMP (SAS Inc., Cary N.C.), Stata (Stata Inc., College Station, Tex.) and Cluster (available to run from entropy:~dblank/public_html/cluster). Still other useful pattern recognition programs, including Statistica, were described in the preceding examples. In these pattern recognition methods, statistical decision boundaries (e.g. a distance, for example, a Euclidean or Mahanolobis distance, from the centroid of a cluster of data characteristic of a class) between the data for compounds of particular endpoint classes (qualitative preditions) or correlations (e.g. linear correlations) between patterns of data and the magnitude of an endpoint (quantitative predictions) are used to make predictions for test compounds. Such methods for making predictions are well known in the art and may be used with the disclosed methods. For example, in cluster analyses for qualitative predictions, the percent likelihood of class membership is provided by the statistical software. Depending upon the number of classes, the percentage likelihood that a compound is a member of a particular class should be greater than its likelihood that it is in another class. For example, where there are two classes, any likelihood greater than 50% provides a predictions of membership in the class, but of course a likelihood greater than 60%, such as greater than 70%, 80%, 90 or 95% is better, and provides greater assurance that a compound is correctly classified.

Artificial intelligence methods include neural networks and fuzzy logic. Neural networks may be one-layer or multilayer in architecture (See, for example, Zupan and Gasteiger, *Neural Networks for Chemists, VCH*, 1993, incorporated herein by reference). Examples of one-layer networks include Hopfield networks, Adaptive Bidirectional Associative Memory (ABAM), and Kohonen Networks. Examples of Multilayer Networks include those that learn by forward propagation, counter-propagation and back-propagation of error. Artificial neural network software is available from, among other sources, Neurodimension, Inc., Gainesville, Fla. (Neurosolutions) and The Mathworks, Inc., Natick, Mass. (MATLAB Neural Network Toolbox). In these methods, inputting data for a test compound will provide a prediction ouput based on the connections established in the network during training.

Spectral patterns can be analyzed using other approaches. For example, analog spectral peak patterns may be digitized, and image analysis may used to search for similarities or differences between the spectral patterns derived from a training set and the pattern exhibited by a test compound. If the patterns of data for molecules exhibiting a particular property are distinctive enough, visual analysis may be adequate to provide a prediction. Furthermore, it is possible to use any combination of pattern recognition techniques such as a combination of statistical pattern recognition and artificial intelligence pattern recognition, for example, a combination of principal components tree cluster analysis and neural networks techniques. Feature selection and feature extraction may also be used.

Example 13

Computer Environments for CoSCoSA Methods

The disclosed CoSCoSA methods may be implemented using a single computer or utilizing a distributed computing environment.

Exemplary Distributed Computing Environment

Figure 20:
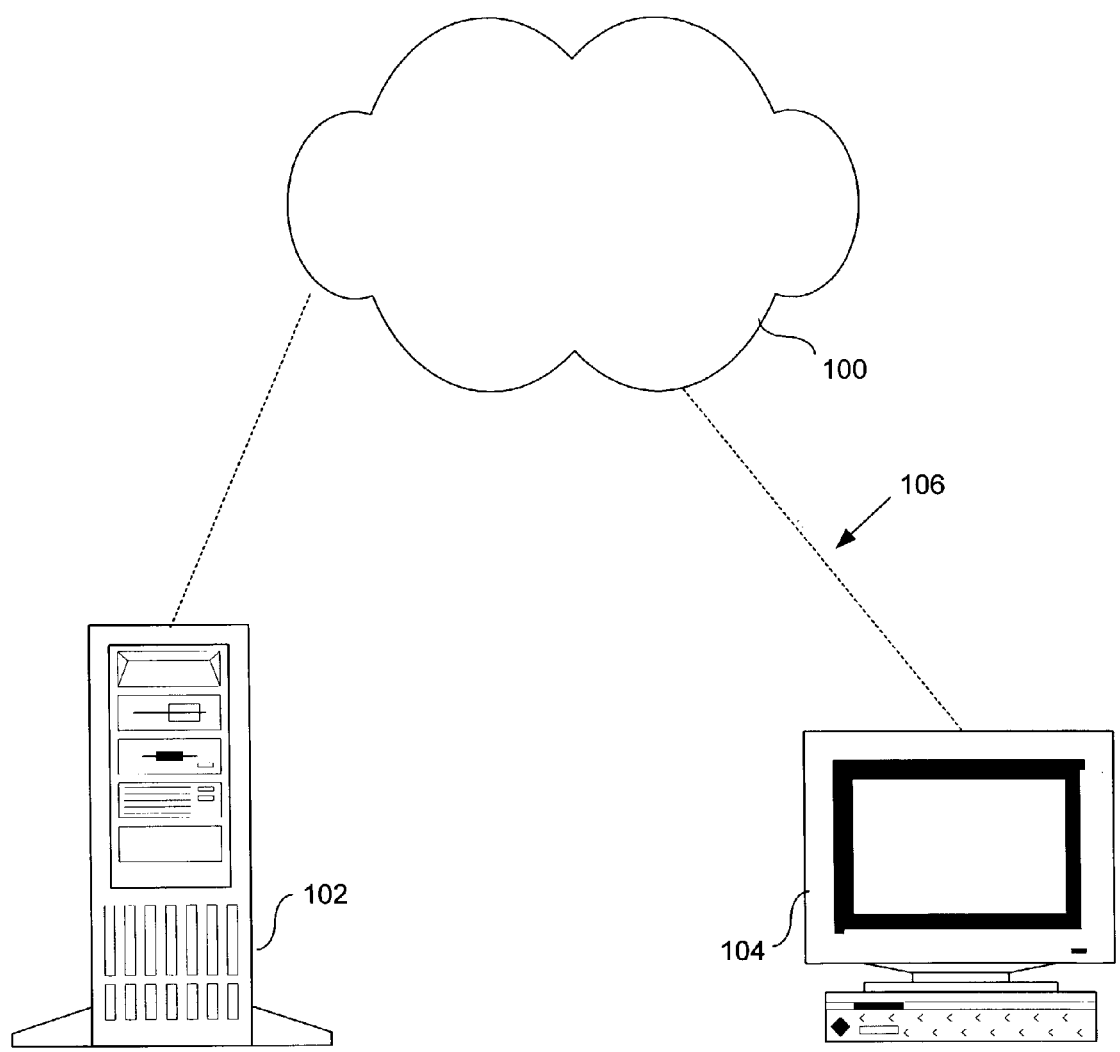
FIG. 20 is a diagram of a distributed computing environment in which the presently disclosed methods can be implemented.

FIG. 20 illustrates a distributed computing environment in which the software elements used to implement the disclosed methods may reside. The distributed computing environment 100 includes two computer systems 102, 104 connected by a connection medium 106. The computer systems 102, 104 can be any of several types of computer system configurations, including personal computers, multiprocessor systems, and the like. In terms of logical relation with other computer systems, a computer system can be a client, a server, a router, a peer device, or other common network node. Moreover, although FIG. 20 illustrates two computer systems 102, 104, the figure is equally applicable to an arbitrary, larger number of computer systems connected by the connection medium 106. Additional computer systems 102 or 104 may be connected by an arbitrary number of connection mediums 106. The connection medium 106 can comprise any local area network (LAN), wide area network (WAN), or other computer network, including but not limited to Ethernets, enterprise-wide computer networks, intranets and the Internet.

Portions of the software can be implemented in a single computer system 102 or 104, with the application later distributed to other computer systems 102, 104 in the distributed computing environment 100. Portions of the software may also be utilized in a distributed computing environment 100 where tasks are performed by a single computer system 102 or 104 acting as a remote processing device that is accessed through a communications network, with the distributed application later distributed to other computer systems in the distributed computing environment 100. In a networked environment, program modules comprising the software can be located on more than one computer system 102 or 104. Communication between the computer systems in the distributed computing network may advantageously include encryption of the communicated data.

Exemplary Computer System

Figure 21:
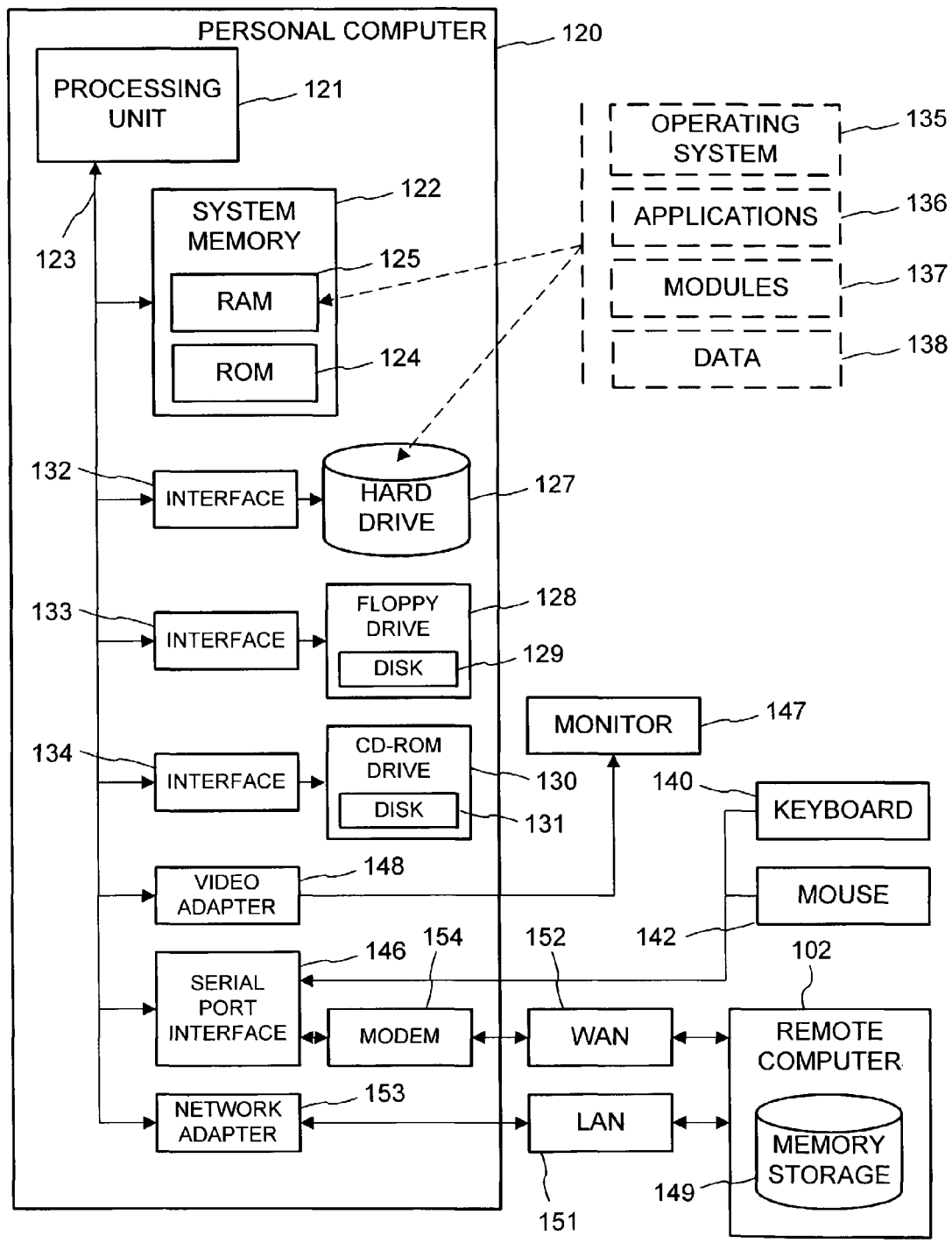
FIG. 21 is a block diagram of a computer system that can be used to implement the disclosed methods.

FIG. 21 illustrates an example of a computer system 120 that can serve as an operating environment for the software. With reference to FIG. 21 an exemplary computer system for implementing the disclosed methods includes a computer 120 (such as a personal computer, laptop, palmtop, set-top, server, mainframe, and other varieties of computer), including a processing unit 121, a system memory 122, and a system bus 123 that couples various system components including the system memory to the processing unit 121. The processing unit can be any of various commercially available processors, including Intel x86, Pentium and compatible microprocessors from Intel and others, including Cyrix, AMD and Nexgen; Alpha from Digital; MIPS from MIPS Technology, NEC, IDT, Siemens, and others; and the PowerPC from IBM and Motorola. Dual microprocessors and other multi-processor architectures also can be used as the processing unit 121.

The system bus can be any of several types of bus structure including a memory bus or memory controller, a peripheral bus, and a local bus using any of a variety of conventional bus architectures such as PCI, VESA, AGP, Microchannel, ISA and EISA, to name a few. The system memory includes read only memory (ROM) 124 and random access memory (RAM) 125. A basic input/output system (BIOS), containing the basic routines that help to transfer information between elements within the computer 120, such as during start-up, is stored in ROM 124.

The computer 120 further includes a hard disk drive 127, a magnetic disk drive 128, e.g., to read from or write to a removable disk 129, and an optical disk drive 130, e.g., for reading a CD-ROM disk 131 or to read from or write to other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of data, data structures, computer-executable instructions, etc. for the computer 120. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, can also be used in the exemplary operating environment.

A number of the program modules can be stored in the drives and RAM 125, including an operating system 135, one or more application programs 136, other program modules 137, and program data 138.

A user can enter commands and information into the computer 120 through a keyboard 140 and pointing device, such as a mouse 142. Other input devices (not shown) can include a microphone, satellite dish, scanner, or the like. These and other input devices are often connected to the processing unit 121 through a serial port interface 146 that is coupled to the system bus, but can be connected by other interfaces, such as a parallel port, game port or a universal serial bus (USB). A monitor 147 or other type of display device is also connected to the system bus 123 via an interface, such as a video adapter 148. In addition to the monitor, computers typically include other peripheral output devices (not shown), such as printers.

The computer 120 can operate in a networked environment using logical connections to one or more other computer systems, such as computer 102. The other computer systems can be servers, routers, peer devices or other common network nodes, and typically include many or all of the elements described relative to the computer 120, although only a memory storage device 149 has been illustrated in FIG. 21. The logical connections depicted in FIG. 21 include a local area network (LAN) 151 and a wide area network (WAN) 152. Such networking environments are common in offices, enterprise-wide computer networks, intranets and the Internet.

When used in a LAN networking environment, the computer 120 is connected to the local network 151 through a network interface or adapter 153. When used in a WAN networking environment, the computer 120 typically includes a modem 154 or other means for establishing communications (e.g., via the LAN 151 and a gateway or proxy server 155) over the wide area network 152, such as the Internet. The modem 154, which can be internal or external, is connected to the system bus 123 via the serial port interface 146. In a networked environment, program modules depicted relative to the computer 120, or portions thereof, can be stored in the remote memory storage device. It will be appreciated that the network connections shown are exemplary and other means of establishing a communications link between the computer systems (including an Ethernet card, ISDN terminal adapter, ADSL modem, 10BaseT adapter, 100BaseT adapter, ATM adapter, or the like) can be used.

In accordance with the practices of persons skilled in the art of computer programming, particular embodiments of the disclosed methods are described in FIGS. 1 and 16 with reference to acts and symbolic representations of operations that may be performed by the computer 120. Such acts and operations are sometimes referred to as being computer-executed. It will be appreciated that the acts and symbolically represented operations include the manipulation by the processing unit 121 of electrical signals representing data bits which causes a resulting transformation or reduction of the electrical signal representation, and the maintenance of data bits at memory locations in the memory system (including the system memory 122, hard drive 127, floppy disks 129, and CD-ROM 131) to thereby reconfigure or otherwise alter the computer system's operation, as well as other processing of signals. The memory locations where data bits are maintained are physical locations that have particular electrical, magnetic, or optical properties corresponding to the data bits.

In view of the many possible embodiments to which the principles of the illustrated methods may be applied, it should be recognized that the particular embodiments described above are only specific examples of the invention and should not be taken as a limitation on the scope of the invention. Rather, the scope of the invention is defined by the following claims. We therefore claim as our invention all that comes within the scope and spirit of these claims.

We claim:

1. A computer implemented method for predicting a property of a test molecule, comprising:
    selecting a training set of molecules that exhibit a range of endpoint values;
    obtaining a 3D connectivity matrix for the molecules of the training set, wherein the 3D connectivity matrix comprises inter-atomic through-space distances between atoms of the molecules and spectral data attributable to those atoms;
    with a computer, detecting a pattern of 3D connectivity data in the training set 3D connectivity matrix that is correlated with the endpoint values;
    obtaining a 3D connectivity matrix for the test molecule; and
    with the computer, comparing the 3D connectivity matrix of the test molecule to the detected pattern of 3D connectivity data in the training set 3D connectivity matrix to predict the property of the test molecule.

2. The method of claim 1 where the 3D connectivity matrices of the molecules of the training set and the test molecule further comprise IR data.

3. The method of claim 1 where the 3D connectivity matrices of the molecules of the training set and the test molecule comprise $^{13}$C NMR data, $^{1}$H NMR data, $^{17}$O NMR data, $^{15}$N NMR data, $^{31}$P NMR data, $^{35}$S NMR data or combinations thereof.

4. The method of claim 3 where the 3D connectivity matrices of the molecules of the training set and the test molecule comprise $^{13}$C NMR data.

5. The method of claim 4 where the 3D connectivity matrices of the molecules of the training set and the test molecule comprise $^{13}$C—$^{13}$C COSY data, $^{13}$C—$^{13}$C distance data, and combinations thereof.

6. The method of claim 1 where detecting a pattern comprises statistical pattern recognition.

7. The method of claim 6 where the 3D connectivity matrices of the training set and the test molecule are segmented into bins prior to the statistical pattern recognition.

8. The method of claim 6 where the statistical pattern recognition comprises determining the principal components of the 3D connectivity matrices that are correlated with the endpoint values.

9. The method of claim 1 where at least one endpoint value is a biological endpoint value.

10. The method of claim 1 where at least one endpoint value is a quantitative endpoint value and the pattern of 3D connectivity matrices correlates with the magnitude of the quantitative endpoint value.

11. The method of claim 1, wherein the predicted multidimensional NMR data of the 3D connectivity matrices comprise multidimensional $^{13}$C NMR spectra.

12. The method of claim 11, wherein the 3D connectivity matrices further comprise spectral data selected from $^{1}$H spectral data, $^{15}$N spectral data, $^{19}$F spectral data, $^{31}$P spectral data or combinations thereof.

13. The method of claim 1, further comprising displaying the predicted property of the test molecule.

14. The method of claim 1, wherein the predicted property is biological activity of the test molecule.

15. The method of claim 14, wherein the predicted property is binding of the test molecule to a target.

16. The method of claim 1, wherein the 3D connectivity matrix further comprises through-bond inter-atomic distances.

17. The method of claim 16, wherein the through-bond distances are determined with respect to at least one anchor atom.

18. The method of claim 1, further comprising arranging the 3D connectivity matrix as two or more 2D connectivity planes, wherein each of the two or more planes is associated with a respective through-space distance category.

19. The method of claim 18, wherein the spectral data attributable in at least one of the two or more planes is normalized based on a probability with which at least one molecule of the training set of molecules exists in at least two or more conformations having respective through-space inter-atomic distances.

20. The method of claim 1, further comprising reducing the 3D connectivity matrix so as to include only through-space inter-atomic distances of at least 5 Angstroms.

21. The method of claim 1, further comprising reducing the 3D connectivity matrix so as to remove through-space inter-atomic distances between 2 Angstroms and 5 Angstroms.

22. The method of claim 1, wherein the 3D spectral connectivity matrix for the test molecule comprises a first axis for the chemical shift of a first atom in the test molecule, a second axis for the chemical shift of a second atom in the test molecule, and a third axis for the through-space inter-atomic distance between the first and second atoms of the test molecule.

23. A computer implemented method for predicting a property of a test molecule, comprising:
    selecting a training set of molecules that exhibit a range of endpoint values;
    obtaining a 3D connectivity matrix for the molecules of the training set, wherein the 3D connectivity matrix comprises inter-atomic through-space distances between atoms of the molecules and spectral data attributable to those atoms;
    with a computer, detecting a pattern in the training set 3D connectivity matrix that is correlated with the endpoint values;
    comparing the predicted structural connectivity spectral data of the test molecule to the detected pattern of data in the training set 3D connectivity matrix to predict the property of the test molecule,
    wherein the predicted 3D matrix of spectral connectivity data comprises a through-space structural relationship.

24. A computer implemented method for predicting a property of a test molecule, comprising:
    selecting a training set of molecules that exhibit a range of endpoint values;
    obtaining a 3D connectivity matrix for the molecules of the training set, wherein the 3D connectivity matrix comprises inter-atomic through-space distances between atoms of the molecules and spectral data attributable to those atoms;

with a computer, detecting a pattern in the training set 3D connectivity matrix that is correlated with the endpoint values;

comparing the predicted 3D connectivity data of the test molecule to the detected pattern of data in the training set 3D connectivity matrix to predict the property of the test molecule, and wherein the predicted 3D connectivity matrix comprises through-bond neighboring carbon-to-carbon connectivities.

25. A computer implemented method for predicting a property of a test molecule, comprising:

obtaining a 3D spectral connectivity matrix for the test molecule, wherein the 3D spectral connectivity matrix for the test molecule comprises a first axis for the chemical shift of a first atom in the test molecule, a second axis for the chemical shift of a second atom in the test molecule, and a third axis for the through-space inter-atomic distance between the first and second atoms of the test molecule;

identifying a training set of molecules, at least one training set molecule having the property to be predicted;

obtaining a 3D spectral connectivity matrix for the training set of molecules, wherein the 3D spectral connectivity matrix for the training set of molecules comprises a first axis for the chemical shift of a first atom in the at least one training set molecule, a second axis for the chemical shift of a second atom in the at least one training set molecule, and a third axis for the inter-atomic distance between the first and second atoms in the at least one training set molecule; and with a computer, comparing the 3D spectral connectivity matrices for the test molecule and the training set of molecules to predict the property of the test molecule.

26. The method of claim 25, wherein the chemical shift data comprise $^{13}$C NMR data, $^1$H NMR data, $^{17}$O NMR data, $^{15}$N NMR data, $^{31}$P NMR data, $^{35}$S NMR data or combinations thereof.

27. The method of claim 25, wherein the 3D spectral connectivity matrices of the molecules of the training set and the test molecule comprise predicted multidimensional NMR data.

28. A computer implemented method for predicting a property of a test molecule, comprising:

with a computer, obtaining a 3D spectral connectivity matrix for the test molecule, wherein the 3D spectral connectivity matrix for the test molecule comprises a first axis for the chemical shift of a first atom in the test molecule, a second axis for the chemical shift of a second atom in the test molecule, and a third axis for the through-space inter-atomic distance between the first and second atoms of the test molecule, wherein the chemical shifts are saved as two-dimensional bins within a certain spectral range and normalized to an integer;

identifying a training set of molecules, at least one training set molecule having the property to be predicted;

with the computer, obtaining a 3D spectral connectivity matrix for the training set of molecules, wherein the 3D spectral connectivity matrix for the training set of molecules comprises a first axis for the chemical shift of a first atom in the at least one training set molecule, a second axis for the chemical shift of a second atom in the at least one training set molecule, and a third axis for the inter-atomic distance between the first and second atoms in the at least one training set molecule wherein the chemical shifts are saved as two-dimensional bins within a certain spectral range and normalized to an integer; and comparing the 3D spectral connectivity matrices for the test molecule and the training set of molecules.

29. The method of claim 28, wherein the spectral range is between 2.0 ppm and 10 ppm.

30. The method of claim 28, wherein the 3D spectral connectivity matrix for the training set of molecules and the 3D spectral connectivity matrix for the test molecule are reduced to principal components.

31. A computer implemented method for predicting estrogen receptor binding of a test molecule, comprising:

obtaining a 3D spectral connectivity matrix for the test molecule, wherein the 3D spectral connectivity matrix for the test molecule comprises a first axis for the chemical shift of a first atom in the test molecule, a second axis for the chemical shift of a second atom in the test molecule, and a third axis for the through-space inter-atomic distance between the first and second atoms of the test molecule;

identifying a training set of molecules known to bind estrogen receptor;

with a computer, obtaining a 3D spectral connectivity matrix for the training set of molecules known to bind estrogen receptor, wherein the 3D spectral connectivity matrix for the training set of molecules comprises a first axis for the chemical shift of a first atom in the at least one training set molecule, a second axis for the chemical shift of a second atom in the at least one training set molecule, and a third axis for the inter-atomic distance between the first and second atoms in the at least one training set molecule; and comparing the 3D spectral connectivity matrices for the test molecule and the training set of molecules to predict estrogen receptor binding of the test molecule.

32. A computer implemented method for predicting aryl hydrocarbon receptor binding of a test molecule, comprising:

obtaining a 3D spectral connectivity matrix for the test molecule, wherein the 3D spectral connectivity matrix for the test molecule comprises a first axis for the chemical shift of a first atom in the test molecule, a second axis for the chemical shift of a second atom in the test molecule, and a third axis for the through-space inter-atomic distance between the first and second atoms of the test molecule;

identifying a training set of molecules known to bind aryl hydrocarbon receptor;

with a computer, obtaining a 3D spectral connectivity matrix for the training set of molecules known to bind aryl hydrocarbon receptor, wherein the 3D spectral connectivity matrix for the training set of molecules comprises a first axis for the chemical shift of a first atom in the at least one training set molecule, a second axis for the chemical shift of a second atom in the at least one training set molecule, and a third axis for the inter-atomic distance between the first and second atoms in the at least one training set molecule; and comparing the 3D spectral connectivity matrices for the test molecule and the training set of molecules to predict aryl hydrocarbon receptor binding of the test molecule.

33. The method of claim 32, further comprising displaying the predicted aryl hydrocarbon receptor binding.

34. A computer implemented method for predicting steroid binding of a test steroid to aromatase, comprising:

selecting a plurality of steroids that form a training set;
obtaining core steroid structures, substitution patterns, a plurality of conformations and associated probabilities, and experimental aromatase bindings for each of the plurality of steroids;
calculating a $^{13}C$ spectrum for each of the plurality of steroids;
producing comparative structural connectivity spectral analysis (CoSCoSA) models for the plurality of steroids, comprising producing a 3D spectral connectivity data matrix for each of the plurality of steroids, wherein the 3D spectral connectivity matrices comprise a first axis for the chemical shifts of a first atom in the steroid, a second axis for the chemical shift of a second atom in the steroid, and a third axis for the through-space inter-atomic distance between the first and second atoms of the steroid;
reducing the 3D spectral connectivity data matrix so as to produce sets of 2D spectral planes including a short range plane, a medium range plane, and a long range plane, wherein the short range plane, the medium range plane, and the long range plane include inter-atomic through-space distances for the plurality of steroids;
performing principal component linear regressions (PCLRs) on the CoSCoSA models based on the 3D spectral connectivity matrices and the sets of 2D spectral planes;
evaluating the PCLRs associated with the 3D spectral connectivity matrices and the sets of 2D spectral planes based on a leave-one-out cross-validation using a ratio of a sum of differences between actual and predicted activity to a sum of squared deviations between measured and mean activities of each steroid;
based on the ratios, selecting at least one CoSCoSA model; and
using the at least one selected CoSCoSA model, estimating a log of relative binding affinity (log(RBA)) of the test steroid with respect to aromatase.

35. A computer readable storage medium storing computer-executable instructions for performing a method comprising:
receiving a training set of molecules that exhibit a range of endpoint values;
obtaining a 3D connectivity matrix for the molecules of the training set, wherein the 3D connectivity matrix comprises inter-atomic through-space distances between atoms of the molecules and spectral data attributable to those atoms;
detecting a pattern of 3D connectivity data in the training set 3D connectivity matrix that is correlated with the endpoint values;
obtaining a 3D connectivity matrix for the test molecule; and
comparing the 3D connectivity matrix of the test molecule to the detected pattern of 3D connectivity data in the training set 3D connectivity matrix to predict the property of the test molecule, wherein the 3D connectivity matrices of the molecules of the training set and the test molecule comprise predicted multidimensional NMR data.

* * * * *